US006627747B1

(12) United States Patent
Fritz et al.

(10) Patent No.: US 6,627,747 B1
(45) Date of Patent: Sep. 30, 2003

(54) ESSENTIAL BACTERIAL GENES AND THEIR USE

(75) Inventors: Christian Fritz, Natick; Philip Youngman; Luz-Maria Guzman, both of Boston, all of MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/393,858

(22) Filed: Sep. 9, 1999

Related U.S. Application Data

(60) Provisional application No. 60/099,578, filed on Sep. 9, 1998.

(51) Int. Cl.[7] .............................................. C07H 21/04
(52) U.S. Cl. ................ 536/23.7; 435/320.1; 435/252.3; 435/243; 435/69.1; 424/244.1; 536/24.32
(58) Field of Search ............................ 536/23.7, 24.32; 435/320.1, 252.3, 243, 69.1; 424/244.1

(56) References Cited

U.S. PATENT DOCUMENTS

| | | | |
|---|---|---|---|
| 4,215,051 A | 7/1980 | Schroeder et al. | ........ 260/346.7 |
| 4,376,110 A | 3/1983 | David et al. | ................. 436/513 |
| 4,679,582 A | 7/1987 | Zwicker | ..................... 137/71 |
| 4,704,692 A | 11/1987 | Ladner | ........................ 364/496 |
| 4,946,778 A | 8/1990 | Ladner et al. | .............. 435/69.6 |
| 5,283,173 A | 2/1994 | Fields et al. | ..................... 435/6 |
| 5,585,277 A | 12/1996 | Bowie et al. | ................ 436/518 |

FOREIGN PATENT DOCUMENTS

| | | | |
|---|---|---|---|
| EP | 0 911 410 A2 | 4/1999 | |
| WO | 97/42210 | 11/1997 | |
| WO | 98/06734 | 2/1998 | |
| WO | 98/18931 | 5/1998 | ........... C12N/15/31 |
| WO | 99/24579 | 5/1999 | |

OTHER PUBLICATIONS

Lindler et al. J. Bacteriol. 1987. 169(7): 3199–3208.*
Terao et al. Submitted Jul. 8, 1998. EMBL/Genbank Accession #AB016077.*
Barash et al. Sequence alignments from WO/98/18931.*
Akerley et al., "Systematic identification of essential genes by in vitro mariner mutagenesis," Proc. Natl. Acad. Sci. USA, vol. 95, Jul. 1998, pp. 8927–8932.
Baltz et al., "DNA Sequence Sampling of the *Streptococcus pneumoniae* Genome to Identify Novel Targets for Antibiotic Development," Microbial Drug Resistance, vol. 4, No. 1, Mar. 1998, pp. 1–9.
Pillutla et al., "Deletion of putative effector region of Era, an essential GTP–binding protein in *Escherichia coli*, causes a dominant–negative phenotype," FEMS Microbiology Letters, vol. 143, No. 1, Sep. 15, 1996, pp. 47–55.
Sorokin et al., "Hypothetical 48.8 kd GTP–binding protein in CMK–GPSA intergenic region" Swissprot Accession No. P50743; Oct. 1, 1996, (XP002140727).

Cole et al.; "The EBV–Hybridoma Technique and its Application to Human Lung Cancer"; *Monoclonal Antibodies and Cancer Therapy*; pp. 77–96; 1985.
Bollag et al.; "[18] Intrinsic and GTPase–Activating Protein–Stimulated Ras GTPase Assays"; *Methods in Enzymology 255*; pp. 161–170; 1995.
Barbeyron et al.; "Arylsulphatase from *Alteromonas carrageenovora*"; *Microbiology 141(11)*; pp. 2897–2904; 1995.
White; "The Yeast Two–Hybrid System: Forward and Reverse"; *Proc. Natl. Acad. Sci. USA 93*; pp. 10001–10003; 1996.
Vidal et al.; "Reverse two–hybrid and one–hybrid systems to detect dissociation of protein–protein and DNA–protein interactions"; *Proc. Natl. Acad. Sci. USA 93(19)*; pp. 10315–10320; 1996.
Karlin et al.; "Methods for assessing the statistical significance of molecular sequence features by using general scoring schemes"; *Proc. Natl. Acad. Sci. USA 86(6)*; pp. 2264–2268; 1990.
Karlin et al.; "Applications and statistics for multiple high–scoring segments in molecular sequences"; *Proc. Natl. Acad. Sci. USA 90(12)*; pp. 5873–5877; 1993.
Altschul et al.; "Gapped BLAST and PSI–BLAST: a generation of protein database search programs"; *Nucleic Acids Research 25(17)*; pp. 3389–3402; 1997.
Altschul et al.; "Basic Local Alignment Search Tool"; *J. Mol. Biol. 215(3)*; pp. 403–410; 1990.
Rüther et al.; "Easy identification of cDNA clones"; *The EMBO Journal 2(10)*; pp. 1791–1794; 1983.
Smith et al.; "Molecular Engineering of the *Autographa californica* Nuclea Polyhedrosis Virus Genome: Deletion Mutations Within the Polyhedrin Gene"; *Journal of Virology 46(2)*; pp. 584–593; 1983.
Logan et al.; "Adenovirus tripartite leader sequence enhances translation of mRNAs late after infection"; *Proc. Natl. Acad. Sci. USA 81(12)*; pp. 3607–3928; 1984.
Bitter et al.; "Expression and Secretion Vectors for Yeast"; *Methods of Enzymology 153(D)*; pp. 516–544; 1987.
Mulligan et al.; "Selection for animal cells that express the *Escherichia coli* gene coding for xanthine–guanine phosphoribosyltransferase"; *Proc. Nat'l. Acad. Sci 78(4)*; pp. 2072–2076; 1981.
Colbère–Garapin et al.; "A New Dominant Hybrid Selective Marker for Higher Eukaryotic Cells"; *J. Mol. Biol. 150*; pp. 1–14; 1981.

(List continued on next page.)

*Primary Examiner*—Jennifer E. Graser
(74) *Attorney, Agent, or Firm*—Fish & Richardson P.C.

(57) ABSTRACT

Disclosed are two genes, termed "yphC" and "yqjK," found in *Streptococcus pneumoniae*, which are essential for survival for a wide range of bacteria. These genes and the essential polypeptides that they encode, as well as homologs and orthologs thereof, can be used to identify antibacterial agents for treating a broad spectrum of bacterial infections.

5 Claims, 20 Drawing Sheets

OTHER PUBLICATIONS

Santerre et al.; "Expression of prokaryotic genes for hygromycin B and G418 resistance as—dominant–selection markers in mouse L cells"; *Gene 30(1,2,3)*; pp. 147–154 ; 1984.

Janknecht et al.; "Rapid and efficient purification of native histidine–tagged protein expressed by recombinant vaccinia virus"; *Proc. Natl. Acad. Sci. USA 88(20)*; pp. 8865–9376; 1991.

Köhler et al.; "Continuous cultures of fused cells secreting antibody of predefined specificity"; *Nature 256*; pp. 495–497; 1975.

Köhler et al.; "Derivation of specific antibody–producing tissue culture and tumor lines by cell fusion"; *European Journal of Immunology 6(7)*; pp. 511–519, 1976.

Köhler et al.; "Fusion between immunoglobulin–secreting and nonsecreting myeloma cell lines"; *European Journal of Immunology 6(4)*; pp. 292–295; 1976.

Kozbar et al.; "The production of monoclonal antibodies from human lymphocytes"; *Immunology Today 4(1)*: pp. 72–79; 1983.

Cote et al.; "Generation of human monocolonal antibodies reactive with cellular antigens"; *Proc. Natl. Acad. Sci. USA 80*; pp. 2026–2030; 1983.

Morrison et al.; "Chimeric human antibody molecules: Mouse antigen–binding domains with human constant region domains"; *Proc. Natl. Acad. Sci. USA 81*: pp. 6851–6855; 1984.

Neuberger et al.; "Recombinant antibodies possessing novel effector functions"; *Nature 312*; pp. 604–608; 1984.

Takeda et al.; "Construction of chimaeric processed immunoglobulin genes containing mouse variable and human constant region sequences"; *Nature 314(6010)*; pp. 452–454; 1985.

Huse et al.; "Generation of a Large Combinatorial Library of the Immunoglobulin Repertoire in Phage Lambda"; *Science 264*; pp. 1275–1281; 1989.

West et al.; "Identification of Concanavalin A Receptors and Galactose–binding Proteins in Purified Plasma Membranes of *Dictyostelium discoideum*"; *The Journal of Cell Biology 74*; pp. 264–273; 1977.

Chien et al.; "The two–hybrid system: A method to identify and clone genes for proteins that interact with a protein of interest"; *Proc. Natl. Acad. Sci. USA 88(21)*; pp. 9578–9582; 1991.

Fields et al.; "A novel genetic system to detect protein–protein interactions"; *Nature 340*; pp. 245–246; 1989.

Le Douarin et al.; "A new version of the two–hybrid assay for detection of protein–protein interactions"; *Nucleic Acids Research 23(5)*; pp. 876–878.

Lanzetta et al.; "An improved Assay for Nanomole Amounts of Inorganic Phosphate"; *Analytical Biochemistry 100*; pp. 95–97; 1979.

\* cited by examiner

```
  1 ATGGCCCTACCAACTATTGCCATTGTTGGAGGACGTCCCAATGTTGGGAAATCAACCCTATTAATCGATCGCTGGTGAGCGAATCTCCATTGTAGAAGATG   100
    TACCGGGATGGTTGATAACGGTAACATCCTGCAGGGTTACAACCCTTTAGTTGGGATAATTAGCCTAGCGACCACTCGCTTAGAGGTAACATCTTCTAC

1  M  A  L  P  T  I  A  I  V  G  R  P  N  V  G  K  S  T  L  F  N  R  I  A  G  E  R  I  S  I  V  E  D  V    34

101 TCGAAGGAGTGACACGTGACCGTGATTATGCAACGGGTGAGTGGCTCAATCGTTCTTTTAGCATGATTGATACAGGAGGAATTGATGATGTCGATGCTCC   200
    AGCTTCCTCACTGTGCACTGGCACTAATACGTTGCCCACTCACCGAGTTAGCAAGAAAATCGTACTAACTATGTCCTCCTTAACTACTACAGCTACGAGG

35  E  G  V  T  R  D  R  I  Y  A  T  G  E  W  L  N  R  S  F  S  M  I  D  T  G  G  I  D  D  V  D  A  P    67

201 TTTCATGGAACAAATCAAGCACCAGGCAGAAATTGCCATGGAAGAAGCAGATGTTATCGTCTTTGTCGTCCGGTAAGGAAGGAATTACCGATGCAGAC   300
    AAAGTACCTTGTTTAGTTCGTGGTCCGTCTTTAACGGTACCTTCTTCGTCTACAATAGCAGAAACAGCAGGCCATTCCTTCCTTAATGGCTACGTCTG

68  F  M  E  Q  I  K  H  Q  A  E  I  A  M  E  E  A  D  V  I  V  F  V  V  S  G  K  E  G  I  T  D  A  D   100

301 GAATACGTAGCCCGTAAGCTTTATAAGACCCACAAACCAGTGTATCCTCGCAGTTAACAAGGTGGACAACCCTGAGATGCGAAATGATATCTATGATTTCT   400
    CTTATGCATCGGGCATTCGAAATATTCTGGGTGTTTGGTCACACAGTCAATTGTTCCACCTGTTGGGACTCTACGTTACTATAGATACTAAAGA

101  E  Y  V  A  R  K  L  Y  K  T  H  K  P  V  I  L  A  V  N  K  V  D  N  P  E  M  R  N  D  I  Y  D  F  Y   134

401 ATGCCCTCGGTTTGGGTGAACCACTGGTGACGGATAGACAGTAGACATAGCATGTCCCTACATGATCTACGCTAACACCTTTGGAAGGTTTACTTAT   500
    TACGGGAGCCAAACCCACTGGTGACCACTGCCTATCTGTCATCTGTATCGGTACAGGGATGTACTAGATGCGATTGTGAAAACCTTCCAAATGAATA

135  A  L  G  L  G  E  P  L  P  I  S  S  V  H  G  I  G  T  G  D  V  L  D  A  I  V  E  N  L  P  N  E  Y   167

501 TGAAGAGAAAATCCAGATGTCATTAAGTTTAGCTTGATTGGTCGTCCTAACGTTGGAAAATCAAGCTTGAATTAATGCTATCTTGGGAGAAGACCGTGTC   600
    ACTTCTCTTTTAGGTCTACATGTAATTCAAGTTCAACCTTTTAGTTCGAACTAATTACGATAGAACCCTCTTCTGGCACAG

```
601  ATTGCCAGTCCTCTGTTGCTCTGACGCTATTGATACAGATGGTCAAGAGTTTACCATGATTGATACGGCTGGTATGC  700
     TAACGGTCAGGAGACAACGACCTTGTGAGCACTTGTCTATGTCAAATGTCTACCAGTTCTCAAATGGTACTAATGCCGACCATACG
201  I  A  S  P  V  A  G  T  T  R  D  A  I  D  T  H  F  T  D  T  D  G  Q  E  F  T  M  I  D  T  A  G  M  R  234

701  GTAAGTCTGGTAAGGTTTATGAAATACTTCCAAATACTTTATGACTCTTCATGACCGTTCAGATGTGGTCATCAATGC  800
     CATTCAGACCATTCCAAATACTTTATGACTCTTCATGAGACAGTACGCACGCACGTACCAAGTCTACACCAGAATTACCAGTAGTTACG
235  K  S  G  K  V  Y  E  N  T  E  K  Y  S  V  M  R  A  M  R  A  I  D  R  S  D  V  V  L  M  V  I  N  A  267

801  GGAAGAGGGATTCGTGAATACGACAAGCGTATCGCTGGATTTGCTCATGAAGCTGGTAAAGGGATGATTATCGTGGTCAACAAGTGGGATACGCTTGAA  900
     CCTTCTCCCTAAGCACTTATGCTGTTCGCATAGCGACCTAAACGAGTACTTCGACCATTTCCCTACTAATAGCACCAGTTGTTCACCCTATGCGAACTT
268  E  E  G  I  R  E  Y  D  K  R  I  A  G  F  A  H  E  A  G  K  G  M  I  I  V  V  N  K  W  D  T  L  E  300

901  AAAGATAACCACACTATGAAAAACTGGGAAGAAGATATCCGTGAGCAGTTCCAATACCTGCCTTACGCCACCGATTATCTTTGTATCAGTCTTTAACCAAGC  1000
     TTTCTATTGGTGTGATACTTTTTGACCCTTCTTCTATAGGCACTCGTCAAGGTTATGGACGGAATGCGTGGCTAATAGAAACATAGTCGAAATTGGTTCG
301  K  D  N  H  T  M  K  N  W  E  E  D  I  R  E  Q  F  Q  Y  L  P  Y  A  P  I  I  F  V  S  A  L  T  K  Q  334

1001 AACGTCTCCACAAACTTCCTGAGATGATTAAGCAAGTCAAATACACGTATTCCATCAGCTGTCTTGAACGATGTCATCATGGATGCCAT  1100
     TTGCAGAGGTGTTTGAAGGACTCTACTAATTCGTTCATTTAGTCAAATACGTTTTATGTGCATAAGGTAGTCGACAGAACTTGCTACAGTAGTACCTA
335  R  L  H  K  L  P  E  M  I  K  Q  I  S  E  S  Q  N  T  R  I  P  S  A  V  L  N  D  V  I  M  D  A  I  367

1101 TGCCATCAACCCAACACCGACAGAGACAAAGGAAAAGTCTCAAGATTTCTATGGACCCAAGTGGCAACCAAACCACCAAC  1181  (SEQ ID NO: 1)
     ACGGTAGTTGGGTTGTGGCTGTCTCTGTTTCCTTTGCAGAGTTCTAAAGATACGCTGGGTTCACCGTTGGTTGGTTGTGGTTG        (SEQ ID NO: 3)
368  A  I  N  P  T  P  T  D  K  G  K  R  L  K  I  F  Y  A  T  Q  V  A  T  K  P  P  393            (SEQ ID NO: 2)
```

FIG. 1B

```
  1 AAAGTGAGAAATTATGCCCTACCAACTATTGCCATTGTAGACGTCCCAATGTTGGGAAATCAACCCTTATTAATCGGATCGCTGTGAGCGAATCTCC  100
    TTTCACTCTTTAATACCGGGATGGTTGATAACGGTAACATCCTGCAGGGTTACACCCTTTAGTTGGGATAAATTAGCCTAGCGACCACTCGCTTAGAGG

1                       M  A  L  P  T  I  A  I  V  G  R  .P  N  V  G  K  S  T  L  F  N  R  I  A  G  E  R  I  S   29

101 ATTGTAGAAGATGTCGAAGGAGTGACACGTGACCGTATTTATGCAACGGGTGAGTGGCTCAATCGTTCTTTTAGCATGATTGATACAGGAGGAATTGATG  200
    TAACATCTTCTACAGCTTCCTCACTGTGCACTGGCATAAATACGTTGCCCACTCACCGAGTTAGCACTAGAAAATCGTACTAACATATGTCCTCCTAACTAC

30  I  V  E  D  V  E  G  V  T  R  D  R  I  Y  A  T  G  E  W  L  N  R  S  F  S  M  I  D  T  G  G  I  D  D   63

201 ATGTCGATGCTCCTTTCATGAACAATCAAGCACCAGGCAGAAATTGCCATGGAAGAAGCAGATGTATCGTCTTTGTCGTCCGGTAAGGAAGGAAT  300
    TACAGCTACGAGGAAAGTACCTTGTTAGTTCGTGTGCCGTCTTTAACGTACCTTCTTCGTCTACAATAGCAGAAACAGCACAGGCCATTCCTTCCTTA

64  V  D  A  P  F  M  E  Q  I  K  H  Q  A  E  I  A  M  E  E  A  D  V  I  F  V  V  S  G  K  E  G  I    96

301 TACCGATGCAGAGAATACTGACCCGTAAGCTTTATAGACCAGTTATCCTCGCAGTTAACAAGGTGGACAACCCTGAGATGCGAAATGAT  400
    ATGGCTACGTCGTCTTATGCATGGGCATTCGAAATATTCTGGGTGTTTGGTCAATAGAGGCGTCAATTGTTCCACCGTGGGACTCTACGCTTTACTA

97  T  D  A  D  E  Y  V  A  R  K  L  Y  K  T  H  K  P  V  I  L  A  V  N  K  V  D  N  P  E  M  R  N  D   129

401 ATCTATGATTTCTATGCCCTCGGTTTGGGTGAACCACTCGCTCATCTCTCCATGGTATCGGTACAGGGATGTACTAGATGCGATTGTGAAAACC  500
    TAGATACTAAAGATACGGGAGCCAAACCCACTTGGTGAGCGAGTAGAGACAGGTACCATAGCCATGTCCCTACACTGATCTACGCTAACACCTTTGG

130  I  Y  D  F  Y  A  L  G  L  G  E  P  L  P  I  S  S  V  H  G  I  G  T  G  D  V  L  D  A  I  V  E  N  L   163

501 TTCCAAATGAATATGAAGAAGAAAATCCAGATGTCATTAAGTTTAGCTTGATTGGTCGTCCTAACGTTGGAAAATCAAGCTTGATTAATGCTATCTTGGG  600
    AAGGTTTACTTATACTTCTTCTTTTAGGTCTACAGTAATTCAAATGAACTAACCAGCAGGATTGCAACCTTTAGTTCGAACTAATTACGATAGAACCC

164  P  N  E  Y  E  E  E  N  P  D  V  I  K  F  S  L  I  G  R  P  N  V  G  K  S  S  L  I  N  A  I  L  G   196

601 AGAAGACCGTGTCATTGCCAGTCCTGTTGCTGGAACAACTCGTGACGCTATTGATACCCACTTTACAGATACAGATGGTCAAGAGTTTACCATGATTGAT  700
    TCTTCTGGCACAGTAACGGTCAGGACAACGACCTTGTTGAGCACTAGTGAAATGTCTATGTCTACCAGTTCTCAAATGGTACTAACTA

197  E  D  R  V  I  A  S  P  V  A  G  T  T  R  D  A  I  D  T  H  F  T  D  T  D  G  Q  E  F  T  M  I  D   229

701 ACGGCTGGTATGCGTAAGTCTGGTAAGGTTTATGAAAATACTGAAAAGTACTCTGTCATGCGTGCCATGCGTGCTATTGACCGTTCAGATGTGTCTTAA  800
    TGCCGACCATACGCATTCAGACCATTCCAAATACTTTTATGACTTCTTCATGAGACAGTACGCACCGGATAACTGGCAAGTCTACACCAGAATT

```
801  TGGTCATCAATGCGGAAGAGGGATTCGTGAATACGACAAGCTATCGCTGATTTGCTCATGAAGCTGGTCAAGGGATGATTATCGTGGTCAACAAGTG   900
     ACCAGTAGTTACGCCTTCTCCCCTAAGCACTTATGCTGTTCGCATAGCGACCTAAACGAGTACTTCGACCATTCCCTACTAATAGCACCAGTTGTTCAC
264       V  I  N  A  E  E  G  I  R  E  Y  D  K  R  R  I  A  G  F  A  H  E  A  G  K  G  M  I  I  V  V  N  K  W       296

901  GGATACGCTTGAAAAGATAACCACACTATGAAAAACTGGGAAGAAGATATCCGTGAGCAGTTCCAATACCTGCCTTACGCACCGATTATCTTTGTATCA  1000
     CCTATGCGAACTTTTCTATTGGTGTGATACTTTTGACCCTTCTTCTATAGGCACTCGTCAAGGTTATGGACGAATGCGTGGCTAATAGAAACATAGT
297       D  T  L  E  K  D  N  H  T  M  K  N  W  E  E  D  I  R  E  Q  F  Q  Y  L  P  Y  A  P  I  I  F  V  S       329

1001 GCTTTAACCAAGCAACGTCTCCACAAACTTCCTGAGATGATTAAGCAAATCAGCGAAAGTCAAAATACACGTATTCCATCAGCTGTCTTGAACGATGTCA  1100
     CGAAATTGGTTCGTTGCAGAGGTGTTTGAAGGACTCTACTAATTCGTTTAGTCGCTTTCAGTTTTATGTGCATAAGGTAGTCGACAGAACTTGCTACGT
330       A  L  T  K  Q  R  L  H  K  L  P  E  M  I  K  Q  I  S  E  S  Q  N  T  R  I  P  S  A  V  L  N  D  V  I       363

1101 TCATGGATGCCATTGCCATCAACCCAACGACAGACAAAGGAAAACGTCTCAAGATTTTCTATGCGACCCAAGTGGCCAACCAAACCACCAACCTTTGT  1200
     AGTACCTACGGTAACGGTAGTTGGGTTGCTGTCTGTTTCCTTTGCAGAGAACGCTGGTTCACCGTTGGTTTGGTGGTTGGAACA
364       M  D  A  I  A  I  N  P  T  D  K  G  K  R  L  K  I  F  Y  A  T  Q  V  A  T  K  P  P  T  F  V       396

1201 CATCTTTGTCAATGAAGAAGAACTCATGCACTTTTCTTACCTGCGTTTCTTGGAAATCAATCCGCAAGGCCTTTGTTTTTGAGGGAACACCGATTCAT  1300
     GTAGAACAGTTACTTCTTCTTGAGTACGTCAAAGAATGGACGCAAAGAACCTTTAGTTAGGCGTTCCGAAACAAAACTCCCTTGTGCCTAAGTA
397       I  F  V  N  E  E  E  L  M  H  F  S  Y  L  R  F  L  E  N  Q  I  R  K  A  F  V  F  E  G  T  P  I  H       429

1301 CTCATCGCAAGAAAACGCAAATAAAAAGTAGAATCTGGAATGACAGTTCCGGATTTTTTTGATATAATAAAATAATAGAAAACGCTATCAAAAGAAGG  1400
     GAGTAGCGTTCTTTTGCGTTTATTTTTCATCTTAGACCTTACTGTCAAGGCCTAAAAAAACTATATATTATTATCTTTTGCGATAGTTTTCTTCCC
430       L  I  A  R  K  K  *                                                                                    437

1401 GGG  1403
     CCC (SEQ ID NO: 4)
                (SEQ ID NO: 6)
                (SEQ ID NO: 5)
```

FIG. 2B

```
  1  ATGGATATTCAATTTTTAGGAACGGGGGCTGTGCAGCCCTCTAAAGCTCGCAACGTTTCAAGTCTCGCCCTGAAACTTTTGGACGAGATTAACGAAGTTT    100
     TACCTATAAGTTAAAAATCCTTGCCCCGACCAGTCGGGAGATTTCGAGCGTTGCAAAGTTCAGAGACTTTGAAAACCTGCTCTAATTGCTTCAAA

1  M  D  I  Q  F  L  G  T  G  A  G  Q  P  S  K  A  R  N  V  S  S  L  A  L  K  L  L  D  E  I  N  E  V  W       34

101  GGCTCTTTGACTGTGGAGAAGGTACGCAAAATCTCTGGAAACCACTGTAAGTCAGTCATTCCAGTCATTGTGGTGCATTGGGTAGACGTACCTCT          200
     CCGAGAAACTGACACCTCTTCCATGCGTTTTAGAGACCTTTGGTGACATTCAGTCAGTAAGGTCAGTAAGGTGTTAAGCGTCAGTCATTCATTTTAGAAATAATGGGTAGACGTACCTCT

35  L  F  D  C  G  E  G  T  Q  N  R  I  L  E  T  T  I  R  P  R  K  V  S  K  I  F  I  T  H  L  H  G  D      67

201  CCACATTTTGGTTGCCAGGTTCCTTCCTTTCTAGCCGTGCCTTCAGCCAATGAGAGCAGAGATTTGAAATCTACGACCTCAAGGAATCAAGTCA             300
     GGTGTAAAACCAACGGTCCAAGGAAAGATCGGCACGGAAAGTCCGGTTACTTCGTCTCTGTCTAAACCTTTAGATGCTGGAGTTCCTTAGTTCAGT

68  H  I  F  G  L  P  G  F  L  S  S  R  A  F  Q  A  N  E  E  Q  T  D  L  E  I  Y  G  P  Q  G  I  K  S      100

301  TTTGTCTTAACCAGCCTTCGTGTGTCAGGTTCTCGTCTGCCCTACCGCATTCATTCCATGAGTTTGACCAAGATTCTCTGGGTAAAATTCTTGAAACCG      400
     AAACAGAATTGGTCGGAAGCACACAGTCCAAGACAGACGGGATGGCGTAAGTAAAGGTACTCAAACTGGTTCTAAGAGACCCATTTTAAGAACTTTGGC

101  F  V  L  T  S  L  R  V  S  G  S  R  L  P  Y  R  I  H  F  H  E  F  D  D  Q  D  S  L  G  K  I  L  E  T  D    134

401  ATAAATTCACTGTGTATGCAGAGGAGCTGGACCACACTATTTTCTGTGTTGGCTATCGTGTCATGCAAAAGGATCTAGAAGGGACGCTGGATGCTGAAAA        500
     TATTTAAGTGACACATACGTCTCCTGACCTGGTGATAAAAGACACAGTACGCTTTCCTAGATCTTCCCTGCGACCTACGACTTTT

```
501  ACTCAAGGCTGCTGGTGTTCCGTTCGGCCCACTTTTGGTAAATCAAAAACGGCCAGGATCTTGTTTGGAAGACGAACTGAAATCAAGGCAGAGAC   600
     TGAGTTCCGACGACCACAAGGCAAGCCGGGTGAAAACCATTTAGTTTTTGCCGGTCCTAGAACAAAACCTTCTGCCTTGACTTTAGTTCCGTCGTCTG
168   L  K  A  A  G  V  P  F  G  P  L  F  G  K  I  K  N  G  Q  D  L  V  L  E  D  G  T  E  I  K  A  A  D   200

601  TATATCTCAGCGCCACGTCCAGGTAAGATTATCACTATTTTAGGAGACACTCGAAAAACGGGTGCCAGTGTGCTCTGGCTGTCTGTAATGCAGATGTCCTAG   700
     ATATAGAGTCGCGGTGCAGGTCCATTCTAATAGTGATAAAATCCTCTGTGAGCTTTTTGCCCACGTCACACGCAGACCGACAATTACGTCTACAGGATC
201   Y  I  S  A  P  R  P  G  K  I  I  T  I  L  G  D  T  R  K  T  G  A  S  V  R  L  A  V  N  A  D  V  L  V   234

701  TTCATGAGTCCACTTATGGCAAGGTGATGAAAAAATTGCTCGTAACCATGGTCACTCAACTAATATGCAAGCTGCACAAGTAGCGGTAGAAGCAGGTGC   800
     AAGTACTCAGGTGAATACCGTTCCCACTACTTTTTAACGAGCATTGGTACCAGTGAGTTGATTATACGTTCGACGTGTTCATCGCCATCTTCGTCCACG
235   H  E  S  T  Y  G  K  G  D  E  K  I  A  R  N  H  G  H  S  T  N  M  Q  A  A  Q  V  A  V  E  A  G  A   267

801  CAAACGCCTCCTACTCAACCATATCAGTGCCGTTCCTCTCAAAAGATATTAGCAACTGCGCCACAATTTTGAAAATGTCCATGTG   900
     GTTTGCGGAGGATGAGTTGGTATAGTCACGGCAAAGGAGAGTTTCTATAATCGTTGAGTTCTTTCTGCGACGGTGTTAAAACTTTTACAGTACAC
268   K  R  L  L  N  H  I  S  A  R  F  L  S  K  D  I  S  K  L  K  K  D  A  A  T  I  F  E  N  V  H  V   300

901  GTCAAAGACTTGGAAGAAGTGGAAATCTAG   930   (SEQ ID NO: 7)
     CAGTTTCTGAACCTTCTTCACCTTTAGATC         (SEQ ID NO: 9)
301   V  K  D  L  E  E  V  E  I  *   309   (SEQ ID NO: 8)
```

FIG. 3B

```
  1  ATGGGTAAACCTGTCGTAGCCATTGTCGGGAGACCAAATGTAGGAGAAAATCCACAATCTTTAACCGGATTGCGGGAGAAAGAATTCAATAGTAGAAGATA   100
     TACCCATTTGGACAGCATCGGTAACAGCCCTCTGGTTTACATCCTTTTTAGAGAAATTGGCCTAACGCCCTCTTTTCTAAAGTTATCATCTCTAT          34
  1   M  G  K  P  V  V  A  I  V  G  R  P  N  V  G  K  S  T  I  F  N  R  I  A  G  E  R  I  S  I  V  E  D  T

101  CCCCTGGCTGTGACAAGGGATCGGATATACAGCTCGGCTGAATTGATGATTTAATTTGATTGATACGGGGCGGTATTGATATCGGTGATGAGCC          200
     GGGGACCGACACTGTTCCCTAGCCTATATGTCGAGCCGACTTAACTACTAAATTAAACTAACTATGCCCGCATAACTATAGCCACTACTCGG          67
 35   P  G  V  T  R  D  R  I  Y  S  S  A  E  W  L  N  Y  D  F  N  L  I  D  T  G  G  I  D  I  G  D  E  P

201  GTTTTAGCGCAGATTCGCCAGCAAGCTGAAATCGCCATGATGAAGCGACGTGATTATTTTATGGTGAACGGCCGTGAAGGCGTGACAGCTGCTGAT          300
     CAAAATCGCGTCTAAGCGGTCGTTCGACTTTAGCGGTACTACTTCGCTGCACTAATAAAAATACCACTTGCCGGCACTTCCGCACTGTCGACGACTA         100
 68   F  L  A  Q  I  R  Q  Q  A  E  I  A  M  D  E  A  D  V  I  I  F  M  V  N  G  R  E  G  V  T  A  A  D

301  GAAGAAGTGGCGAAATTTGTACCGCACAAAAAGCCTGTGTTTTAGCGGTTAATAATAAACTGGATAACACAGAAATGAGAGCGAATATTTATGATTTTT      400
     CTTCTTCACCGCTTTAAACATGGCGTGTTTTTCGGACACAAATCGCCAATTATTGACCTATTGTGTCTTTACTCTCGCTTATAAATACTAAAAA          134
101   E  E  V  A  K  I  L  Y  R  T  K  K  P  V  V  L  A  V  N  K  L  D  N  T  E  M  R  A  N  I  Y  D  F  Y

401  ATTCGCTAGGCTTTGGCGAGCCGTATCCAATTTCGGGAACACTGGGTGATTACTGGACTCGGACCTGACCACTAAATGACCTACGGCAACGTCTGTAAGG    500
     TAAGCGATCCGAAACCGCTCGGCATAGGTTAAAGCCCTTGTGTCCTGAGCCTGGACTGATTACTGACCTGAGCCGGACTGTTGCATTTTAAAACATTCC       167
135   S  L  G  F  G  E  P  Y  P  I  S  G  T  H  G  L  G  D  L  L  D  A  V  A  E  H  F  K  N  I  P

501  TGAAACGAAATACAATGAAGAAGTTATTCAATTCTGTCTGATCGGACGTCCAAATGTCGGAAAGTCTTCACTTGTGAATGCGATGCTCGGCGAAGAACGC   600
     ACTTTGCTTTATGTTACTTCTTCAATAAGTTAAGACAGACTAGCCTGCAGGTTTACAGCCTTTCAGAAGTGAACACTTACGCTACGAGCCGCTTCTTGCG      200
168   E  T  K  Y  N  E  E  V  I  Q  F  C  L  I  G  R  P  N  V  G  K  S  S  L  V  N  A  M  L  G  E  E  R

601  GTTATTGTCAGCAACGTGGCTGGAACGACAAGAGATGCTGTTGATACGTCATTTACTTACAACCAGCAGAGTTTGTCATTGTCGATACTGCAGGTATGC    700
     CAATAACAGTCGTTGCACCGACCTTGCTGTTCTCTACGACAACTATGCAGTAAGATGAATTGGTCGTCCTCAAACAGTAACAGCTATGACGTCCATACG     234
201   V  I  V  S  N  V  A  G  T  T  R  D  A  V  D  T  S  F  T  Y  N  Q  Q  E  F  V  I  V  D  T  A  G  M  R
```

FIG. 4A

```
701  GAAAAAAGGGAAAGTCTATGAAACGACTGAGAAGTATAGTGTACTGCGGGCGCTAAAAGGCGATTGACCGCTCAGAAGTCGTGGCGGTTGTGCTGGATGG       800
     CTTTTTTCCCTTTCAGATACTTTGCTGACTCTTCATATCACATGACGCCCGCGATTTTCGCTAACTGGCGAGTCTTCAGCACCGCCAACACGACCTACC
235  K  K  G  K  V  Y  E  T  T  E  K  Y  S  V  L  R  A  L  K  A  I  D  R  S  E  V  V  A  V  V  L  D  G        267

801  CGAAGAAGGCATTATTGAACAGGACAAGCGTATCGCCGGTTATGCACACGAAGCGGGCAAGGCCGTCGTCGTTATCGTCGTAAACAAATGGATGCTGTTGAC       900
     GCTTCTTCCGTAATAACTTGTCCTGTTCGCATAGCGCCAATACGTGTGCTTCGCCCGTTCCGGCAGTAGCAGCATTTGTTTACCTACGACAACTG
268  E  E  G  I  I  E  Q  D  K  R  I  A  G  Y  A  H  E  A  G  K  A  V  V  I  V  V  N  K  W  D  A  V  D        300

901  AAAGATGAGAGCACGATGAAAGAATTCGGATCATTTCAATTTCTGGATTATGCGCCAATCCTATTATGTCTGCCTTAACGAAAA                      1000
     TTTCTACTCTCGTGCTACTTTCTTAAGCCTAGTAATACGCGGTTAGGATAAATACAGACGGAATTGCTTTT
301  K  D  E  S  T  M  K  E  F  E  E  N  I  R  D  H  F  Q  F  L  D  Y  A  P  I  L  F  M  S  A  L  T  K  K     334

1001 AACGGATCCATACTCTGATGCCTGCGATTATCAAAGCTAGTGAAATCATTCACTTCGAGTTCAAACAAACGTCTTAAATGATGTCATCATGGACGTGT       1100
     TTGCCTAGGTATGAGACTACGGACGCTAATAGTTTCGATCACTTTTAGTGAAGCTCAAGTTGTTTGCAGAATTTACTACAGTAGTACCTGCGACA
335  R  I  H  T  L  M  P  A  I  I  K  A  S  E  N  H  S  L  R  V  Q  T  N  V  L  N  D  V  I  M  D  A  V        367

1101 GGCAATGAATCGACACCGACTCATAACGGTTCTCGTTTGAAAATTTACTATGCGACTCAAGTGTCGGTAAAGCCGCCAAGCTTCGTTGTTTGTAAAC       1200
     CCGTTACTTAGGCTGTGGCTGAGTATTGCCAAGAGCAAACTTTTAAATGATACGCTGAGTTCACAGCCATTTCGGCGGTTCGAAGCAACAAACATTTG
368  A  M  N  P  T  P  T  H  N  G  S  R  L  K  I  Y  Y  A  T  Q  V  S  V  K  P  P  S  F  V  V  F  V  N        400

1201 GATCCGGAACTGATGCATTTTCATACGAACGGTTTCGGTTTTGAGGGGACACCAATCAAAATATTGCAAGAG                                1300
     CTAGGCCTTGACTACGTAAAAGTATGCTTGCCAAAATCTTTTGGCTTAGTCTGCGCAAACTCCCCGTGTTAGTTTTATAAACGTTCTC
401  D  P  E  L  M  H  F  S  Y  E  R  F  L  E  N  R  I  R  D  A  F  G  F  E  G  T  P  I  K  I  F  A  R  A     434

1301 CTAGAAAATAA     1311      (SEQ ID NO: 10)
     GATCTTTTATT              (SEQ ID NO: 12)
435  R  K  *         436      (SEQ ID NO: 11)
```

FIG. 4B

```
  1  GTGCCGTTGTCTGATGATTTATAAAATGAGGCTTTAAACATGTACCTGTGGTCGCGCTTGTCGCGCCGCCCTAACGTAGAAAATCCACGTTATTAACC  100
     CACGGCAACAGACTACTAAATATTTTACTCCGAAATTTGTACCATGGACACCAGCCGCGAACAGCCCGGGATTGCATCCTTTAGGTGCAATAAATTGG
  1   V  R  C  L  M  I  Y  K  N  E  A  L  N  M  V  P  P  V  V  A  L  V  G  R  P  N  V  G  K  S  T  L  F  N  R      34

101  GTCTAACTCGCACCCGAGATGCGCTGGTTGCGGATTCCCGGGTCTGACTCGTGACCAACGCCTAAGTACGGTCGTGCGGAAATTGAAGGCCGTGAGTTTATCTG  200
     CAGATTGAGCGTGGGCTCTACGCCACCAACGCCTAAGGGCCCAGACTGAGCACTGGCATTCATGCCAGCACGCCTTAACTTCCGGCACTCAAATAGAC
 35   L  T  R  T  R  D  A  L  V  A  D  F  P  P  G  L  T  R  D  R  K  Y  G  R  A  E  I  E  G  R  E  F  I  C      67

201  TATTGATACCGGCGGGATTGATGGCACAGAAGACGGTGTAGAAACCCGATGGCGGAACAGTCGCTGCTGGCGATTGAAGAAGCGGACGTCGTACTGTTT  300
     ATAACTATGGCCGCCCTAACTACCGTGTCTTCTGCCACATCTTTGGGCTACCACATCTTTGGGACGACCGCTAACTTCTTCGCCTGCAGCATGACAAA
 68   I  D  T  G  G  I  D  G  T  E  D  G  V  E  T  R  M  A  E  Q  S  L  L  A  I  E  E  A  D  V  V  L  F     100

301  ATGGTGGATGCGCGCGGGCCTGATGCCGGCAGATGAAGCGATTGCCAAAACATCTGCCTCCCGTGAAAAACCGACCTTCCTGGTGGCAAACAAAACTG  400
     TACCACCTACGCGCGCCCGGACTACGGCCGTCTACTTCGCTAACGGTTTGTAGACGCGTCGCACTTTTTGGCTGAAGGACACCGTTTGTTTTGAC
101   M  V  D  A  R  A  G  L  M  P  A  D  E  A  I  A  K  H  L  R  S  R  E  K  P  T  F  L  V  A  N  K  T  D    134

401  ACGGTCTGGATCCCGATCAGCAGGCAGTGGTTGATTTCTACTCGCTTGGTTTAGGTGAAATCTACCCGATCGCCGCGTCTCACGGTCGTGGCGTATTAAGTCT  500
     TGCCAGACCTAGGGCTAGTCGTCCGTCACCAACTAAGATGAGCGAACCAAATCCACTTTAGGCTTAGAATGGGCTAGCGCGCAGAGTGCCAGCACCGCATAATTCAGA
135   G  L  D  P  D  Q  A  V  V  D  F  Y  S  L  G  L  G  E  I  Y  P  I  A  A  S  H  G  R  G  V  L  S  L     167

501  GCTGGAGCACATGTGCTGCCGTGGATGGAAGATCTCGCACCGCAAGAGAGAAGTCGACGAAGACGCTGAATACTGGGCGCAATTGAAGCGGAAGAGAAC  600
     CGACCTCGTACGACGAGCACCTACCTTCTAGAGCGTGGCGTTCTCGACTTCAGCTGCTTGCGACTTATGACCCGCGTTAAACTTCGCCTTCTCTTG
168   L  E  H  V  L  L  P  W  M  E  D  L  A  P  Q  E  E  V  D  E  D  A  E  Y  W  A  Q  F  E  A  E  E  N     200
```

FIG. 5A

```
601  GGCGAAGAAGAGGAAGACGACTTCGACCCGCAAAGTCTGCCGATCAAACTGGCACTTGTGGGTCGTCCGAACGTAGTAGTCTACACTCACTAACC      700
     CCGCTTCTTCTTCCTTCCTGCTGAAGCTGGGCGTTTCAGACGCTAGTTTGACCGCTAACACCCAGCAGGCTTGCATCCATTCAGATGTGAGTGATTGG
201  G  E  E  E  E  D  D  F  D  P  Q  S  L  P  I  K  L  A  I  V  G  R  P  N  V  G  K  S  T  L  T  N  R       234

701  GTATTCTTGGTGAAGAGCGCGTTGTTGTTTACGACATGCCTGGCACGCCGTGACAGCATCTACATCCAATGAACGCGATGGACGTGAGTATGTGCT      800
     CATAAGAACCACTTCTCGCAACAACAAATGCTGTACGGACCGTGCGGCACTGTCGTAGATGTAGGGTTACCTTGCGCTACCTGCACTCATACACGA
235  I  L  G  E  E  R  V  V  V  Y  D  M  P  G  T  T  R  D  S  I  Y  I  P  M  E  R  D  G  R  E  Y  V  L       267

801  CATTGACACCGCTGGCGTACGTAAACGCGGCAAAATCACCGATGCTGTAGAGAAATTCTCCGTAATCAAAACGTTGCAGGCCATTGAAGACGCCAACGTG  900
     GTAACTGTGGCGACCGCATGCATTGCGCCGTTTTAGTGGCTACGACATCTCTTTAAGAGGCATTAGTTTTGCAACGTCCGGTAACTTCTGCGGTTGCAC
268  I  D  T  A  G  V  R  K  R  G  K  I  T  D  A  V  E  K  F  S  V  I  K  T  L  Q  A  I  E  D  A  N  V       300

901  GTGATGTTAGTGATTGATGCGCGCGAAGTATTCCGATCAGGAGATCTCTCGCTGCTGGGCTTTATTCTCAATAGTGGGCGCTCACTTGTCATTGTGTGA   1000
     CACTACAATCACTAACTACGCGCGCTTCATAAGGCTAGTCCTAGAGAGCGACGACCCGAATAAGAGTTATCACCCGAGTGAACAGTAACACCACT
301  V  M  L  V  I  D  A  R  E  G  I  S  D  Q  D  L  S  L  L  G  F  I  L  N  S  G  R  S  L  V  I  V  N       334

1001 ATAAGTGGGATGCCTGAGTCAGGAAGTCAGGAAGTCAGGAAAGAGCAGGTGAAAGAAACGCTGAAAGACTTCCGTCGTGGGCTTTATCGATTTTGCTCGTGTGCACTTTATCTC  1100
     TATTCACCCTACGGACTCAGTCCTTCAGTCCTTCAGTCCTTTCTCGTCCACTTTCTTTGCGACTCGAAGGCAGACCCGAAATAGCTAAAACGACACACGTGAAATAGAG
335  K  W  D  G  L  S  Q  E  V  K  E  Q  V  K  E  T  L  D  F  R  L  G  F  I  D  F  A  R  V  H  F  I  S       367

1101 TGCCTTGCACGGCAGTGGTGTTGTGGTAACTTGTTTGAATCAGTAGTGAAGCGTATGACGTGAAGCGTATGACAGCTTCCACCCGTGTGTGGGACCTCTATGCTGACGCGCATC     1200
     ACGGAACGTGCCGTCACCACAATGGTTGTTAACAAACTTAGTCACTTCGACATCGTGAGGTGGGCAGCACACCCCTGGAGATACGACTGCGCGTAG
368  A  L  H  G  S  G  V  G  N  L  F  E  S  V  R  E  A  Y  D  S  S  T  R  R  V  G  T  S  M  L  T  R  I       400
```

FIG. 5B

1201 ATGACGATGGCTGTTGAAGATCACCAACCGCCGCTGGTCGTGTGAAGCTGGTCGTGTGAAGCTGAAATATGCCCACGCCGGTGGTTATAACCCGCCGATTGTGG 1300
     TACTGCTACCGACAACTTCTAGTGGTTGGCGGCGACCATGCGGCCAGCAGCACACTTCGACTTTATACGGGTGGCGCCACCAATATTGGGCGGCTAACACC
401  M  T  M  A  V  E  D  H  Q  P  P  L  V  R  G  R  R  R  V  K  L  K  Y  A  H  A  G  G  Y  N  P  P  I  V  V 434

1301 TGATTCACGGTAATCAGGTGAAAGACCTGCCTGATTCCTACAAGCGCTACTTCCGCAAATCGCTGGACGTAATGGGATCGCCGATTCG 1400
     ACTAAGTGCCATTAGTCCACTTTCTGGACGGACTAAGGATGTTCGCGATGAAGGCGTTTAGCGACCTGCATTACCCTAGCGGCTAAGC
435  I  H  G  N  Q  V  K  D  L  P  D  S  Y  K  R  Y  L  M  N  Y  F  R  K  S  L  D  V  M  G  S  P  I  R 467

1401 TATTCAGTTCAAAGAAGGGGAAAACCCGTATGCGAATAAGCGTAAACACCCTGACGCCAACCCAGATGCGTAAACGTAAGCGTCTGATGAAGCACATCAAG 1500
     ATAAGTCAAGTTTCTTCCCCTTTTGGGCATAGCTTATTCGCATTGTGGGACTGCGGTTGGGTCTACGCATTGCATTCGCAGACTACTTCGTGTAGTTC
468  I  Q  F  K  E  G  E  N  P  Y  A  N  K  R  N  T  L  T  P  T  Q  M  R  K  R  K  R  L  M  K  H  I  K 500

1501 AAAAATAAATAA   1512   (SEQ ID NO: 13)
     TTTTTATTTATT          (SEQ ID NO: 15)
501  K  N  K  *    503   (SEQ ID NO: 14)

FIG. 5C

```
  1  GTGGAATTACTTTTTTTAGGGACGGAGAGCCGCATCCCGCCAAGGCGAGAAATGTAACGTCGGTGTGCATTAAAATTGCTTGAAGAAAGGCGTTCGGTAT  100
     CACCTTAATGAAAAAAATCCCTGCCTCGGCCGTAGGGCGGTTCCGCTTCCACATTGCAGCCACCGTAATTTAACGAACTTCTTTCCGCAAGCCATA        34
  1                                      (M) E  L  L  F  L  G  T  G  A  G  I  P  A  K  A  R  N  V  T  S    V  A  L  K  L  L  E  E  R  R  S  V  W

101  GGCTTTTTGACTGCGGGGAAGCCACACAGCATCAAATTTACATACAACGATTAAACCTGTAAAATAGAGAAAAATCTTTATTACACACATGCACGGCGA  200
     CCGAAAAACTGACGCCCCTTCGGTGTGTCGTAGTTTAAATGTATGTTGCTAATTTGGAGCATTTAAATCTCTTTTAGAAATAATGTGTACGTGCCGCT        67
 35   L  F  D  C  G  E  A  T  Q  H  Q  I  L  H  T  T  I  K  P  R  K  I  E  K  I  F  I  T  H  M  H  G  D

201  TCATGTATACGGACTTCCGGGCTTCTGGGGCTTGGGGAGCCGTTCCTTCAAGGCGGAGAGCGAGCTGACAGTGTACGGACCTAAAGGGATCAAGGCGTTTATT  300
     AGTACATATGCCTGAAGGCCCGAAGACCCCTCGGCAAGAAAGTTCCGCCTCTCCGCTCGACTGTCACATGCCTAGTTTCCGATTCCCTAGTTCCGCAAATAA       100
 68   H  V  Y  G  L  P  G  L  L  G  S  R  S  F  Q  G  G  E  D  E  L  T  V  Y  G  P  K  G  I  K  A  F  I

301  GAAACAAGCCTTGCCGTCACGAAAACCATTTGACATATCCGCTTGCAGGAGACGATCAGTTTATTGTCA  400
     CTTTGTTCGGAACGGCAGTGCTTTGGGTAAACTGTATAGGCGAACGTACTGCTAGTCAAATAACAGT        134
101   E  T  S  L  A  V  T  K  T  H  L  T  Y  P  L  A  I  Q  E  I  E  E  G  I  V  F  E  D  D  Q  F  I  V  T

401  CAGGCGGTATCGTCTGTTATTCATGAGTGGAAGCCTTCGGGTGAAGCCTTCGGGTACCGGTGTGCAGGAGAAAAAGACGTACCGGGTTCCTTGAAGGCTGACGTATTAAAAGAAATGAA  500
     GTCGCCATAGACAATAAGTACCTCACCTTCGGAAGCCCATGGCCACACGTCCTTTTCTGCATGGCCCAAGGAACTTCCGACTGCATAATTTCTTTACTT        167
135   A  V  S  V  I  H  G  V  E  A  F  G  Y  R  V  Q  E  K  D  V  P  G  S  L  K  A  D  V  L  K  E  M  N
```

FIG. 6A

```
501  CATCCCGCCCGACCTGTATATCAGAAATCAAAAAGGGCGAAACGGTAACGCTTGAAGACGGACGAATCATCAATGGAATGATTTTCTGGAGCCTCCT   600
     GTAGGGCGGGCCTGGACATATAGTCTTTAGTTTTTTCCGCTTTGCGAACTTCTGCCTGCTTAGTAGTTACCCTTACTAAAGACCTCGGAGGA
168   I  P  P  G  P  V  Y  Q  K  I  K  K  G  E  T  V  T  L  E  D  G  R  I  I  N  G  N  D  F  L  E  P  P   200

601  AAAAAGGGAAGATCTGTTGTTCTCCGGTGATACGAGAGTAAGTGACAAACTAAAAGAGCTTGCGAGGATTGTGATGTGCTTGTTCATGAAGCAACCT   700
     TTTTTCCCTTCTAGACAACACAAGAGGCCACTATGCTCTCATTCACTGTTTGATTTTCTGAACGCTCCTAACACTACACGAACAAGTACTTCGTTGGA
201   K  K  G  R  S  V  V  F  S  G  D  T  R  V  S  D  K  L  K  E  L  A  R  D  C  D  V  L  V  H  E  A  T  F   234

701  TTGCTAAGGAAGACCGTAAACTTGCTTATGATTATTATCACAGTACAACGGAACAAGCGGCTGTAACAGCGAAAGAAGCAAGAGCGAAGCAGCTCATTTT   800
     AACGATTCCTTCTGGCATTTGAACGAATACTAATAATAGTGTCATGTTCGCTTGTTCGCCGACATTGTCGCTTTCTTCGTTCTCGCTTCTCGTCGAGTAAAA
235   A  K  E  D  R  K  L  A  Y  D  Y  Y  H  S  T  T  E  Q  A  A  V  T  A  K  E  A  R  A  K  Q  L  I  L   267

801  AACCCATATCAGGCGAAGATATCAGGAGAGATGCTTCTTTGGAGCTTCAAAAAGAAGCGGTTGACGTTTCCCAATAGCGTGGCGCATGATTCTTA   900
     TTGGGTATAGTCCGCTTCTATAGTCCCTCTACGAAGAAACCTCGAAGTTTTTCTTCGCCAACTGCAAACCCGCCGTATACTAAAGAAT
268   T  H  I  S  A  R  Y  Q  G  D  A  S  L  E  L  Q  K  E  A  V  D  V  F  P  N  S  V  A  A  Y  D  F  L   300

901  GAGGTAAACGTCCCGCGAGGCTGA                  924     (SEQ ID NO: 16)
     CTCCATTTGCAGGGCGCTCCGACT                          (SEQ ID NO: 18)
301   E  V  N  V  P  R  G  *                   307     (SEQ ID NO: 17)
```

FIG. 6B

```
  1    TTGAAACGTGATGAACTCATGGAATTAATTTTTTTAGGTACTTCAGCCGGTGTGCCAACCCGCACGGCAATGTCAGGCAATATGTCAACCTGCAAC    100
       AACTTTGCACTACTTGAGTACCTTAATTAAAAAAAATCATGAAGTCGGCCACACGTTGGGCGTGGCGTTACAGTGCCGTTATAACGAATTGGACGTTG 1    (M) K  R  D  E  L  M  E  L  I  F  L  G  T  S  A  G  V  P  T  R  T  R  N  V  T  A  I  L  L  N  L  Q  H     34

101    ATCCGACCCAGAGCGGACTTTGGTTGTTGACTGCGGTGAAGGCACCCAGCATCAGTCGCCTTAACCCTGGAAAAACTGGACAAGATTTT    200
       TAGGCTGGGTCTCGCCTGAAACAACAACTGACGCCACTTCCGTGGGTCGTAGTGACGTATGGCGGAATTGGGACCTTTGACCTGTTCTAAAA

35    P  T  Q  S  G  L  W  L  F  D  C  G  E  G  T  Q  H  Q  L  H  T  A  F  N  P  G  K  L  D  K  I  F     67

201    TATCAGTCACCTTCATGGCGATCATCTTTTTGGTTTACCCGGCTTGCTGTGCAGTCGTTCTATGTCAGGCATTATCCAACCCTTAACGATTTATGGTCCG    300
       ATAGTCAGTGGAAGTACCGCTAGTAGAAAAACCAAATGGGCCGAACGACACGTCAGAAGATACAGTCCGTAATAGGTTGGGAATTGCTAAATACCAGGC

68    I  S  H  L  H  G  D  H  L  F  G  L  P  G  L  L  C  S  R  S  M  S  G  I  I  Q  P  L  T  I  Y  G  P    100

301    CAAGGTATCCGTGAATTTGTGGAAACCGCTGCGGCTCATGACGACGATTATCCGCTGGAAATTGTCGAAATTGGCGCTGGCGAAATTCTCG    400
       GTTCCATAGGCACTTAAACACCTTTGGCGACGCACGCCTAATGCTGCTGCTAATAGGCGACCTTTAACAGTTTAACCGACCGCTTAAGAGC

101    Q  G  I  R  E  F  V  E  T  A  L  R  I  S  G  W  T  D  Y  P  L  E  I  V  E  I  G  A  G  E  I  L  D    134

401    ATGATGGCCTGCGCAAAGTAACCGCTTATCCGCTGGAACACCCACTGGAATGTTATGGCTATCGTATTGAAGAACATGATAAACCGGGTGCATTAAATGC    500
       TACTACCGGACGCGTTTCATTGGCGAATAGGCGACCTTGTGGGTGACCTTACATAACCGATAGCATATCTTGTACTATTGGCCCACGTAATTACG

```
501  CCAGGCATTAAAAGCTGCTGGCGTGCCGCCTGGCCCACTGTTTCAGGAATTAAAAGCGGGCAAAACAATCACGCTGGAAGATGGAAGGCAGATTAACGGC
     GGTCCGTAATTTTCGACGACGCACGGCGGACCGGGTGACAAAGTCCTTAATTTTCGCCCGTTTGTTAGTGCGACCTTCTACCTTCCGTCTAATTGCCG          600
168  Q   A   L   K   A   A   G   V   P   P   G   P   L   F   Q   E   L   K   A   G   K   T   I   T   L   E   D   G   R   Q   I   N   G           200

601  GCAGATTACTTAGCTGCTCCAGTGCCAGGTAAAGCGCTCGCTATTTTCGGCGATACCGGCCCCTGCGATGCCGACTTGACCTGGCTAAAGGTGTCGATG
     CGTCTAATGAATCGACGAGGTCACGGTCCATTTCGCGAGCGATAAAAGCCGCTATGGCCGGGGACGCTACGGCTGAACTGGACCGATTTCCACAGCTAC          700
201  A   D   Y   L   A   A   P   V   P   G   K   A   L   A   I   F   G   D   T   G   P   C   D   A   A   L   D   L   A   K   G   V   D   V        234

701  TCATGGTGCACGAAGCGACGCTGGATATAACCATGGAAGCCAAAGCCAATAGTCGCGGCCATAGCTCTACACGCCAGGCTGCGACTAGCCCTGAGGC
     AGTACCACGTGCTTCGCTGCGACCTATATTGGTACCTTCGGTTTCGGTTATCAGCGCCGTATCGAGATGTGCGGTCCGACGCTGATCGGGCACTCCG            800
235  M   V   H   E   A   T   L   D   I   T   M   E   A   K   A   N   S   R   G   H   S   S   T   R   Q   A   A   T   L   A   R   E   A           267

801  TGGAGTCGGCAAGCTAATCATTACCCACGTCAGCTCGCGCTATGATGACAAAGGTTGTCAGCATCTTCAATTTTCCCGGCGACT
     ACCTCAGCCGTTCGATTAGTAATGGGTGCAGTCGAGCGCGATACTACTGTTTCCAACAGTCGTGGACAATGCACTTACGCCGCTGA                       900
268  G   V   G   K   L   I   I   T   H   V   S   S   R   Y   D   D   K   G   C   Q   H   L   R   E   C   R   S   I   F   P   A   T               300

901  GAACTGGCGAATGATTCACCGTGTTTAACGTTTAA              936        (SEQ ID NO: 19)
     CTTGACCGCTTACTAAAGTGGCACAAATTGCAAATT                        (SEQ ID NO: 21)
301  E   L   A   N   D   F   T   V   F   N   V   *              311        (SEQ ID NO: 20)
```

FIG. 7B

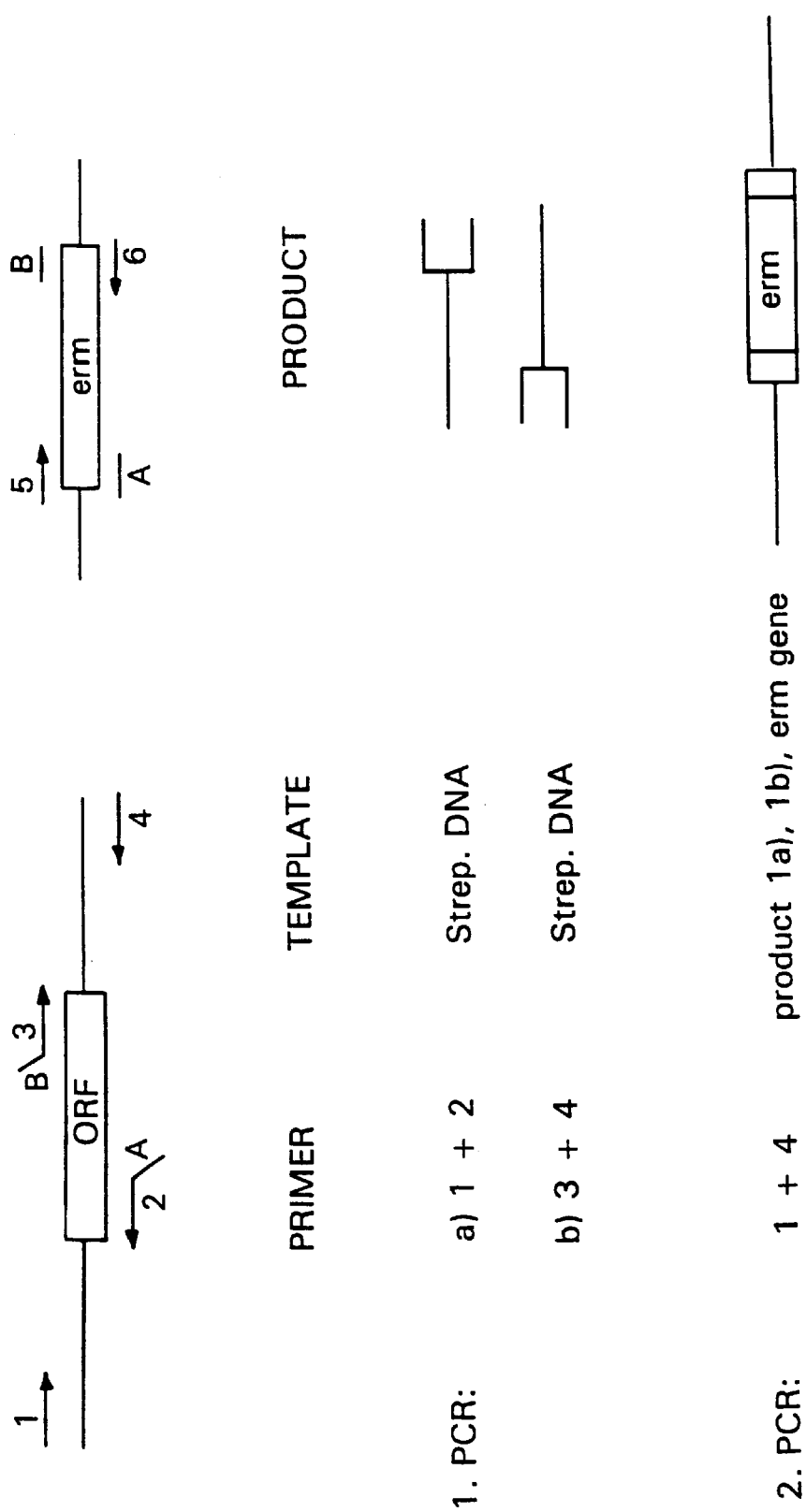

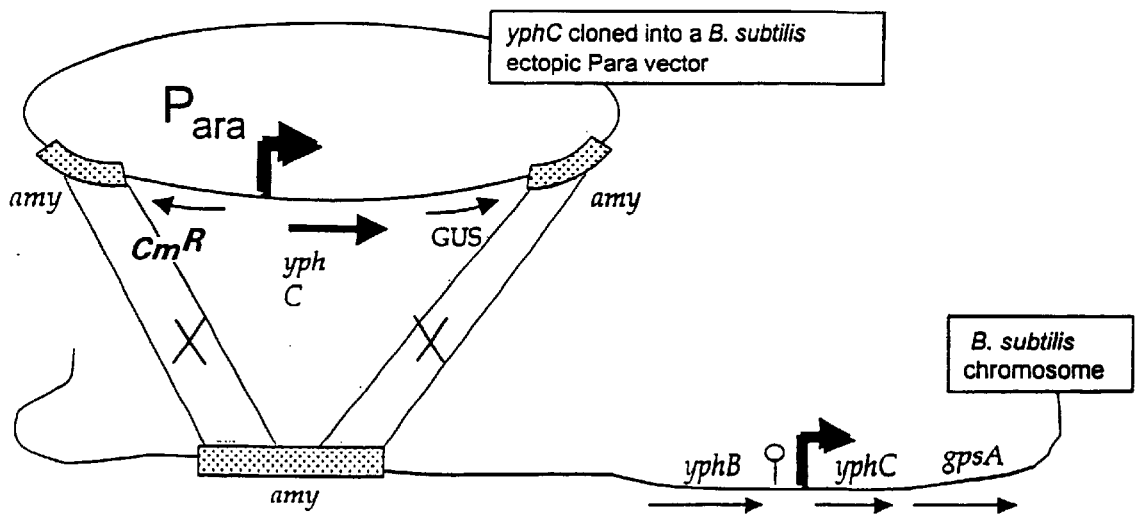
FIG. 11A
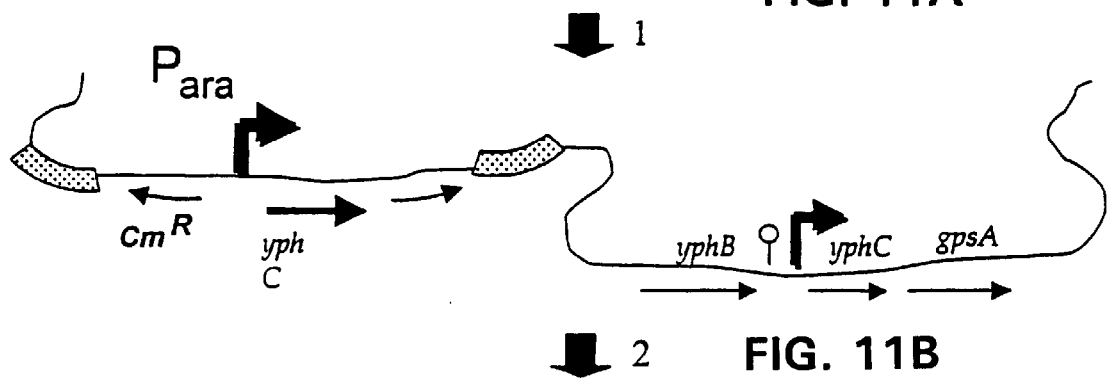
FIG. 11B
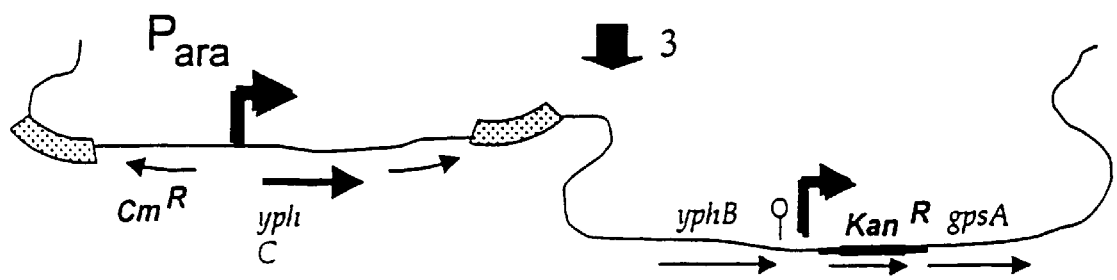
FIG. 11C

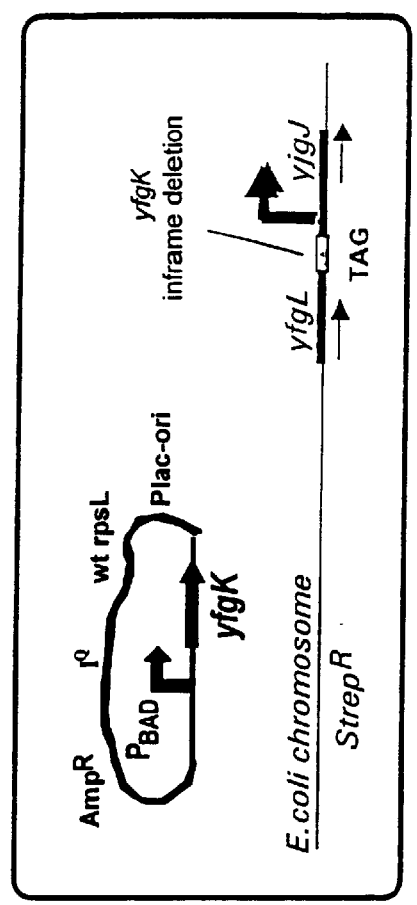
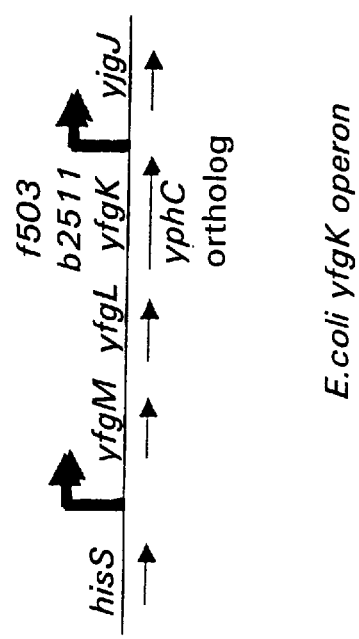
FIG. 12

ESSENTIAL BACTERIAL GENES AND THEIR USE

CROSS-REFERENCE TO RELATED APPLICATION

This application claims priority under 35 U.S.C. §119(e) from U.S. Ser. No. 60/099,578, filed Sep. 9, 1998, which is incorporated herein by reference in its entirety.

FIELD OF THE INVENTION

The invention relates to essential bacterial genes and their use in identifying antibacterial agents.

BACKGROUND OF THE INVENTION

Bacterial infections may be cutaneous, subcutaneous, or systemic. Opportunistic bacterial infections proliferate, especially in patients afflicted with AIDS or other diseases that compromise the immune system. Most bacteria that are pathogenic to humans are gram positive bacteria. The bacterium *Streptococcus pneumoniae*, for example, typically infects the respiratory tract and can cause lobar pneumonia, as well as meningitis, sinusitis, and other infections.

SUMMARY OF THE INVENTION

The invention is based on the discovery of two genes in the gram positive bacterium *Streptococcus pneumoniae* that are essential for the survival of this and other bacteria. For convenience, these genes, yphC and yqjK, are collectively referred to herein as "essential" genes and the polypeptides that these genes encode are referred to as "essential" polypeptides since *Streptococcus pneumoniae* cells lacking functional yphC or yqjK genes are unable to survive.

The yphC and yqjK genes are useful molecular tools for identifying similar genes in pathogenic microorganisms. The essential polypeptides that these genes encode are useful targets for identifying compounds that are inhibitors of the pathogens in which the essential polypeptides are expressed. Such compounds diminish bacterial growth by inhibiting the activity of an essential protein, or by inhibiting transcription of an essential gene or translation of the mRNA transcribed from the essential gene.

The invention, therefore, features an isolated yphC polypeptide having the amino acid sequence set forth in SEQ ID NO:2, as depicted in FIG. 1, or conservative variations thereof. An isolated nucleic acid encoding yphC also is included within the invention. In addition, the invention includes (a) an isolated nucleic acid having the sequence of SEQ ID NO:1, as depicted in FIGS. 1A–B, or degenerate variants thereof; (b) an isolated nucleic acid having the sequence of SEQ ID NO:1, or degenerate variants thereof, wherein T is replaced by U; (c) nucleic acids complementary to (a) and (b); and (d) fragments of (a), (b), and (c) that are at least 15 base pairs in length and that hybridize under stringent conditions, as described below, to genomic DNA encoding the polypeptide of SEQ ID NO:2. The yphC polypeptide depicted in FIGS. 1A–B is a partial sequence of the full-length polypeptide, which is depicted in FIGS. 2A–2B. The invention also features an isolated yphC polypeptide having the amino acid sequence set forth in SEQ ID NO:5, as depicted in FIGS. 2A–2B, or conservative variations thereof. An isolated nucleic acid encoding full-length yphC also is included within the invention. In addition, the invention includes (a) an isolated nucleic acid having the sequence of SEQ ID NO:4, as depicted in FIGS. 2A–2B, or degenerate variants thereof; (b) an isolated nucleic acid having the sequence of SEQ ID NO:4, or degenerate variants thereof, wherein T is replace by U; and (c) nucleic acids complementary to (a) and (b).

As described above for yphC, the invention includes an isolated nucleic acid encoding yqjK. In addition, the invention includes (a) an isolated nucleic acid having the sequence of SEQ ID NO:7, as depicted in FIGS. 3A–B, or degenerate variants thereof; (b) an isolated nucleic acid having the sequence of SEQ ID NO:7, or degenerate variants thereof, wherein T is replaced by U; (c) nucleic acids complementary to (a) and (b); and (d) fragments of (a), (b), and (c) that are at least 15 base pairs in length and that hybridize under stringent conditions, as described below, to genomic DNA encoding the polypeptide of SEQ ID NO:8. These sequences are summarized in Table 1.

TABLE 1

Essential Nucleic Acids and Polypeptides

| Essential Nucleic Acid or Polypeptide | FIG. NO. | SEQ ID NO. OF AMINO ACID SEQUENCE | SEQ ID NO. OF CODING STRAND | SEQ ID NO. OF NON-CODING STRAND |
|---|---|---|---|---|
| yphC-partial sequence | 1 | 2 | 1 | 3 |
| yphC-full-length | 2A-2B | 5 | 4 | 6 |
| yqjK | 3 | 8 | 7 | 9 |

Identification of these essential genes allows homologs of the essential genes to be found in other strains within the species, and it allows orthologs of the essential genes to be found in other organisms (e.g., Bacillus sp., *H. influenzae*, *H. pylori*, and *E. coli*). While "homologs" are structurally similar genes contained within the Streptococcus species, "orthologs" are functionally equivalent genes from other species, as determined, for example, in a standard complementation assay. Thus, the essential polypeptides can be used not only as a model for identifying similar genes in other Streptococcus strains, but also to identify homologs and orthologs of essential genes in other species (e.g., other gram positive bacteria, particularly those bacteria that are pathogenic to humans, and other bacteria generally). Such orthologs can be identified, for example, in a conventional complementation assay. In addition, or alternatively, such orthologs can be expected to exist in bacteria in the same branch of the phylogenetic tree, as set forth, for example, at ftp://ftp.cme.msu.edu/ pub/RDP/SSU_rRNA/SSU/Prok.phylo. For example, *B. subtilis* is in the *B. subtilis* subgroup of the *B. subtilis* group in the Bacillus-Lactobaccillus-Streptococcus Subdivision of the Gram positive phylum. Likewise, *S. pneumoniae* belong to the Stc. pneumonia subgroup of Streptococci, which also are in the Bacillus-Lactobacillus-Streptococcus subdivision of the Gram positive phylum. *E. coli* belong to the Escherichia Salmonella group of the Enterics and relatives within the Gamma subdivision of the Purple bacteria. Other bacteria within the same phylum (particularly, bacteria within the same subdivision, group, or subgroup) can be expected to contain an ortholog of the yphC and/or yqjK genes described herein.

Examples of orthologs of the Streptococcus yphC and yqjK genes are summarized in Table 2. As shown in Table 2, the Streptococcus gene yphC has an ortholog in *B. subtilis*, termed "B-yphC," and an ortholog in *E. coli*, termed "yfgK," which is also known as "f503." The Streptococcus gene yqjK also has an ortholog in *B. subtilis*, termed "B-yqjK," and an ortholog in *E. coli*, termed "elaC," which is also known as "o311." As discussed below, orthologs of essential genes may themselves be essential or non-essential in the organism in which they are found.

As determined by the experiments described below, the B-yphC, yfgK, and B-yqjK orthologs are essential for survival of the bacteria in which they are found. Thus, these essential orthologous genes and the polypeptides encoded by these orthologs can be used to identify compounds that inhibit the growth of the host organism (e.g., compounds that inhibit the activity of an essential protein, or inhibit transcription of an essential gene).

TABLE 2

Orthologs of yphC and yqjK

| Nucleic Acid or Polypeptide | Ortholog | Figure number of Ortholog | SEQ ID NO. of Amino Acid Sequence of Ortholog | SEQ ID NO. of Nucleic Acid Sequence of Ortholog | SEQ ID NO. of Non-Coding Strand of Ortholog |
|---|---|---|---|---|---|
| yphC | *B. subtilis* B-yphC GenBank Accession No. Z99115 | 4A–4B | 11 | 10 | 12 |
| yphC | *E. coli* yfgK GenBank Accession No. AE000337 | 5A–5B | 14 | 13 | 15 |
| yqjK | *B. subtilis* B-yqjK GenBank Accession No. Z99116 | 6 | 17 | 16 | 18 |
| yqjK | *E. coli* elaC GenBank Accession No. AE000316 | 7 | 20 | 19 | 21 |

The yphC polypeptides and genes described herein include the polypeptides and genes set forth in FIGS. 1A–B and 2A–2B herein, as well as isozymes, variants, and conservative variations of the sequences set forth in FIGS. 1A–B and 2A–2B. The invention includes various isozymes of yphC and yqjK. For example, the invention includes a gene that encodes an essential polypeptide but which gene includes one or more point mutations, deletions, or promoter variants, provided that the resulting essential polypeptide retains a biological function of an essential polypeptide.

The yphC polypeptide has structural characteristics of known GTPases. Using BLAST analysis, the yphC polypeptide has been shown to contain two domains that are predicted to be GTPase domains, and yphC displays GTPase activity in vitro. This GTPase activity is linked to the essentiality of the yphC polypeptide. When point mutations are made in each GTPase domain of yphC such that the mutants are unable to bind GTP, such mutants no longer are able to complement a bacterial strain that lacks yphC. The yqjK polypeptide has structural characteristics of known sulfatases. Thus, the various isozymes, variants, and conservative variations of the yphC and yqjK sequences set forth in FIGS. 1A–B and 2A–2B retain a biological function of yphC or yqjK as determined, for example, in an assay of GTPase or sulfatase activity, or in a conventional complementation assay. Suitable GTPase and sulfatase activity assays are well known in the art (see, e.g., Bollag, et al., Meth. Enzymol. 255:161 (1995) and Barbeyron, et al., Microbiol. 141:2897 (1995), incorporated herein by reference). The GTPase activity of yphC can also be assayed using a conventional Malachite Green phosphorelease assay (see, e.g., Lanzetta et al., 1979, Analytical Biochemistry 100:95–97). The inclusion of KCl in such an assay leads to an approximately 70-fold stimulation of GTPase activity, and thus provides a sensitive assay for detection of GTP activity.

Also encompassed by the term yphC gene are degenerate variants of the nucleic acid sequences set forth in FIGS. 1A–B and 2A–2B (SEQ ID NO:1 and 4). Degenerate variants of a nucleic acid sequence exist because of the degeneracy of the amino acid code; thus, those sequences that vary from the sequence represented by SEQ ID NO:1 and 4, but which nonetheless encode a yphC polypeptide are included within the invention.

Likewise, because of the similarity in the structures of amino acids, conservative variations (as described herein) can be made in the amino acid sequence of the yphC polypeptide while retaining the function of the polypeptide (e.g., as determined in a conventional complementation assay). Other yphC polypeptides and genes identified in additional bacterial strains may be such conservative variations or degenerate variants of the particular yphC polypeptide and nucleic acid set forth in FIGS. 1A–B and 2A–2B (SEQ ID NOs:1–6). The yphC polypeptide and gene share at least 80%, e.g., 90%, sequence identity with SEQ ID NOs:2 and 1, respectively, or SEQ ID NOs: 5 and 4, respectively. Regardless of the percent sequence identity between the yphC sequence and the sequences represented by SEQ ID NOs:1, 2, 4, and 5, the yphC genes and polypeptides encompassed by the invention preferably are able to complement for the lack of yphC function (e.g., in a temperature-sensitive mutant) in a standard complementation assay.

Additional yphC genes that are identified and cloned from additional bacterial strains, and pathogenic, gram-positive strains in particular, can be used to produce yphC polypeptides for use in the various methods described herein, e.g., for identifying antibacterial agents. Likewise, the term yqjK encompasses isozymes, variants, and conservative variations of the sequences depicted in FIGS. 3A–B.

In various embodiments, the essential polypeptide used in the assays described herein is derived from a non-pathogenic or pathogenic gram positive bacterium. For example, the polypeptide can be derived from a Streptococcus strain, such as *Streptococcus pneumoniae*, *Streptococcus pyogenes*, *Streptococcus agalactiae*, *Streptococcus endocarditis*, *Streptococcus faecium*, *Streptococcus sangus*, *Streptococcus viridans*, and *Streptococcus hemolyticus*. Orthologs of the yphC and yqjK genes can be derived from a wide spectrum of bacteria, such as *E. coli* and *Bacillus subtilis*.

Having identified the yphC and yqjK genes described herein as being essential for survival, these essential genes and the polypeptides encoded by these essential genes and their essential homologs and orthologs can be used to identify antibacterial agents. Such antibacterial agents can readily be identified with high throughput assays to detect inhibition of the metabolic pathway in which the essential polypeptide participates. This inhibition can be caused by small molecules interacting with (e.g., binding directly or indirectly to) the essential polypeptide or other essential polypeptides in that pathway.

An exemplary method for identifying antibacterial compounds involves screening for small molecules that specifically interact with (i.e., bind directly or indirectly to) the essential polypeptide. A variety of suitable interaction and binding assays are known in the art as described, for example, in U.S. Pat. Nos. 5,585,277 and 5,679,582, incorporated herein by reference. For example, in various conventional assays, test compounds can be assayed for their ability to interact with an essential polypeptide by measuring the ability of the small molecule to stabilize the essential polypeptide in its folded, rather than unfolded, state. More specifically, the degree of protection from unfolding that is afforded by the test compound can be measured. Test compounds that bind the essential polypeptide with high affinity cause, for example, a large shift in the temperature at which the polypeptide is denatured. Test compounds that stabilize the essential polypeptide in a folded state can be further tested for antibacterial activity in a standard susceptibility assay.

Another exemplary method for identifying antibacterial agents involves measuring the ability of a test compound to bind to one of the essential polypeptides described herein. Binding can be assayed in a conventional capillary electrophoresis assay in which binding of the test compound to the essential polypeptide changes the electrophoretic mobility of the essential polypeptide.

Another suitable method for identifying inhibitors of the essential polypeptides involves identifying a biochemical activity of the essential polypeptide and then screening for small molecule inhibitors of the activity using, for example, a high throughput screening method. The yphC polypeptide has structural characteristics of known GTPases and displays GTPase activity in vitro. Therefore, inhibitors of this polypeptide therefore can be identified by their ability to inhibit the GTPase activity of yphC in a conventional assay of GTPase activity. Suitable assays have been described (e.g., Gollag et al., Meth. Enzymol. 255: 161–170, 1995, which is incorporated herein by reference). A detailed example of a suitable assay is set forth below.

The yqjK polypeptide has structural characteristics of sulfatases and is expected to function as a sulfatase. Accordingly, inhibitors of the yqjK polypeptide can be identified by assaying for the ability of the test compound to inhibit the sulfatase activity of yqjK. An example of a suitable assay is described by Barbeyron et al., Microbiol. 141:2897–2904, 1995, which is incorporated herein by reference.

The invention also includes a method for identifying an antibacterial agent which method entails: (a) contacting an essential polypeptide, or homolog or orthologs thereof, with a test compound; (b) detecting binding of the test compound to the polypeptide or homolog or ortholog; and, optionally, (c) determining whether a test compound that binds to the polypeptide or homolog or ortholog inhibits growth of bacteria, relative to growth of bacteria cultured in the absence of the test compound that binds to the polypeptide or homolog or ortholog, as an indication that the test compound is an antibacterial agent.

In another suitable assay, a promoter that responds to depletion of the essential polypeptide by upregulation or downregulation is linked to a reporter gene. To identify a promoter that is up- or down-regulated by the depletion of an essential protein, the gene encoding the essential protein is deleted from the genome and replaced with a version of the gene in which the sequence encoding the essential protein is operably linked to a regulatable promoter. The cells containing this regulatable genetic construct are kept alive by the essential polypeptide produced from the genetic construct containing the regulatable promoter. However, the regulatable promoter allows the expression of the essential polypeptide to be reduced to a level that causes growth inhibition. Total RNA prepared from bacteria under such growth-limiting conditions is compared with RNA from wild-type cells. Standard methods of transcriptional profiling can be used to identify mRNA species that are either more or less abundant (i.e., up- or down-regulated) when expressed under the limiting conditions. Genomic sequence information, e.g., from GenBank, can be used to identify the promoter that drives expression of the identified RNA species. Such promoters are up- or down-regulated by depletion of the essential polypeptide.

Having identified a promoter(s) that is up- or down-regulated by depletion of the essential polypeptide, the promoter(s) is operably linked to a reporter gene (e.g., β-galactosidase, gus, or green fluorescent protein (GFP)). A bacterial strain containing this reporter gene construct is then exposed to test compounds. Compounds that inhibit the essential polypeptide (or other polypeptides in the essential pathway in which the essential polypeptide participates) cause a functional depletion of the essential polypeptide and therefore lead to an upregulation or downregulation of expression the reporter gene. Compounds that inhibit the essential polypeptides in such an assay are expected to be antibacterial and can be further tested, if desired, in standard susceptibility assays.

In a related method for identifying antibacterial compounds, the essential polypeptides are used to isolate peptide or nucleic acid ligands that specifically bind the essential polypeptides. These peptide or nucleic acid ligands are then used in a displacement screen to identify small molecules that interact with the essential polypeptide. Such assays can be carried out essentially as described above.

In still another method, interaction of a test compound with an essential polypeptide (i.e., direct or indirect binding) can be detected in a conventional two-hybrid system for detecting protein/protein interactions (e.g., in yeast or mammalian cells). A test compound found to interact with the essential polypeptide can be further tested for antibacterial activity in a conventional susceptibility assay. Generally, in such two-hybrid methods, (a) the essential polypeptide is provided as a fusion protein that includes the polypeptide fused to (i) a transcription activation domain of a transcription factor or (ii) a DNA-binding domain of a transcription factor; (b) the test polypeptide is provided as a fusion protein that includes the test polypeptide fused to (i) a transcription activation domain of a transcription factor or (ii) a DNA-binding domain of a transcription factor; and (c) binding of the test polypeptide to the polypeptide is detected as a reconstitution of a transcription factor. Homologs and orthologs of the essential polypeptides can be used in similar methods. Reconstitution of the transcription factor can be detected, for example, by detecting transcription of a gene that is operably linked to a DNA sequence bound by the DNA-binding domain of the. reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated nucleic acid molecule encoding an essential polypeptide is used to identify a compound that decreases the expression of an essential polypeptide in vivo. Such compounds can be used as antibacterial agents. To identify such compounds, cells that express an essential polypeptide are cultured, exposed to a test compound (or a mixture of test compounds), and the level of expression or activity is compared with the level of essential polypeptide expression or activity in cells that are otherwise identical but that have not been exposed to the test compound(s). Many standard quantitative assays of gene expression can be utilized in this aspect of the invention.

To identify compounds that modulate expression of an essential polypeptide (or homologous or orthologous sequence), the test compound(s) can be added at varying concentrations to the culture medium of cells that express an essential polypeptide (or homolog or ortholog), as described herein. Such test compounds can include small molecules (typically, non-protein, non-polysaccharide chemical entities), polypeptides, and nucleic acids. The expression of the essential polypeptide is then measured, for example, by Northern blot PCR analysis or RNAse protection analyses using a nucleic acid molecule of the invention as a probe. The level of expression in the presence of the test molecule, compared with the level of expression in its absence, will indicate whether or not the test molecule alters the expression of the essential polypeptide. Because the yphC and yqjK polypeptides are essential for survival, test compounds that inhibit the expression and/or function of the essential polypeptide, or of an essential homolog or ortholog thereof, will inhibit growth of, or kill, the cells that express such polypeptides.

The polypeptides encoded by essential genes also can be used, separately or together, in assays to identify test compounds that interact with these polypeptides. Test compounds that interact with these polypeptides then can readily be tested, in conventional assays, for their ability to inhibit bacterial growth. Test compounds that interact with the essential polypeptides are candidate antibacterial agents, in contrast to compounds that do not interact with the essential polypeptides. As described herein, any of a variety of art-known methods can be used to assay for the interaction of test compounds with the essential polypeptides.

Typically, the test compound will be a small organic molecule. Alternatively, the test compound can be a test polypeptide (e.g., a polypeptide having a random or predetermined amino acid sequence; or a naturally-occurring or synthetic polypeptide) or a nucleic acid, such as a DNA or RNA molecule. The test compound can be a naturally-occurring compound or it can be synthetically produced, if desired. Synthetic libraries, chemical libraries, and the like can be screened to identify compounds that bind the essential polypeptide. More generally, binding of test a compound to the polypeptide, homolog, or ortholog can be detected either in vitro or in vivo. If desired, the above-described methods for identifying compounds that modulate the expression of the polypeptides of the invention can be combined with measuring the levels of the essential polypeptides expressed in the cells, e.g., by performing a Western blot analysis using antibodies that bind an essential polypeptide.

Regardless of the source of the test compound, the essential polypeptides described herein can be used to identify compounds that inhibit the activity of an essential protein or transcription of an essential gene or translation of the mRNA transcribed from the essential gene. These antibacterial agents can be used to inhibit a wide spectrum of pathogenic or non-pathogenic bacterial strains.

In other embodiments, the invention includes pharmaceutical formulations that include a pharmaceutically acceptable excipient and an antibacterial agent identified using the methods described herein. In particular, the invention includes pharmaceutical formulations that contain antibacterial agents that inhibit the growth of, or kill, pathogenic bacterial strains (e.g., pathogenic gram positive bacterial strains such as pathogenic Streptococcus strains). Such pharmaceutical formulations can be used in a method of treating a bacterial infection in an organism (e.g., a Streptococcus infection). Such a method entails administering to the organism a therapeutically effective amount of the pharmaceutical formulation, i.e., an amount sufficient to ameliorate signs and/or symptoms of the bacterial infection. In particular, such pharmaceutical formulations can be used to treat bacterial infections in mammals such as humans and domesticated mammals (e.g., cows, pigs, dogs, and cats), and in plants. The efficacy of such antibacterial agents in humans can be estimated in an animal model system well known to those of skill in the art (e.g., mouse and rabbit model systems of, for example, streptococcal pneumonia).

Various affinity reagents that are permeable to the microbial membrane (i.e., antibodies and antibody fragments) are useful in practicing the methods of the invention. For example polyclonal and monoclonal antibodies that specifically bind to the yphC polypeptide or yqjK polypeptide can facilitate detection of essential polypeptides in various bacterial strains (or extracts thereof). These antibodies also are useful for detecting binding of a test compound to essential polypeptides (e.g., using the assays described herein). In addition, monoclonal antibodies that bind essential polypeptides can themselves be used as antibacterial agents.

The invention further features methods of identifying from a large group of mutants those strains that have conditional lethal mutations. In general, the gene and corresponding gene product are subsequently identified, although the strains themselves can be used in screening or diagnostic assays. The mechanism(s) of action for the identified genes and gene products provide a rational basis for the design of antibacterial therapeutic agents. These antibacterial agents reduce the action of the gene product in a wild type strain, and therefore are useful in treating a subject with that type, or a similarly susceptible type, of infection by administering the agent to the subject in a pharmaceutically effective amount. Reduction in the action of the gene product includes competitive inhibition of the gene product for the active site of an enzyme or receptor; non-competitive inhibition; disrupting an intracellular cascade path which requires the gene product; binding to the gene product itself, before or after post-translational processing; and acting as a gene product mimetic, thereby down-regulating the activity. Therapeutic agents include monoclonal antibodies raised against the gene product.

Furthermore, the presence of the gene sequence in certain cells (e.g., a pathogenic bacterium of the same genus or similar species), and the absence or divergence of the sequence in host cells can be determined, if desired. Therapeutic agents directed toward genes or gene products that are not present in the host have several advantages, including fewer side effects, and a lower overall required dosage.

Nucleic acids include both RNA and DNA, including genomic DNA and synthetic (e.g., chemically synthesized) DNA. Nucleic acids can be double-stranded or single-stranded. Where single-stranded, the nucleic acid may be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An isolated nucleic acid is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

A nucleic acid sequence that is substantially identical to an essential nucleotide sequence is at least 80% (e.g., at least 85%) identical to the nucleotide sequence of yphC or yqjK as represented by the SEQ ID NOs listed in Table 1, as depicted in FIGS. 1A–3B. For purposes of comparison of nucleic acids, the length of the reference nucleic acid sequence will generally be at least 40 nucleotides, e.g., at least 60 nucleotides or more nucleotides.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, the molecules are identical at that position. The percent identity between the two sequences is a function of the number of identical positions shared by the sequences (i.e., % identity=# of identical positions/total # of overlapping positions×100). Preferably, the two sequences are the same length.

The determination of percent identity or homology between two sequences can be accomplished using a mathematical algorithm. A suitable, mathematical algorithm utilized for the comparison of two sequences is the algorithm of Karlin and Altschul (1990) *Proc. Nat'l Acad. Sci. USA* 87:2264–2268, modified as in Karlin and Altschul (1993) *Proc. Nat'l Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to yphC or yqjK nucleic acid molecules of the invention. BLAST protein searches can be performed with the XBLAST program, score=50, wordlength=3 to obtain amino acid sequences homologous to yphC or yqjK protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using the techniques described above, with or without allowing gaps. In calculating percent identity, only exact matches are counted.

The essential polypeptides useful in practicing the invention include, but are not limited to, recombinant polypeptides and natural polypeptides. Also useful in the invention are nucleic acid sequences that encode forms of essential polypeptides in which naturally occurring amino acid sequences are altered or deleted. Preferred nucleic acids encode polypeptides that are soluble under normal physiological conditions. Also within the invention are nucleic acids encoding fusion proteins in which a portion of an essential polypeptide is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. The invention also includes, for example, isolated polypeptides (and the nucleic acids that encode these polypeptides) that include a first portion and a second portion; the first portion includes an essential polypeptide, and the second portion includes an immunoglobulin constant (Fc) region or a detectable marker.

The fusion partner can be, for example, a polypeptide which facilitates secretion, e.g., a secretory sequence. Such a fused polypeptide is typically referred to as a preprotein. The secretory sequence can be cleaved by the host cell to form the mature protein. Also within the invention are nucleic acids that encode an essential polypeptide fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequences represented by SEQ ID NO:1 or 7, or their complements. The hybridizing portion of the hybridizing nucleic acids is typically at least 15 (e.g., 20, 25, 30, or 50) nucleotides in length. The hybridizing portion of the hybridizing nucleic acid is at least 80%, e.g., at least 95%, or at least 98%, identical to the sequence of a portion or all of a nucleic acid encoding an essential polypeptide or its complement. Hybridizing nucleic acids of the type described herein can be used, for example, as a cloning probe, a primer (e.g., a PCR primer), or a diagnostic probe. Nucleic acids that hybridize to the nucleotide sequences represented by SEQ ID NOs: 1 and 7 are considered "antisense oligonucleotides."

Also part of in the invention are various engineered cells, e.g., transformed host cells, that contain an essential nucleic acid described herein. A transformed cell is a cell into which (or into an ancestor of which) has been introduced, by means of recombinant DNA techniques, a nucleic acid encoding an essential polypeptide. Both prokaryotic and eukaryotic cells are included, e.g., bacteria, such as Streptococcus, Bacillus, and the like.

Also within the invention are genetic constructs (e.g., vectors and plasmids) that include a nucleic acid of the invention that is operably linked to a transcription and/or translation sequence to enable expression, e.g., expression vectors. A selected nucleic acid, e.g., a DNA molecule encoding an essential polypeptide, is "operably linked" to a transcription and/or translation sequence when it is positioned adjacent to one or more sequence elements, e.g., a promoter, which direct transcription and/or translation of the sequence such that the sequence elements can control transcription and/or translation of the selected nucleic acid.

The invention also features purified or isolated polypeptides encoded by the essential genes yphC and yqjK. The terms "protein" and "polypeptide" both refer to any chain of amino acids, regardless of length or post-translational modification (e.g., glycosylation or phosphorylation). Thus, the terms yphC polypeptide and yqjK polypeptide include full-length, naturally occurring, isolated yphC and yqjK proteins, respectively, as well as recombinantly or synthetically produced polypeptides that correspond to the full-length, naturally occurring proteins, or to a portion of the naturally occurring or synthetic polypeptide (provided that a portion of the yphC polypeptide includes a portion of the sequence depicted in FIGS. 1A–B).

A purified or isolated compound is a composition that is at least 60% by weight the compound of interest, e.g., an essential polypeptide or antibody. Preferably the preparation is at least 75% (e.g., at least 90%, 95%, or even 99%) by weight the compound of interest. Purity can be measured by any appropriate standard method, e.g., column chromatography, polyacrylamide gel electrophoresis, or HPLC analysis.

Preferred essential polypeptides include a sequence substantially identical to all or a portion of a naturally occurring essential polypeptide, e.g., including all or a portion of the sequences shown in FIGS. 1A–B, 2A–2B, and 3A–B (provided that a portion of the yphC polypeptide includes a portion of the sequence depicted in FIGS. 1A–B). Polypeptides "substantially identical" to the essential polypeptide sequences described herein have an amino acid sequence that is at least 80% identical to the amino acid sequence of the essential polypeptides represented by the SEQ ID NOs listed in Table 1 (measured as described herein). The new polypeptides can also have a greater percentage identity, e.g., 85%, 90%, 95%, or even higher. For purposes of comparison, the length of the reference essential polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. Alternatively, it can be a 100 amino acid long polypeptide that is 50% identical to the reference polypeptide over its entire length. Of course, other polypeptides also will meet the same criteria.

The invention also features purified or isolated antibodies that specifically bind to an essential polypeptide. An antibody "specifically binds" to a particular antigen, e.g., an essential polypeptide, when it binds to that antigen, but does not substantially recognize and bind to other molecules in a sample, e.g., a biological sample, that naturally includes an essential polypeptide.

In another aspect, the invention features a method for detecting an essential polypeptide in a sample. This method includes: obtaining a sample suspected of containing an essential polypeptide; contacting the sample with an antibody that specifically binds to an essential polypeptide under conditions that allow the formation of complexes of an antibody and the essential polypeptide; and detecting the complexes, if any, as an indication of the presence of an essential polypeptide in the sample.

Also encompassed by the invention is a method of obtaining a gene related to an essential gene. Such a method entails obtaining a labeled probe that includes an isolated nucleic acid which encodes all or a portion of an essential nucleic acid, or a homolog thereof; screening a nucleic acid fragment library with the labeled probe under conditions that allow hybridization of the probe to nucleic acid fragments in the library, thereby forming nucleic acid duplexes; isolating labeled duplexes, if any; and preparing a full-length gene sequence from the nucleic acid fragments in any labeled duplex to obtain a gene related to the essential gene. Alternatively, such related genes can be identified by carrying out a BLAST search of various sequenced bacterial genomes, as described above.

The invention offers several advantages. For example, the methods for identifying antibacterial agents can be configured for high throughput screening of numerous candidate antibacterial agents. Because the essential genes disclosed herein are thought to be highly conserved, antibacterial drugs targeted to these genes or their gene products are expected to have antibacterial activity against a wide range of bacteria.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

Other features and advantages of the invention will be apparent from the following detailed description, and from the claims.

BRIEF DESCRIPTION OF THE DRAWINGS

FIGS. 1A–B are a representation of the amino acid and nucleic acid sequences of the yphC polypeptide and coding and non-coding strands of the yphC gene from a *Streptococcus pneumoniae* strain (SEQ ID NOs:2, 1, and 3, respectively).

FIGS. 2A–2B are a representation of the full-length amino acid and nucleic acid sequences of the yphC polypeptide and coding and non-coding strands of the yphC gene from a *Streptococcus pneumoniae* strain (SEQ ID NOs:5, 4, and 6, respectively).

FIGS. 3A–B are a representation of the amino acid and nucleic acid sequences of the yqjK polypeptide and coding and non-coding strands of the yqjK gene from a *Streptococcus pneumoniae* strain (SEQ ID NOs:8, 7, and 9, respectively).

FIGS. 4A–4B are a representation of the amino acid and nucleic acid sequences of the B-yphC polypeptide and coding and non-coding strands of the B-yphC gene from a *B. subtilis* strain (SEQ ID Nos:11, 10, and 12, respectively).

FIGS. 5A–5C are a representation of the amino acid and nucleic acid sequences of the yfgK polypeptide and coding and non-coding strands of the yfgK gene from an *E. coli* strain (SEQ ID Nos:14, 13, and 15, respectively).

FIGS. 6A–B are a representation of the amino acid and nucleic acid sequences of the B-yqjK polypeptide and coding and non-coding strands of the B-yqjK gene from a *B. subtilis* strain (SEQ ID Nos:17, 16, and 18, respectively).

FIGS. 7A–B are a representation of the amino acid and nucleic acid sequences of the elaC polypeptide and gene from an *E. coli* strain (SEQ ID Nos:20, 19, and 21, respectively).

FIG. 8 is a schematic representation of the PCR strategy used to produce DNA molecules used for targeted deletions of essential genes in *Streptococcus pneumoniae*.

FIGS. 11A–11C are schematic representations of the strategy used to construct conditional null mutants of the yphC and yqjK genes.

FIG. 12 is a schematic representation of the general strategy used to obtain deletions of essential genes in *E. coli* and shows the essential phenotype of the *E. coli* yfgK gene, which is an ortholog of the *S. pneumoniae* yphC gene.

DETAILED DESCRIPTION OF THE INVENTION

Figure 9:
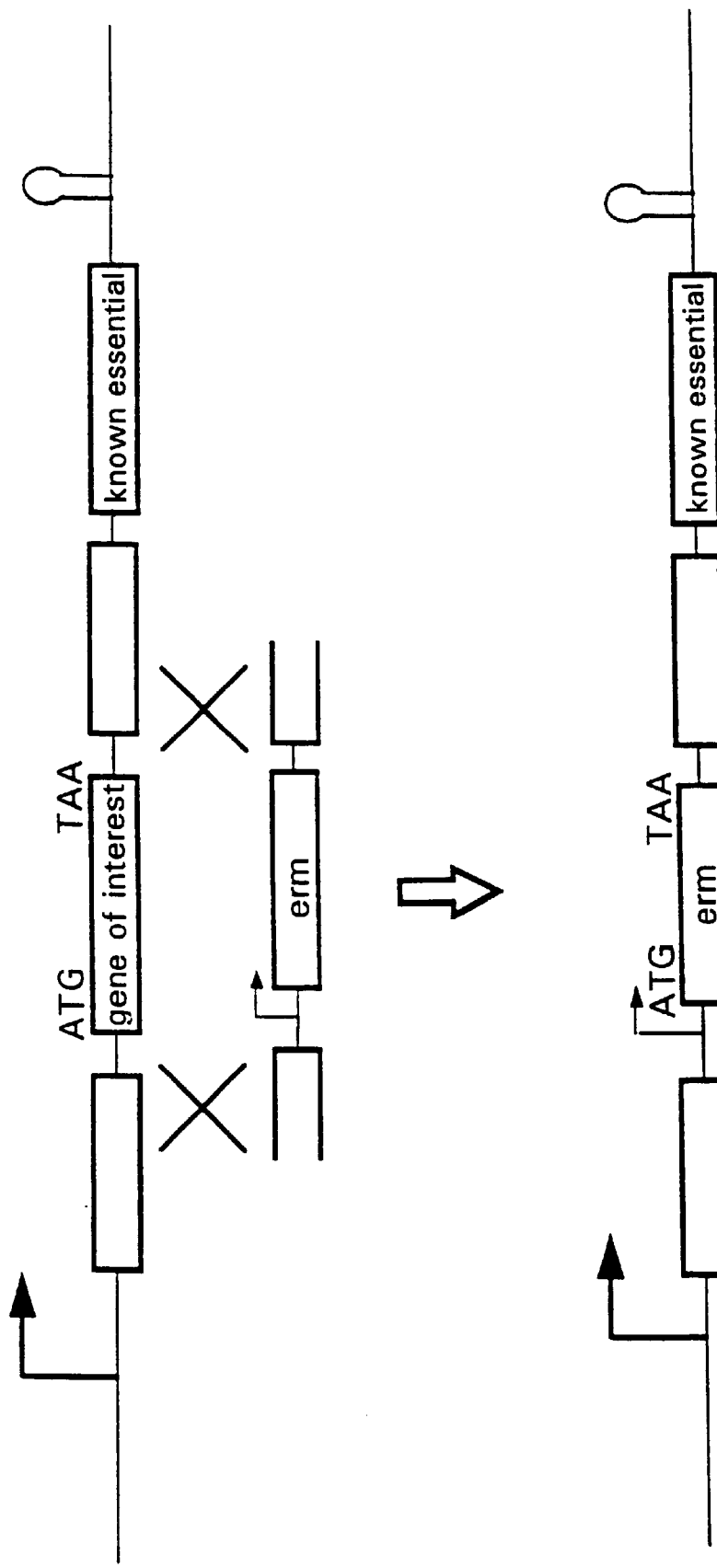
FIG. 9 is a schematic representation of the strategy used to produce targeted deletions of essential genes in *Streptococcus pneumoniae*.

At least two genes in the bacterium *Streptococcus pneumoniae* have been found to be essential for the survival of these bacteria. These so-called essential genes, yphC and yqjK, encode what are referred to herein as essential polypeptides. The yphC and yqjK genes are useful molecular tools for identifying similar genes in pathogenic microorganisms, such as pathogenic strains of Bacillus. The essential polypeptides are useful targets for identifying compounds that are inhibitors of the pathogens in which the essential polypeptides are expressed.

Identifying Essential Streptococcus Genes

As shown by the experiments described below, both the yphC and yqjK genes are essential for survival of *Streptococcus pneumoniae*. *Streptococcus pneumoniae* is available from the ATCC. In general, and for the examples set forth below, essential genes can be identified by creating targeted deletions of genes of interest in a bacterium, e.g., *S. pneumoniae*. These genes of interest were selected as follows. Using standard molecular biology techniques, a library containing fragments of the *Streptococcus pneumoniae* genome was made, using M13 phage or plasmid DNA as the vector. Open reading frames (ORFs) contained within this library were randomly sequenced, using primers that hybridized to the vector. The genes of interest selected for targeted deletion satisfied four criteria, as determined by comparing the sequences with the GenBank database of nucleotide sequences: (i) the ORF had no known function; (ii) the ORF had an ortholog in *Bacillus subtilis*; (iii) the ORF was conserved in other bacteria, with $p<10^{-10}$; and (iv) the ORF had no eukaryotic ortholog, with $p>10^{-3}$. The Streptococcus genes yphC and yqjK met each of these criteria, suggesting that a compound that inhibited the yphC or yqjK genes or gene products would have a broad spectrum of antibacterial activity.

The yphC and yqjK genes each were replaced with a nucleic acid sequence conferring resistance to the antibiotic erythromycin (an "erm" gene). Other genetic markers can be used in lieu of this particular antibiotic resistance marker. Polymerase chain reaction (PCR) amplification was used to make a targeted deletion in the Streptococcus genomic DNA, as shown in FIG. 8. Several PCR reactions were used to produce the DNA molecules needed to carry out target deletion of the genes of interest. First, using primers 5 and 6, an erm gene was amplified from pIL252 from *B. subtilis* (available from the Bacillus Genetic Stock Center, Columbus, Ohio). Primer 5 consists of 21 nucleotides that are identical to the promoter region of the erm gene and complementary to Sequence A. Primer 5 has the sequence 5'GTG TTC GTG CTG ACT TGC ACC3' (SEQ ID NO:22). Primer 6 consists of 21 nucleotides that are complementary to the 3' end of the erm gene. Primer 6 has the sequence 5'GAA TTA TTT CCT CCC GTT AAA3' (SEQ ID NO:23). PCR amplification of the erm gene was carried out under the following conditions: 30 cycles of 94° C. for 1 minute, 55° C. for 1 minute, and 72° C. for 1.5 minutes, followed by one cycle of 72° C. for 10 minutes.

In the second and third PCR reactions, sequences flanking the gene of interest were amplified and produced as hybrid DNA molecules that also contained a portion of the erm gene. The second reaction produced a double-stranded DNA molecule (termed "Left Flanking Molecule") that includes sequences upstream of the 5' end of the gene of interest and the first 21 nucleotides of the erm gene. As shown in FIG. 8, this reaction utilized primer 1, which is 21 nucleotides in length and identical to a sequence that is located approximately 500 bp upstream of the translation start site of the gene of interest. Primers 1 and 2 are gene-specific and have the sequences 5'TGA AGC CTG TCA AGG ACG AGG3' (SEQ ID NO:24) and 5'CCT TAC GTG GTC GAA TTG TGG3' (SEQ ID NO:25), respectively, for yqjK. For yphC, primers 1 and 2 have the sequences 5'TGT ATG AAT TGG TAC CTC AAG3' (SEQ ID NO:26) and 5'ACA ATG GCA ATA GTT GGT AGG3' (SEQ ID NO:27), respectively. Primer 2 is 42 nucleotides in length, with 21 of the nucleotides at the 3' end of the primer being complementary to the 5' end of the sense strand of the gene of interest. The 21 nucleotides at the 5' end of the primer were identical to sequence A and are therefore complementary to the 5' end of the erm gene. Thus, PCR amplification using primers 1 and 2 produced the left flanking DNA molecule, which is a hybrid DNA molecule containing a sequence located upstream of the gene of interest and 21 base pairs of the erm gene, as shown in FIG. 8.

The third PCR reaction was similar to the second reaction, but produced the right flanking DNA molecule, shown in FIG. 8. The right flanking DNA molecule contains 21 base pairs of the 3' end of the erm gene, a 21 base pair portion of the 3' end of the gene of interest, and sequences downstream of the gene of interest. This right flanking DNA molecule was produced with gene-specific primers 3 and 4. For yqjK, primers 3 and 4 have the sequences 5'GTG GAA ATC TAG CAG TCA CAG3' (SEQ ID NO:28) and 5'ATC TGG TTC TAG CAG GAA GCG3' (SEQ ID NO:29), respectively. For yphC, primers 3 and 4 have the sequences 5'CAT TGC CAG TCC TGT TGC TGG3' (SEQ ID NO:30) and 5'ATG GCA TCC ATG ACA TCG3' (SEQ ID NO:31), respectively. Primer 3 is 42 nucleotides; the 21 nucleotides at the 5' end of primer 3 are identical to Sequence B and therefore are identical to the 3' end of the erm gene. The 21 nucleotides at the 3' end of primer 3 are identical to the 3' end of the gene of interest. Primer 4 is 21 nucleotides in length and is complementary to a sequence located approximately 500 bp downstream of the gene of interest.

PCR amplification of the left and right flanking DNA molecules was carried out, separately, in 50 μl reaction mixtures containing: 1 μl *Streptococcus pneumoniae* (RX1) DNA (0.25 μg), 2.5 μl primer 1 or primer 4 (10 pmol/μl), 2.5 μl primer 2 or primer 3 (20 pmol/μl), 1.2 μl a mixture dNTPs (10 mM each), 37 μl H$_2$O, 0.7 μl Taq polymerase (5 U/μl), and 5 μl 10×Taq polymerase buffer (10 mM Tris, 50 mM KCl, 2.5 mM MgCl$_2$). The left and right flanking DNA molecules were amplified using the following PCR cycling program: 95° C. for 2 minutes; 72° C. for 1 minute; 94° C. for 30 seconds; 49° C. for 30 seconds; 72° C. for 1 minute; repeating the 94° C., 49° C., and 72° C. incubations 30 times; 72° C. for 10 minutes and then stopping the reactions. A 15 μl aliquot of each reaction mixture then was electrophoresed through a 1.2% low melting point agarose gel in TAE buffer, and then stained with ethidium bromide. Fragments containing the amplified left and right flanking DNA molecules were excised from the gel and purified using a QIAQUICK™ gel extraction kit (Qiagen, Inc.) Other art-known methods for amplifying and isolating DNA can be substituted. The flanking left and right DNA fragments were eluted into 30 μl TE buffer at pH 8.0.

The amplified erm gene and left and right flanking DNA molecules were then fused together to produce the fusion product, as shown in FIG. 8. The fusion PCR reaction was carried out in a volume of 50 μl containing: 2 μl of each of the left and right flanking DNA molecules and the erm gene PCR product; 5 μl of 10×buffer; 2.5 μl of primer 1 (10 pmol/μl); 2.5 μl of primer 4 (10 pmol/μl), 1.2 μl dNTP mix (10 mM each) 32 μl H$_2$O, and 0.7 μl Taq polymerase. The PCR reaction was carried out using the following cycling program: 95° C. for 2 minutes; 72° C. for 1 minute; 94° C. for 30 seconds, 48° C. for 30 seconds; 72° C. for 3 minutes; repeat the 94° C., 48° C., and 72° C. incubations 25 times; 72° C. for 10 minutes. After the reaction was stopped, a 12 μl aliquot of the reaction mixture was electrophoresed through an agarose gel to confirm the presence of a final product of approximately 2 kb.

A 5 μl aliquot of the fusion product was used to transform *S. pneumoniae* grown on a medium containing erythromycin in accordance with standard techniques. As shown in FIG. 9, the fusion product and the *S. pneumoniae* genome undergo a homologous recombination event so that the erm gene replaces the chromosomal copy of the gene of interest, thereby creating a gene knockout. Disruption of an essential gene results in no growth on a medium containing erythromycin. Using this gene knockout method, the yphC and yqjK genes were identified as being essential for survival. The portion of the yphC open reading frame that was sequenced prior to carrying out targeted deletion is depicted in FIGS. 1A–B. The full-length yphC sequence (depicted in FIGS. 2A–2B) was compiled by searching the TIGR sequence database for a clone from *S. pneumoniae* having a sequence overlapping the sequence depicted in FIGS. 1A–B and combining the 3' end of the gene from the database with the 5' end of the gene depicted in FIGS. 1A–B. The sequence contained in the clone from the database was of unknown function.

Identification of Orthologs of Essential Genes

Having shown that the yphC and yqjK genes are essential for survival of Streptococcus, orthologs of these genes, when identified in other organisms, for example *B. subtilis* or *E. coli*, can be tested to determine whether they are essential for survival of those organisms as well. To this end, the coding sequences of yphC and yqjK were used to search the GenBank database of nucleotide sequences, and orthologs of each sequence were identified in *B. subtilis* and *E. coli*. Sequence comparisons were performed using the Basic Local Alignment Search Tool (BLAST) (Altschul et al., J. Mol. Biol. 215:403–410, 1990). The percent sequence identity shared by the essential polypeptides and their orthologs was determined using the GAP program from the Genetics Computer Group (GCG) Wisconsin Sequence Analysis Package (Wisconsin Package Version 9.1; Madison, Wis.). The default parameters for gap weight (12) and length weight (4) were used.

Typically, essential polypeptides and their orthologs share at least 25% (e.g., at least 30% or 40%) sequence identity. Typically, the DNA sequences encoding essential polypeptides and their homologs or orthologs share at least 20% (e.g., at least 30%, 35%, 40% or 45%) sequence identity. Bioinformatics analysis of the yphC and yqjK genes showed that these genes are widely conserved among bacteria.

To determine whether the identified orthologs of yphC and yqjK are essential for survival of other bacteria, each of the orthologous genes was separately deleted from the genome of the host organism, as described in detail below. The observation that the *B. subtilis* and *E. coli* orthologs of yphC (B-yphC and yfgK, respectively) also are essential for survival of *B. subtilis* and *E. coli* suggests that the yphC gene is essential in all bacteria where it is present. Therefore, an antibacterial agent targeted to this gene or its gene product is expected to have a broad spectrum of antibacterial activity. The observation that the *B. subtilis* ortholog of yqjK (B-yqjK), but not the *E. coli* ortholog (elaC), is essential for survival suggests that this gene is essential in all gram-positive bacteria in which it is present, and not essential in gram negative bacteria. Therefore, an antibacterial agent targeted to the yqjK gene or its gene product is expected to have antibacterial activity against all gram-positive bacteria.

Deletion and Determination of Essentiality of the yphC and yqjK genes in *Bacillus subtilis*

Figure 10:
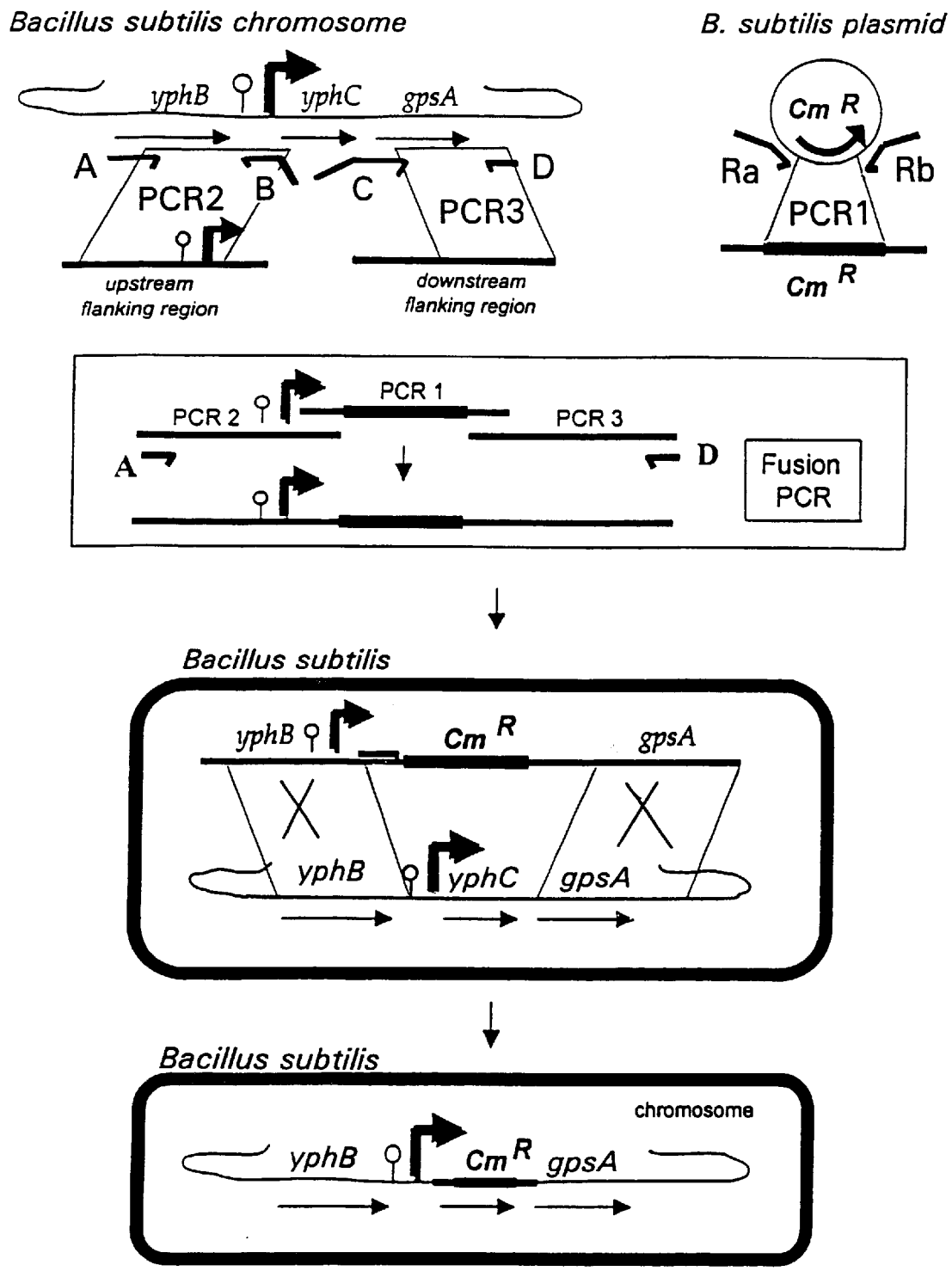
FIG. 10 is a schematic representation of the strategy used to obtain non-polar gene deletions of yphC and yqjK in *B. subtilis*.

The following examples illustrate that the *B. subtilis* orthologs of yphC and yqjK (i.e., B-yphC and B-yqjK) are essential for survival of *B. subtilis*. Two strategies were used to produce knockout mutations of the B-yphC and B-yqjK genes in *B. subtilis*, and a determination of the essential phenotype of the B-yphC and B-yqjK genes was made, as described below. The first strategy (illustrated in FIG. 10) was similar to the targeted deletion strategy used to knock out genes in Streptococcus, as described above. The significant differences were as follows.

(A.) In PCR, a chloramphenicol resistant gene (CmR) of *B. subtilis*, from plasmid pDG283, was used in lieu of an erythromycin resistance gene. Alternatively, any *B. subtilis* marker can be used.

(B.) The primers used to amplify the CmR gene and primers B and C, which immediately flank the yphC ORF, contain a stretch of 27 nucleotides termed "universal overlapping sequences." These universal overlapping sequences can be used efficiently in PCR amplifications, and facilitate the use of various insertion sequences in fusion PCR reactions. Resistance markers, promoters, regulatory elements, or any nucleic acid sequence can be amplified with such overlapping sequences and be used with the same set of gene deletion primers (primers A, B, C, and D). The sequence for the 5' overlapping region is 5'CACAGGAAACAGC TAT-GACCATGATTA3' (SEQ ID NO:22) and the sequence for the 3' overrlapping region is 5'GAAATAAATGCATCTG-TATTTGAATG3' (SEQ ID NO:33)

(C.) The left and right flanking DNA molecules produced by PCR should be at least 900 (e.g., 1000) nucleotides in length to optimize recombination into the B. subtilis chromosome.

(D.) To produce the fusion product, two simultaneous PCR reactions were used. One reaction used an annealing temperature of 50° C., and the other used a temperature of 65° C. Longer extension times were used (30–60 more seconds), and a Long high fidelity polymerase was also used according to the manufacturer's instructions (Boehringer-Mannheim).

(E.) Competent cells of the wild type strain, PY79, were used according to standard B. subtilis protocols (Molecular Biological Methods for Bacillus, 1990, Harwood and Cutting, Eds. Wiley & Sons, Ltd. England).

(F.) The sequence of the primers shown in FIG. 10 was as follows: primer Ra, (5'CACAGGAAACAGCTATGACCA TGATTAAACTAAAGCACCCATTAGTTCA3' (SEQ ID NO:34)) which hybridized to a sequence upstream of the CmR promoter; primer Rb (5'CATTCAAATACAGA TGCATTTTATTTCCTCATATT ATAAAAGCCAGT-CATT3' (SEQ ID NO:35)), which hybridized to a sequence located adjacent to the transcription terminator; primer A-YPHC (5'GCCATTGCGTTTGAAAG3' (SEQ ID NO:36)); primer A-YQJK (5'TGCTTCGCCGATTTCTT3' (SEQ ID NO:37); primer B-YPHC (5'TAATCATGGTCAT AGCTGTTTCCTGTGTATGAAAAGAAACCCTTCA GAG3' (SEQ ID NO:38)), which is located adjacent to the yphC start codon; primer B-YQJK (5'TAATCATGGTCA TAGCTGTTTCCTGTGCATACCG AACGCCTTTCTT3' (SEQ ID NO:39)), which is located adjacent to the yqjK start codon; primer C-YPHC (5'GAAATAAATGCA TCTG-TATTTGAATGTTTTAGAAAACCGAATCAGAGA3' (SEQ ID NO:40)), which is located adjacent to the yphC stop codon; primer C-YQJK (5'GAAATAAATGCATCT GTATTTGAATGAATAGCGTGGCGGCATA3' (SEQ ID NO:41)), located adjacent to the yqjK stop codon; primer D-YPHC (5'ATTCAGATCGAATACTCCTG3' (SEQ ID NO:42)); and primer D-YQJK (5'AAAGCGGGCAAAGC AGA3' (SEQ ID NO:43)).

Competent cells that were transformed with the fused left and right flanking DNA molecules were incubated for 18 hours at 37° C. on a selective medium (LB, 5 μg/ml Cm) to determine whether the gene in question was essential (as characterized by lack of colony growth) or non-essential (as characterized by the appearance of dozens to hundreds of colonies). When these deletion experiments were performed with the yphC and yqjK genes, separately, no colonies were detected on the selective medium, indicating that each of these genes is essential for survival of B. subtilis.

Several control experiments were performed to ensure that the observed lack of cell growth was due to the essential nature of the B-yphC and B-yqjK genes. Simultaneous PCR reactions and transformations with genes that were known not to be essential produced hundreds of colonies in similar experiments, indicating that experimental conditions were adequate to ensure that the lack of colony growth was indicative of an essential gene. The CmR gene insertion was also shown to have non-polar effects on downstream genes and allowed efficient expression of downstream genes.

The second strategy used to obtain deletion mutants of the yphC and yqjK genes of B. subtilis involved the construction of conditional null mutants that can halt the expression of the chosen gene and allow observation of the mutant phenotype (FIGS. 11A–11C). In these mutants, a wild-type copy of the yphC or yqjK gene was placed under the control of a B. subtilis Para promoter, which is a tightly regulatable promoter that can efficiently turn off gene expression. These regulatable genetic constructs were subsequently inserted into the B. subtilis chromosome. As shown in FIG. 11A, the regulatable genetic constructs contained an amylase gene (amy) sequence and CmR sequence for integration into chromosome at the amy locus. Disruption of the amy gene by double crossover is innocuous to the cell, and recombinants are easily detectable on starch plates because amy$^+$ cells produce colonies having transparent halos.

After integration of the regulatable yphC or yqjK genes into the chromosome of wild-type cells, the resulting cells were rendered competent and transformed with a fusion PCR fragment containing a replacement resistant marker (FIG. 11B), as described above. In this case, the fusion PCR fragment contained a Kanamycin resistance gene from B. subtilis (Kan) instead of the CmR gene. Selection for this Kan marker during transformation of the cells containing the ectopically inserted regulated yphC or yqjK genes was performed in the presence of arabinose to allow expression of the yphC or yqjK genes and trans complementation of the deletion (FIG. 11C).

The yphC and yqjK mutants obtained in this manner were able to grow on a selective medium (LB Kan) in the presence of 0.2% arabinose, while selections made in wild type cells did not yield any mutants. Colonies containing the regulated genes and their deletions then were picked and streaked onto a similar medium (LB Kan, 0.2% arabinose), and onto plates containing a selective medium with lower concentrations of arabinose, no arabinose, or in the presence of 0.2% glucose. After 18 hours of incubation to allow for growth, the only plates that contained colonies were those plates that contained 0.2%, 0.02%, or 0.002% arabinose. Lower concentrations of the inducer or repressing conditions (i.e., the lack of arabinose or presence of glucose) did not allow cell growth and formation of colonies. Thus, these experiments indicated that: (i) the deletion created by the fusion PCR did not affect putative essential genes downstream of yphC or yqjK, since expression of only the gene in question was sufficient to obtain efficient complementation, and (ii) expression of the yphC and the yqjK genes is necessary for survival of the B. subtilis cells.

The experiments described above confirmed that B-yphC and B-yqjK are essential in B. subtilis. These experiments yielded conditional lethal strains that can be used in a variety of screens and approaches, including underexpression/overexpression assays, transcription profiling, etc. The constructions of knockout mutations of the yphC and yqjK genes can be accomplished using any of various art-known methods.

Assay of the Essential Nature of yphC and yqjK Orthologs in E. coli

The discovery that the yphC and yqjK genes are essential in Streptococcus pneumoniae and in B. subtilis suggests that these genes are essential in all Gram-positive bacteria. To further extend these observations to Gram-negative bacteria, and therefore to all bacteria, deletion mutants were produced for the *E. coli* orthologs of yphC and yqjK.

The general strategy used to produce *E. coli* gene deletions, as conditional null mutants, is schematically represented in FIG. 12. First, a copy of the wild type gene to be deleted was cloned into a runaway, counter-selectable vector containing the Pbad promoter of *E. coli*. This *E. coli* promoter is turned on in the presence of arabinose and is tightly controlled like its *B. subtilis* counterpart, described above. Cells containing this vector were then used to introduce an in-frame deletion of the chosen gene by replacing the gene with a markerless small TAG of approximately 30 nucleotides.

The upstream and downstream regions that flank the chosen gene were amplified by PCR using primers that introduced a 27–30 nucleotide overlapping TAG. Fusion PCR reactions were carried out with only these two fragments that are joined with the TAG lying in the middle, thereby replacing the chosen gene.

This fragment was then cloned into a temperature-sensitive, counterselectable plasmid, pKO-3, and inserted into the chromosome in accordance with conventional techniques (see, e.g., Church et al., 1997, J. Bacteriol.). The resulting in-frame deletion was complemented by expression of the wild type gene from the Pbad vector in the presence of arabinose (FIG. 11C, P turned on. The deletion mutant can suppress gene expression under conditions lacking arabinose, in the presence of glucose (P turned off), or in the presence of streptomycin without IPTG, which allows loss of the plasmid (because the origin of replication of the complementing Pbad plasmid is under lac-IPTG control).

As shown in FIG. 12, deletion of the yphC sequence in *E. coli* and its substitution by a TAG in the presence of a complementing Pbad-yphC ortholog plasmid resulted in mutants that grew well on arabinose plates but which failed to grow on glucose or streptomycin plates. This result indicates that the yfgK gene (i.e., the *E. coli* yphC ortholog) is essential for the survival of *E. coli*. In contrast, similar experiments carried out with the *E. coli* yqjK ortholog, elaC, showed significant cell growth under all conditions, indicating that the yqjK gene is not essential in *E. coli*. Alternatively, it is possible that other *E. coli* genes that have arylsulfatase/phosphatase activity that have no sequence similarity are able to complement for the lack of elaC function.

The fact that the *B. subtilis* and *E. coli* orthologs of the yphC gene are essential for survival indicates that this gene is essential in all bacteria in which it is present. The yqjK gene, which is essential for survival of *S. pneumoniae* and *B. subtilis*, is thought to be essential in all Gram-positive bacteria, but not in *E. coli*. Therefore, an antibacterial agent targeted to the yphC gene or its gene product is expected to have a broad spectrum of antibacterial activity (including Gram-positive and Gram-negative bacteria), while an antibacterial agent targeted to the yqjK gene or its gene product is expected to have antibacterial activity against Gram-positive bacteria.

Identification of Essential Genes and Polypeptides in Additional Bacterial Strains The yphC and yqjK genes and various orthologs, or fragments thereof, can be used to detect homologous or orthologous genes in yet other organisms. In particular, these genes can be used to analyze various pathogenic and non-pathogenic strains of bacteria. Fragments of a nucleic acid (DNA or RNA) encoding an essential polypeptide, homolog or ortholog (or sequences complementary thereto) can be used as probes in conventional nucleic acid hybridization assays of pathogenic bacteria. For example, nucleic acid probes (which typically are 8–30, usually 15–20, nucleotides in length) can be used to detect essential genes or homologs or orthologs thereof in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragments thereof, is labeled and used to screen a genomic library constructed from mRNA obtained from a bacterial strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the library, or other nucleic acid sample, typically is performed under moderate to stringent conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having ≧95% identity with the probe are sought, the final wash temperature is decreased by 5° C.). In practice, the change in $T_m$ can be between 0.5° and 1.5° C. per 1% mismatch.

Stringent conditions include, for example, hybridizing at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, libraries constructed from pathogenic or non-pathogenic bacterial strains can be screened. For example, such strains can be screened for expression of essential genes by Northern blot analysis. Upon detection of transcripts of the essential genes or homologs thereof, libraries can be constructed from RNA isolated from the appropriate strain, utilizing standard techniques well known to those of skill in the art. Alternatively, a total genomic DNA library can be screened using an essential gene probe (or a probe directed to a homolog thereof).

New gene sequences can be isolated, for example, by performing PCR using two degenerate oligonucleotide primer pools designed on the basis of nucleotide sequences within the essential genes, or their homologs or orthologs, as depicted herein. The template for the reaction can be DNA obtained from strains known or suspected to express an essential allele or an allele of a homolog or ortholog thereof. The PCR product can be subcloned and sequenced to ensure that the amplified sequences represent the sequences of a new essential nucleic acid sequence, or a sequence of a homolog thereof.

Synthesis of the various essential polypeptides or their homologs or orthologs (or an antigenic fragment thereof) for use as antigens, or for other purposes, can readily be accomplished using any of the various art-known techniques. For example, an essential polypeptide or homolog or ortholog thereof, or an antigenic fragment(s), can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli* or *B. subtilis*) or in eukaryotic cells, such as yeast cells or in insect cells (e.g., by using a baculovirus-based expression vector).

Proteins and polypeptides can also be produced in plant cells, if desired. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in *Cloning Vectors: A Laboratory Manual* (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, the yphC or yqjK polypeptides or their homologs or orthologs can be produced as fusion proteins. For example, the expression vector pUR278 (Ruther et al., *EMBO J.*, 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary expression system, a baculovirus such as *Autographa californica* nuclear polyhedrosis virus (AcNPV), which grows in *Spodoptera frugiperda* cells, can be used as a vector to express foreign genes. A coding sequence encoding an essential polypeptide or homolog or ortholog thereof can be cloned into a non-essential region (for example the polyhedrin gene) of the viral genome and placed under control of a promoter, e.g., the polyhedrin promoter or an exogenous promoter. Successful insertion of a gene encoding an essential polypeptide or homolog can result in inactivation of the polyhedrin gene and production of non-occluded recombinant virus (i.e., virus lacking the proteinaceous coat encoded by the polyhedrin gene). These recombinant viruses are then typically used to infect insect cells (e.g., *Spodoptera frugiperda* cells) in which the inserted gene is expressed (see, e.g., Smith et al., *J. Virol.*, 46:584, 1983; Smith, U.S. Pat. No. 4,215,051). If desired, mammalian cells can be used in lieu of insect cells, provided that the virus is engineered such that the gene encoding the desired polypeptide is placed under the control of a promoter that is active in mammalian cells.

In mammalian host cells, a number of viral-based expression systems can be utilized. When an adenovirus is used as an expression vector, the nucleic acid sequence encoding the essential polypeptide or homolog can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing an essential gene product in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In general, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., *Methods in Enzymol.*, 153:516, 1987).

The essential polypeptides and their homologs and orthologs can be expressed individually or as fusions with a heterologous polypeptide, such as a signal sequence or other polypeptide having a specific cleavage site at the N- and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the essential polypeptide or homolog or ortholog thereof can be produced by a stably-transfected mammalian cell line. A number of vectors suitable for stable transfection of mammalian cells are available to the public, see, e.g., Pouwels et al. (supra); methods for constructing such cell lines are also publicly known, e.g., in Ausubel et al. (supra). In one example, DNA encoding the protein is cloned into an expression vector that includes the dihydrofolate reductase (DHFR) gene. Integration of the plasmid and, therefore, the essential polypeptide-encoding gene into the host cell chromosome is selected for by including 0.01–300 μM methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra).

A number of other selection systems can be used, including but not limited to, herpes simplex virus thymidine kinase genes, hypoxanthine-guanine phosphoribosyltransferase genes, and adenine phosphoribosyltransferase genes, which can be employed in tk, hgprt, or aprt cells, respectively. In addition, gpt, which confers resistance to mycophenolic acid (Mulligan et al., *Proc. Natl. Acad. Sci. USA,* 78:2072, 1981); neo, which confers resistance to the aminoglycoside G-418 (Colberre-Garapin et al., *J. Mol. Biol.,* 150:1, 1981); and hygro, which confers resistance to hygromycin (Santerre et al., *Gene,* 30:147, 1981), can be used.

Alternatively, any fusion protein can be readily purified by utilizing an antibody or other molecule that specifically binds the fusion protein being expressed. For example, a system described in Janknecht et al., *Proc. Natl. Acad. Sci. USA,* 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns, and histidine-tagged proteins are selectively eluted with imidazole-containing buffers.

Alternatively, yphC or yqjK, or a homolog or ortholog thereof, or a portion thereof, can be fused to an immunoglobulin Fc domain. Such a fusion protein can be readily purified using a protein A column, for example. Moreover, such fusion proteins permit the production of a chimeric form of an essential polypeptide or homolog or ortholog having increased stability in vivo.

Once the recombinant essential polypeptide (or homolog) is expressed, it can be isolated (i.e., purified). Secreted forms of the polypeptides can be isolated from cell culture media, while non-secreted forms must be isolated from the host cells. Polypeptides can be isolated by affinity chromatography. For example, an anti-yphC antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate an essential polypeptide (e.g., a yphC-maltose binding fusion protein, a yphC-β-galactosidase fusion protein, or a yphC-trpE fusion protein; see, e.g., Ausubel et al., supra; New England Biolabs Catalog, Beverly, Mass.).

The recombinant protein can, if desired, be further purified, e.g., by high performance liquid chromatography using standard techniques (see, e.g., Fisher, *Laboratory Techniques In Biochemistry And Molecular Biology,* eds., Work and Burdon, Elsevier, 1980).

Given the amino acid sequences described herein, polypeptides useful in practicing the invention, particularly fragments of essential polypeptides, can be produced by standard chemical synthesis (e.g., by the methods described in *Solid Phase Peptide Synthesis,* 2nd ed., The Pierce Chemical Co., Rockford, Ill., 1984) and used as antigens, for example.

Antibodies

The yphC and yqjK polypeptides (or antigenic fragments or analogs of such polypeptides) can be used to raise antibodies useful in the invention, and such polypeptides can be produced by recombinant or peptide synthetic techniques (see, e.g., Solid Phase Peptide Synthesis, supra; Ausubel et al., supra). Likewise, antibodies can be raised against homologs or orthologs of yphC and yqjK (or antigenic fragments and analogs of such homologs and orthologs). In general, the polypeptides can be coupled to a carrier protein, such as KLH, as described in Ausubel et al., supra, mixed with an adjuvant, and injected into a host mammal. A "carrier" is a substance that confers stability on, and/or aids or enhances the transport or immunogenicity of, an associated molecule. Antibodies can be purified, for example, by affinity chromatography methods in which the polypeptide antigen is immobilized on a resin.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Antibodies useful in the invention include monoclonal antibodies, polyclonal antibodies, humanized or chimeric antibodies, single chain antibodies, Fab fragments, F(ab')$_2$ fragments, and molecules produced using a Fab expression library.

Monoclonal antibodies (mAbs), which are homogeneous populations of antibodies to a particular antigen, can be prepared using yphC, yqjK, or homologs or orthologs thereof and standard hybridoma technology (see, e.g., Kohler et al., *Nature,* 256:495, 1975; Kohler et al., *Eur. J. Immunol.,* 6:511, 1976; Kohler et al., *Eur. J. Immunol.,* 6:292, 1976; Hammerling et al., In *Monoclonal Antibodies and T Cell Hybridomas,* Elsevier, N.Y., 1981; Ausubel et al., supra).

In particular, monoclonal antibodies can be obtained by any technique that provides for the production of antibody molecules by continuous cell lines in culture, such as those described in Kohler et al., *Nature,* 256:495, 1975, and U.S. Pat. No. 4,376,110; the human B-cell hybridoma technique (Kosbor et al., *Immunology Today,* 4:72, 1983; Cole et al., *Proc. Natl. Acad. Sci. USA,* 80:2026, 1983); and the EBV-hybridoma technique (Cole et al., *Monoclonal Antibodies and Cancer Therapy,* Alan R. Liss, Inc., pp. 77–96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of an essential polypeptide or homolog or ortholog thereof in an immunoassay, such as a Western blot or immunoprecipitation analysis using standard techniques, e.g., as described in Ausubel et al., supra. Antibodies that specifically bind to the essential polypeptides, or conservative variants and homologs and orthologs thereof, are useful in the invention. For example, such antibodies can be used in an immunoassay to detect an essential polypeptide in pathogenic or non-pathogenic strains of bacteria.

Preferably, antibodies of the invention are produced using fragments of the essential polypeptides that appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in E. coli and purified using a glutathione agarose affinity matrix as described in Ausubel, et al., supra.

If desired, several (e.g., two or three) fusions can be generated for each protein, and each fusion can be injected into at least two rabbits. Antisera can be raised by injections in a series, typically including at least three booster injections. Typically, the antisera is checked for its ability to immunoprecipitate a recombinant essential polypeptide or homolog, or unrelated control proteins, such as glucocorticoid receptor, chloramphenicol acetyltransferase, or luciferase.

Techniques developed for the production of "chimeric antibodies" (Morrison et al., Proc. Natl. Acad. Sci., 81:6851, 1984; Neuberger et al., Nature, 312:604, 1984; Takeda et al., Nature, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778; 4,946,778; and 4,704,692) can be adapted to produce single chain antibodies against an essential polypeptide or homolog or ortholog thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to F(ab')$_2$ fragments, which can be produced by pepsin digestion of the antibody molecule, and Fab fragments, which can be generated by reducing the disulfide bridges of F(ab')$_2$ fragments. Alternatively, Fab expression libraries can be constructed (Huse et al., Science, 246:1275, 1989) to allow rapid and easy identification of monoclonal Fab fragments with the desired specificity.

Polyclonal and monoclonal antibodies that specifically bind to essential polypeptides, homologs, or orthologs can be used, for example, to detect expression of an essential gene, homolog, or ortholog in another bacteria. For example, an essential polypeptide can be readily detected in conventional immunoassays of bacteria cells or extracts. Examples of suitable assays include, without limitation, Western blotting, ELISAs, radioimmune assays, and the like.

Assay for Antibacterial Agents

The invention provides methods for identifying antibacterial agents. Without being bound by any particular theory as to the biological mechanism involved, the new antibacterial agents are thought to inhibit specifically (1) the function of the yphC or yqjK polypeptide(s), or homologs or orthologs thereof, or (2) expression of the yphC or yqjK genes, or homologs or orthologs thereof.

Alignment of the yphC protein sequence with similar sequences from the GenBank database suggests that the yphC protein has GTPase activity. Similarly, the alignment of the yqjK protein with sequences from GenBank suggests that the yqjK protein has arylsulfatase activity. In experiments designed to test whether the yphC and yqjK proteins have the proposed biochemical activities, the yphC protein was shown to have GTPase activity, and the yqjK protein was shown to have arylsulfatase activity.

The enzymatic activity of each protein suggests novel features of each enzyme. For example, the yphC protein contains two GTP-binding sites, but only one of the sites appears to be active. The yqjK protein has phosphatase activity in addition to arylsulfatase activity, and the protein carries out an activation step that is catalyzed by manganese ions. In the genetic experiments described herein, the observed biochemical activities of yphC and yqjK were shown to be linked to the essential nature of the proteins. Mutants of the GTP-binding sites of the yphC gene result in proteins that lack GTPase activity and that are unable to complement null yphC mutants. Similarly, yqjK mutants that lack arylsulfatase activity are unable to complement null yqjK mutants. Additionally, mutants that lacked arylsulfatase activity also lacked phosphatase activity and vice versa. These experiments indicate that inhibition of the enzymatic activities of yphC or yqjK in cell cultures impairs the viability of the cells and results in cell death. Thus, these biochemical activities can be used in vivo or in vitro, alone or in combination with any art-known methods to detect these activities, to identify antibacterial agents.

In various suitable methods, screening for antibacterial agents is accomplished by identifying those compounds (e.g., small organic molecules) that inhibit the activity of an essential polypeptide or the expression of an essential gene. Screening for antibacterial agents can be accomplished by (i) identifying those compounds that interact with or bind to an essential polypeptide and (ii) further testing such compounds for their ability to inhibit bacterial growth in vitro or in vivo.

Examples of suitable screening methods are set forth in U.S. Pat. Nos. 5,679,582 and 5,585,277, which are incorporated herein by reference. Briefly, in these methods, a target protein is incubated in the presence of a test compound (i.e., test ligand) to produce a "test combination," and the target protein is incubated in the absence of a test compound to produce a "control combination." The test and control combinations are then treated to cause a detectable fraction of the target protein to exist in a partially or totally unfolded state. The extent to which the target protein occurs in a folded state, an unfolded state, or both, in the test and control combinations is then determined. When the target protein is present in the folded state to a greater or lesser extent in the test combination than in the control combination, the test compound is a compound that binds the target protein.

In an alternative method, binding of a test compound to a target protein is detected using capillary electrophoresis. Briefly, test compounds (e.g., small molecules) that bind to the target protein cause a change in the electrophoretic mobility of the target protein during capillary electrophoresis. Suitable capillary electrophoresis methods are known in the art (see, e.g., Freitag, J. Chromatography B, Biomedical Sciences & Applications: 722(1–2):279–301, Feb. 5, 1999; Chu and Cheng, Cellular & Molecular Life Sciences: 54(7):663–83, July 1998; Thormann et al., Forensic Science International: 92(2–3): 157–83, Apr. 5, 1998; Rippel et al., Electrophoresis: 18(12–13): 2175–83, November 1997; Hage and Tweed, J. Chromatography. B, Biomedical Sciences & Applications: 699(1–2):499–525, Oct. 10, 1997; Mitchelson et al., Trends In Biotechnology: 15(11):448–58, November 1997; Jenkins and Guerin J. Chromatography B. Biomedical Applications: 682(1):23–34, Jun. 28, 1996; and Chen and Gallo, Electrophoresis: 19(16–17):2861–9, November 1998.

Inhibitors of yphC can also be identified in the following biochemical assay for detection of GTPase inhibitors. This assay uses a calorimetric detection system for the detection of nanomolar amounts of inorganic phosphate. The assay can be carried out in a clear bottom 96-well microplate (e.g., Corning-COSTAR Catalog #9710). A 20 µl aliquot of each test compound in 10% DMSO is placed into each well of the plate, except those wells that are used as controls. A 20 µl aliquot of 420 µM GTP then is added to each well of the plate, except those wells that are used for control reactions. 20 µl of $IC_{50}$ controls, containing 225 µM GDP, is dispensed into two of the control wells; 20 µl of $IC_{100}$ (2.25 ml of 0.5M EDTA in 12.75 ml of 420 µM GTP) is dispensed into two other control wells; and 20 µl of no inhibition controls containing 420 µM GTP is dispensed into four other control wells. 20 µl of 2×-buffer (100 mM Tris HCL, 500 mM KCl, 10 mM $MGCl_2$, 0.2 mg/ml Acetylated-BSA, $H_2O$) plus yphC enzyme solution (to provide 1 µg/well) then is dispensed into each well, and the plate is incubated at room temperature for 3.5 hours. To stop the enzyme reaction, 150 µl of 0.045% Malachite Green/35 mM EDTA solution is added to each well. After 25 minutes, 50 µl of 15% citrate is added to each well to prevent further color development. The samples then are mixed vigorously (e.g., with a TOMTEC-Quadra-96, Model 320) until a homogeneous solution results. The plates subsequently are read using a plate reader (e.g., a Wallac-Victor 2 plate reader) set at a wavelength of 650 nm. Generally, the plates should be read within 24 hours of adding the Malachite Green and citrate.

The percent inhibition for each sample well can be calculated as follows. The average of the two wells that contained $IC_{100}$ controls can be used as the background counts. The percent inhibition can calculated according the following formula:

% inhibition=[1-(sample counts−background counts)/(average counts−background counts)]×100.

Test compounds that produce greater than 40% inhibition may be retested with a dose response at a higher concentration, if desired.

Other methods for identifying antibacterial agents include various cell-based methods for identifying polypeptides that bind yphC, yqjK, or homologs or orthologs thereof, such as the conventional two-hybrid assays of protein/protein interactions (see e.g., Chien et al., Proc. Natl. Acad. Sci. USA, 88:9578, 1991; Fields et al., U.S. Pat. No. 5,283,173; Fields and Song, Nature, 340:245, 1989; Le Douarin et al., Nucleic Acids Research, 23:876, 1995; Vidal et al., Proc. Natl. Acad. Sci. USA, 93:10315–10320, 1996; and White, Proc. Natl. Acad. Sci. USA, 93:10001–10003, 1996). Generally, the two-hybrid methods involve reconstitution of two separable domains of a transcription factor in a cell. One fusion protein contains the essential polypeptide (or homolog or ortholog thereof) fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the essential polypeptide to the test polypeptide (i.e., candidate antibacterial agent) reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

In another exemplary assay, but not the only assay, a promoter that responds to depletion of the essential polypeptide by upregulation or downregulation is linked to a reporter gene (e.g., β-galactosidase, gus, or GFP), as described above. A bacterial strain containing this reporter gene construct is then exposed to test compounds. Compounds that inhibit the essential polypeptide (or other polypeptides in the essential pathway in which the essential polypeptide participates) will cause a functional depletion of the essential polypeptide and therefore lead to an upregulation or downregulation of expression the reporter gene. Because the polypeptides described herein are essential for the survival of bacteria, compounds that inhibit the essential polypeptides in such an assay are expected to be antibacterial agents and can be further tested, if desired, in conventional susceptibility assays.

The methods described above can be used for high throughput screening of numerous test compounds to identify candidate antibacterial (or anti-bacterial) agents. Having identified a test compound as a candidate antibacterial agent, the candidate antibacterial agent can be further tested for inhibition of bacterial growth in vitro or in vivo (e.g., using an animal, e.g., rodent, model system) if desired. Using other, art-known variations of such methods, one can test the ability of a nucleic acid (e.g., DNA or RNA) used as the test compound to bind yphC, yqjK, or a homolog or ortholog thereof.

In vitro, further testing can be accomplished by means known to those in the art such as an enzyme inhibition assay or a whole-cell bacterial growth inhibition assay. For example, an agar dilution assay identifies a substance that inhibits bacterial growth. Microtiter plates are prepared with serial dilutions of the test compound, adding to the preparation a given amount of growth substrate, and providing a preparation of bacteria. Inhibition of bacterial growth is determined, for example, by observing changes in optical densities of the bacterial cultures.

Inhibition of bacterial growth is demonstrated, for example, by comparing (in the presence and absence of a test compound) the rate of growth or the absolute growth of bacterial cells. Inhibition includes a reduction of one of the above measurements by at least 20%. Particularly potent test compounds may further reduce the growth rate (e.g., by at least 25%, 30%, 40%, 50%, 75%, 80%, or 90%).

Rodent (e.g., murine) and rabbit animal models of bacterial infections are known to those of skill in the art, and such animal model systems are accepted for screening antibacterial agents as an indication of their therapeutic efficacy in human patients. In a typical in vivo assay, an animal is infected with a pathogenic strain of bacteria, e.g., by inhalation of bacteria such as Streptococcus pneumoniae, and conventional methods and criteria are used to diagnose the mammal as being afflicted with a bacterial infection. The candidate antibacterial agent then is administered to the mammal at a dosage of 1–100 mg/kg of body weight, and the mammal is monitored for signs of amelioration of disease. Alternatively, the test compound can be administered to the mammal prior to infecting the mammal with the bacteria, and the ability of the treated mammal to resist infection is measured. Of course, the results obtained in the presence of the test compound should be compared with results in control animals, which are not treated with the test compound. Administration of candidate antibacterial agents to the mammal can be carried out as described below, for example.

Pharmaceutical Formulations

Treatment includes administering a pharmaceutically effective amount of a composition containing an antibacterial agent to a subject in need of such treatment, thereby inhibiting bacterial growth in the subject. Such a composition typically contains from about 0.1 to 90% by weight (such as 1 to 20% or 1 to 10%) of an antibacterial agent of the invention in a pharmaceutically acceptable carrier.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the antibacterial agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antibacterial agent in each pharmaceutical formulation varies according to the formulation itself and the therapeutic effect desired in the specific pathologies and correlated therapeutic regimens. Appropriate dosages of the antibacterial agents can be readily determined by those of ordinary skill in the art of medicine by monitoring the mammal for signs of disease amelioration or inhibition, and increasing or decreasing the dosage and/or frequency of treatment as desired. The optimal amount of the antibacterial compound used for treatment of conditions caused by or contributed to by bacterial infection may depend upon the manner of administration, the age and the body weight of the subject, and the condition of the subject to be treated. Generally, the antibacterial compound is administered at a dosage of 1 to 100 mg/kg of body weight, and typically at a dosage of 1 to 10 mg/kg of body weight.

Other Embodiments

The invention also features fragments, variants, analogs, and derivatives of the polypeptides described above that retain one or more of the biological activities of the yphC and yqjK polypeptides, e.g., GTPase or sulfatase activities. Included within the invention are naturally-occurring and non-naturally-occurring variants. Compared with the naturally-occurring essential gene sequences depicted in FIGS. 1A–B and FIGS. 3A–B, the nucleic acid sequences encoding variants may have a substitution, deletion, or addition of one or more nucleotides. The preferred variants retain a function of an essential polypeptide, e.g., as determined in a complementation assay.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, other art-known assays to detect interactions of test compounds with proteins, or to detect inhibition of bacterial growth also can be used with the essential genes, gene products, and homologs and orthologs thereof.

What is claimed is:

1. An isolated nucleic acid molecule consisting of SEQ ID NO:1 or SEQ ID NO:4.

2. An isolated nucleic acid molecule which encodes:

a yphC polypeptide consisting of the amino acid sequence of SEQ ID NO:2, as depicted in FIGS. 1A–B; or a yphC polypeptide consisting of the amino acid sequence of SEQ ID NO:5, as depicted in FIGS. 2A–2B.

3. An isolated nucleic acid molecule consisting of a nucleic acid sequence selected from the group consisting of:

(1) the sequence of SEQ ID NO:1, as depicted in FIGS. 1A–B, or degenerate sequences thereof;

(2) the sequence of SEQ ID NO:1, as depicted in FIGS. 1A–B, or degenerate sequences thereof, wherein each T is replaced by U;

(3) nucleic acid sequences fully complementary to sequences of (1) and (2);

(4) the sequence of SEQ ID NO:4, as depicted in FIGS. 2A–2B, or degenerate sequences thereof;

(5) the sequence of SEQ ID NO:4, as depicted in FIGS. 2A–2B, or degenerate sequences thereof, wherein each T is replaced by U; and (6) nucleic acids fully complementary to (4) and (5).

4. A vector comprising a nucleic acid molecule of claim 1.

5. A host cell comprising an exogenously introduced nucleic acid molecule of claim 1.

* * * * *

SEQUENCE LISTING

```
<160> NUMBER OF SEQ ID NOS: 43

<210> SEQ ID NO 1
<211> LENGTH: 1181
<212> TYPE: DNA
<213> ORGANISM: Streptococcus pneumoniae
<220> FEATURE:
<221> NAME/KEY: CDS
<222> LOCATION: (1)...(1179)

<400> SEQUENCE: 1
```

```
atg gcc cta cca act att gcc att gta gga cgt ccc aat gtt ggg aaa    48
Met Ala Leu Pro Thr Ile Ala Ile Val Gly Arg Pro Asn Val Gly Lys
 1               5                  10                  15 tca acc cta ttt aat cgg atc gct ggt gag cga atc tcc att gta gaa    96
Ser Thr Leu Phe Asn Arg Ile Ala Gly Glu Arg Ile Ser Ile Val Glu
             20                  25                  30 gat gtc gaa gga gtg aca cgt gac cgt att tat gca acg ggt gag tgg   144
Asp Val Glu Gly Val Thr Arg Asp Arg Ile Tyr Ala Thr Gly Glu Trp
         35                  40                  45 ctc aat cgt tct ttt agc atg att gat aca gga gga att gat gat gtc   192
Leu Asn Arg Ser Phe Ser Met Ile Asp Thr Gly Gly Ile Asp Asp Val
     50                  55                  60 gat gct cct ttc atg gaa caa atc aag cac cag gca gaa att gcc atg   240
Asp Ala Pro Phe Met Glu Gln Ile Lys His Gln Ala Glu Ile Ala Met
 65                  70                  75                  80 gaa gaa gca gat gtt atc gtc ttt gtc gtg tcc ggt aag gaa gga att   288
Glu Glu Ala Asp Val Ile Val Phe Val Val Ser Gly Lys Glu Gly Ile
                 85                  90                  95 acc gat gca gac gaa tac gta gcc cgt aag ctt tat aag acc cac aaa   336
Thr Asp Ala Asp Glu Tyr Val Ala Arg Lys Leu Tyr Lys Thr His Lys
            100                 105                 110 cca gtt atc ctc gca gtt aac aag gtg gac aac cct gag atg cga aat   384
Pro Val Ile Leu Ala Val Asn Lys Val Asp Asn Pro Glu Met Arg Asn
        115                 120                 125 gat atc tat gat ttc tat gcc ctc ggt ttg ggt gaa cca ctg cct atc   432
Asp Ile Tyr Asp Phe Tyr Ala Leu Gly Leu Gly Glu Pro Leu Pro Ile
    130                 135                 140 tca tct gtc cat ggt atc ggt aca ggg gat gta cta gat gcg att gtg   480
Ser Ser Val His Gly Ile Gly Thr Gly Asp Val Leu Asp Ala Ile Val
145                 150                 155                 160 gaa aac ctt cca aat gaa tat gaa gaa gaa aat cca gat gtc att aag   528
Glu Asn Leu Pro Asn Glu Tyr Glu Glu Glu Asn Pro Asp Val Ile Lys
                165                 170                 175 ttt agc ttg att ggt cgt cct aac gtt gga aaa tca agc ttg att aat   576
Phe Ser Leu Ile Gly Arg Pro Asn Val Gly Lys Ser Ser Leu Ile Asn
            180                 185                 190 gct atc ttg gga gaa gac cgt gtc att gcc agt cct gtt gct gga aca   624
Ala Ile Leu Gly Glu Asp Arg Val Ile Ala Ser Pro Val Ala Gly Thr
        195                 200                 205 act cgt gac gct att gat acc cac ttt aca gat aca gat ggt caa gag   672
Thr Arg Asp Ala Ile Asp Thr His Phe Thr Asp Thr Asp Gly Gln Glu
    210                 215                 220 ttt acc atg att gat acg gct ggt atg cgt aag tct ggt aag gtt tat   720
Phe Thr Met Ile Asp Thr Ala Gly Met Arg Lys Ser Gly Lys Val Tyr
225                 230                 235                 240 gaa aat act gag aag tac tct gtc atg cgt gcc atg cgt gct att gac   768
Glu Asn Thr Glu Lys Tyr Ser Val Met Arg Ala Met Arg Ala Ile Asp
                245                 250                 255 cgt tca gat gtg gtc tta atg gtc atc aat gcg gaa gag ggg att cgt   816
Arg Ser Asp Val Val Leu Met Val Ile Asn Ala Glu Glu Gly Ile Arg
            260                 265                 270 gaa tac gac aag cgt atc gct gga ttt gct cat gaa gct ggt aaa ggg   864
Glu Tyr Asp Lys Arg Ile Ala Gly Phe Ala His Glu Ala Gly Lys Gly
        275                 280                 285 atg att atc gtg gtc aac aag tgg gat acg ctt gaa aaa gat aac cac   912
Met Ile Ile Val Val Asn Lys Trp Asp Thr Leu Glu Lys Asp Asn His
    290                 295                 300 act atg aaa aac tgg gaa gaa gat atc cgt gag cag ttc caa tac ctg   960
Thr Met Lys Asn Trp Glu Glu Asp Ile Arg Glu Gln Phe Gln Tyr Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 305 |     |     |     | 310 |     |     |     | 315 |     |     |     | 320 |     |     |     |      |
| cct | tac | gca | ccg | att | atc | ttt | gta | tca | gct | tta | acc | aag | caa | cgt | ctc | 1008 |
| Pro | Tyr | Ala | Pro | Ile | Ile | Phe | Val | Ser | Ala | Leu | Thr | Lys | Gln | Arg | Leu |      |
|     |     |     |     | 325 |     |     |     |     |     | 330 |     |     |     | 335 |     |      |
| cac | aaa | ctt | cct | gag | atg | att | aag | caa | atc | agc | gaa | agt | caa | aat | aca | 1056 |
| His | Lys | Leu | Pro | Glu | Met | Ile | Lys | Gln | Ile | Ser | Glu | Ser | Gln | Asn | Thr |      |
|     |     |     | 340 |     |     |     |     | 345 |     |     |     |     | 350 |     |     |      |
| cgt | att | cca | tca | gct | gtc | ttg | aac | gat | gtc | atc | atg | gat | gcc | att | gcc | 1104 |
| Arg | Ile | Pro | Ser | Ala | Val | Leu | Asn | Asp | Val | Ile | Met | Asp | Ala | Ile | Ala |      |
|     |     | 355 |     |     |     |     | 360 |     |     |     |     | 365 |     |     |     |      |
| atc | aac | cca | aca | ccg | aca | gac | aaa | gga | aaa | cgt | ctc | aag | att | ttc | tat | 1152 |
| Ile | Asn | Pro | Thr | Pro | Thr | Asp | Lys | Gly | Lys | Arg | Leu | Lys | Ile | Phe | Tyr |      |
|     | 370 |     |     |     |     | 375 |     |     |     |     | 380 |     |     |     |     |      |
| gcg | acc | caa | gtg | gca | acc | aaa | cca | cca | ac  |     |     |     |     |     |     | 1181 |
| Ala | Thr | Gln | Val | Ala | Thr | Lys | Pro | Pro |     |     |     |     |     |     |     |      |
| 385 |     |     |     |     | 390 |     |     |     |     |     |     |     |     |     |     |      |

<210> SEQ ID NO 2
<211> LENGTH: 393
<212> TYPE: PRT
<213> ORGANISM: Streptococcus pneumoniae

<400> SEQUENCE: 2

Met Ala Leu Pro Thr Ile Ala Ile Val Gly Arg Pro Asn Val Gly Lys
 1               5                  10                  15

Ser Thr Leu Phe Asn Arg Ile Ala Gly Glu Arg Ile Ser Ile Val Glu
            20                  25                  30

Asp Val Glu Gly Val Thr Arg Asp Arg Ile Tyr Ala Thr Gly Glu Trp
        35                  40                  45

Leu Asn Arg Ser Phe Ser Met Ile Asp Thr Gly Gly Ile Asp Asp Val
    50                  55                  60

Asp Ala Pro Phe Met Glu Gln Ile Lys His Gln Ala Glu Ile Ala Met
65                  70                  75                  80

Glu Glu Ala Asp Val Ile Val Phe Val Val Ser Gly Lys Glu Gly Ile
                85                  90                  95

Thr Asp Ala Asp Glu Tyr Val Ala Arg Lys Leu Tyr Lys Thr His Lys
            100                 105                 110

Pro Val Ile Leu Ala Val Asn Lys Val Asp Asn Pro Glu Met Arg Asn
        115                 120                 125

Asp Ile Tyr Asp Phe Tyr Ala Leu Gly Leu Gly Glu Pro Leu Pro Ile
    130                 135                 140

Ser Ser Val His Gly Ile Gly Thr Gly Asp Val Leu Asp Ala Ile Val
145                 150                 155                 160

Glu Asn Leu Pro Asn Glu Tyr Glu Glu Asn Pro Asp Val Ile Lys
                165                 170                 175

Phe Ser Leu Ile Gly Arg Pro Asn Val Gly Lys Ser Ser Leu Ile Asn
            180                 185                 190

Ala Ile Leu Gly Glu Asp Arg Val Ile Ala Ser Pro Val Ala Gly Thr
        195                 200                 205

Thr Arg Asp Ala Ile Asp Thr His Phe Thr Thr Asp Gly Gln Glu
    210                 215                 220

Phe Thr Met Ile Asp Thr Ala Gly Met Arg Lys Ser Gly Lys Val Tyr
225                 230                 235                 240

Glu Asn Thr Glu Lys Tyr Ser Val Met Arg Ala Met Arg Ala Ile Asp
                245                 250                 255

Arg Ser Asp Val Val Leu Met Val Ile Asn Ala Glu Glu Gly Ile Arg

-continued

|   |   |   |   |   | 260 |   |   |   | 265 |   |   |   | 270 |   |
|---|---|---|---|---|---|---|---|---|---|---|---|---|---|---|

Glu Tyr Asp Lys Arg Ile Ala Gly Phe Ala His Glu Ala Gly Lys Gly
            275                 280                 285

Met Ile Ile Val Val Asn Lys Trp Asp Thr Leu Glu Lys Asp Asn His
    290                 295                 300

Thr Met Lys Asn Trp Glu Glu Asp Ile Arg Glu Gln Phe Gln Tyr Leu
305                 310                 315                 320

Pro Tyr Ala Pro Ile Ile Phe Val Ser Ala Leu Thr Lys Gln Arg Leu
                325                 330                 335

His Lys Leu Pro Glu Met Ile Lys Gln Ile Ser Glu Ser Gln Asn Thr
            340                 345                 350

Arg Ile Pro Ser Ala Val Leu Asn Asp Val Ile Met Asp Ala Ile Ala
            355                 360                 365

Ile Asn Pro Thr Pro Thr Asp Lys Gly Lys Arg Leu Lys Ile Phe Tyr
    370                 375                 380

Ala Thr Gln Val Ala Thr Lys Pro Pro
385                 390

<210> SEQ ID NO 3
<211> LENGTH: 1181
<212> TYPE: DNA
<213> ORGANISM: Streptococcus pneumoniae

<400> SEQUENCE: 3

| gttggtggtt tggttgccac ttgggtcgca tagaaatct tgagacgttt tcctttgtct | 60 |
|---|---|
| gtcggtgttg ggttgatggc aatggcatcc atgatgacat cgttcaagac agctgatgga | 120 |
| atacgtgtat tttgactttc gctgatttgc ttaatcatct caggaagttt gtggagacgt | 180 |
| tgcttggtta aagctgatac aaagataatc ggtgcgtaag gcaggtattg aactgctca | 240 |
| cggatatctt cttcccagtt tttcatagtg tggttatctt tttcaagcgt atcccacttg | 300 |
| ttgaccacga taatcatccc tttaccagct tcatgagcaa atccagcgat acgcttgtcg | 360 |
| tattcacgaa tcccctcttc cgcattgatg accattaaga ccacatctga acggtcaata | 420 |
| gcacgcatgg cacgcatgac agagtacttc tcagtatttt cataaacctt accagactta | 480 |
| cgcataccag ccgtatcaat catggtaaac tcttgaccat ctgtatctgt aaagtgggta | 540 |
| tcaatagcgt cacgagttgt tccagcaaca ggactggcaa tgacacggtc ttctcccaag | 600 |
| atagcattaa tcaagcttga ttttccaacg ttaggacgac caatcaagct aaacttaatg | 660 |
| acatctggat tttcttcttc atattcattt ggaaggtttt ccacaatcgc atctagtaca | 720 |
| tcccctgtac cgataccatg gacagatgag ataggcagtg ttcacccaa accgagggca | 780 |
| tagaaatcat agatatcatt tcgcatctca gggttgtcca ccttgttaac tgcgaggata | 840 |
| actggtttgt gggtcttata aagcttacgg gctacgtatt cgtctgcatc ggtaattcct | 900 |
| tccttaccgg acacgacaaa gacgataaca tctgcttctt ccatggcaat ttctgcctgg | 960 |
| tgcttgattt gttccatgaa aggagcatcg acatcatcaa ttcctcctgt atcaatcatg | 1020 |
| ctaaaagaac gattgagcca ctcacccgtt gcataaatac ggtcacgtgt cactccttcg | 1080 |
| acatcttcta caatggagat tcgctcacca gcgatccgat taaatagggt tgatttccca | 1140 |
| acattgggac gtcctacaat ggcaatagtt ggtagggcca t | 1181 |

<210> SEQ ID NO 4
<211> LENGTH: 1403
<212> TYPE: DNA
<213> ORGANISM: Streptococcus pneumoniae -continued

```
<220> FEATURE:
<221> NAME/KEY: CDS
<222> LOCATION: (14)...(1321)

<400> SEQUENCE: 4
aaagtgagaa att atg gcc cta cca act att gcc att gta gga cgt ccc          49
            Met Ala Leu Pro Thr Ile Ala Ile Val Gly Arg Pro
            1               5                   10 aat gtt ggg aaa tca acc cta ttt aat cgg atc gct ggt gag cga atc         97
Asn Val Gly Lys Ser Thr Leu Phe Asn Arg Ile Ala Gly Glu Arg Ile
        15                  20                  25 tcc att gta gaa gat gtc gaa gga gtg aca cgt gac cgt att tat gca        145
Ser Ile Val Glu Asp Val Glu Gly Val Thr Arg Asp Arg Ile Tyr Ala
    30                  35                  40 acg ggt gag tgg ctc aat cgt tct ttt agc atg att gat aca gga gga        193
Thr Gly Glu Trp Leu Asn Arg Ser Phe Ser Met Ile Asp Thr Gly Gly
45                  50                  55                  60 att gat gat gtc gat gct cct ttc atg gaa caa atc aag cac cag gca        241
Ile Asp Asp Val Asp Ala Pro Phe Met Glu Gln Ile Lys His Gln Ala
                65                  70                  75 gaa att gcc atg gaa gaa gca gat gtt atc gtc ttt gtc gtg tcc ggt        289
Glu Ile Ala Met Glu Glu Ala Asp Val Ile Val Phe Val Val Ser Gly
            80                  85                  90 aag gaa gga att acc gat gca gac gaa tac gta gcc cgt aag ctt tat        337
Lys Glu Gly Ile Thr Asp Ala Asp Glu Tyr Val Ala Arg Lys Leu Tyr
        95                  100                 105 aag acc cac aaa cca gtt atc ctc gca gtt aac aag gtg gac aac cct        385
Lys Thr His Lys Pro Val Ile Leu Ala Val Asn Lys Val Asp Asn Pro
    110                 115                 120 gag atg cga aat gat atc tat gat ttc tat gcc ctc ggt ttg ggt gaa        433
Glu Met Arg Asn Asp Ile Tyr Asp Phe Tyr Ala Leu Gly Leu Gly Glu
125                 130                 135                 140 cca ctg cct atc tca tct gtc cat ggt atc ggt aca ggg gat gta cta        481
Pro Leu Pro Ile Ser Ser Val His Gly Ile Gly Thr Gly Asp Val Leu
                145                 150                 155 gat gcg att gtg gaa aac ctt cca aat gaa tat gaa gaa gaa aat cca        529
Asp Ala Ile Val Glu Asn Leu Pro Asn Glu Tyr Glu Glu Glu Asn Pro
            160                 165                 170 gat gtc att aag ttt agc ttg att ggt cgt cct aac gtt gga aaa tca        577
Asp Val Ile Lys Phe Ser Leu Ile Gly Arg Pro Asn Val Gly Lys Ser
        175                 180                 185 agc ttg att aat gct atc ttg gga gaa gac cgt gtc att gcc agt cct        625
Ser Leu Ile Asn Ala Ile Leu Gly Glu Asp Arg Val Ile Ala Ser Pro
    190                 195                 200 gtt gct gga aca act cgt gac gct att gat acc cac ttt aca gat aca        673
Val Ala Gly Thr Thr Arg Asp Ala Ile Asp Thr His Phe Thr Asp Thr
205                 210                 215                 220 gat ggt caa gag ttt acc atg att gat acg gct ggt atg cgt aag tct        721
Asp Gly Gln Glu Phe Thr Met Ile Asp Thr Ala Gly Met Arg Lys Ser
                225                 230                 235 ggt aag gtt tat gaa aat act gag aag tac tct gtc atg cgt gcc atg        769
Gly Lys Val Tyr Glu Asn Thr Glu Lys Tyr Ser Val Met Arg Ala Met
            240                 245                 250 cgt gct att gac cgt tca gat gtg gtc tta atg gtc atc aat gcg gaa        817
Arg Ala Ile Asp Arg Ser Asp Val Val Leu Met Val Ile Asn Ala Glu
        255                 260                 265 gag ggg att cgt gaa tac gac aag cgt atc gct gga ttt gct cat gaa        865
Glu Gly Ile Arg Glu Tyr Asp Lys Arg Ile Ala Gly Phe Ala His Glu
    270                 275                 280 gct ggt aaa ggg atg att atc gtg gtc aac aag tgg gat acg ctt gaa        913
Ala Gly Lys Gly Met Ile Ile Val Val Asn Lys Trp Asp Thr Leu Glu
```

-continued

```
Ala Gly Lys Gly Met Ile Ile Val Val Asn Lys Trp Asp Thr Leu Glu
285                 290                 295                 300 aaa gat aac cac act atg aaa aac tgg gaa gaa gat atc cgt gag cag     961
Lys Asp Asn His Thr Met Lys Asn Trp Glu Glu Asp Ile Arg Glu Gln
                305                 310                 315 ttc caa tac ctg cct tac gca ccg att atc ttt gta tca gct tta acc    1009
Phe Gln Tyr Leu Pro Tyr Ala Pro Ile Ile Phe Val Ser Ala Leu Thr
                320                 325                 330 aag caa cgt ctc cac aaa ctt cct gag atg att aag caa atc agc gaa    1057
Lys Gln Arg Leu His Lys Leu Pro Glu Met Ile Lys Gln Ile Ser Glu
            335                 340                 345 agt caa aat aca cgt att cca tca gct gtc ttg aac gat gtc atc atg    1105
Ser Gln Asn Thr Arg Ile Pro Ser Ala Val Leu Asn Asp Val Ile Met
        350                 355                 360 gat gcc att gcc atc aac cca aca ccg aca gac aaa gga aaa cgt ctc    1153
Asp Ala Ile Ala Ile Asn Pro Thr Pro Thr Asp Lys Gly Lys Arg Leu
365                 370                 375                 380 aag att ttc tat gcg acc caa gtg gca acc aaa cca cca acc ttt gtc    1201
Lys Ile Phe Tyr Ala Thr Gln Val Ala Thr Lys Pro Pro Thr Phe Val
                385                 390                 395 atc ttt gtc aat gaa gaa gaa ctc atg cac ttt tct tac ctg cgt ttc    1249
Ile Phe Val Asn Glu Glu Glu Leu Met His Phe Ser Tyr Leu Arg Phe
                400                 405                 410 ttg gaa aat caa atc cgc aag gcc ttt gtt ttt gag gga aca ccg att    1297
Leu Glu Asn Gln Ile Arg Lys Ala Phe Val Phe Glu Gly Thr Pro Ile
            415                 420                 425 cat ctc atc gca aga aaa cgc aaa taaaaaagta gaatctggaa tgacagttcc   1351
His Leu Ile Ala Arg Lys Arg Lys
        430                 435 ggattttttt gatataataa aataatagaa aacgctatca aaagaagggg gg          1403

<210> SEQ ID NO 5
<211> LENGTH: 436
<212> TYPE: PRT
<213> ORGANISM: Streptococcus pneumoniae

<400> SEQUENCE: 5

Met Ala Leu Pro Thr Ile Ala Ile Val Gly Arg Pro Asn Val Gly Lys
1               5                   10                  15

Ser Thr Leu Phe Asn Arg Ile Ala Gly Glu Arg Ile Ser Ile Val Glu
                20                  25                  30

Asp Val Glu Gly Val Thr Arg Asp Arg Ile Tyr Ala Thr Gly Glu Trp
            35                  40                  45

Leu Asn Arg Ser Phe Ser Met Ile Asp Thr Gly Gly Ile Asp Asp Val
        50                  55                  60

Asp Ala Pro Phe Met Glu Gln Ile Lys His Gln Ala Glu Ile Ala Met
65                  70                  75                  80

Glu Glu Ala Asp Val Ile Val Phe Val Val Ser Gly Lys Glu Gly Ile
                85                  90                  95

Thr Asp Ala Asp Glu Tyr Val Ala Arg Lys Leu Tyr Lys Thr His Lys
                100                 105                 110

Pro Val Ile Leu Ala Val Asn Lys Val Asp Asn Pro Glu Met Arg Asn
            115                 120                 125

Asp Ile Tyr Asp Phe Tyr Ala Leu Gly Leu Gly Glu Pro Leu Pro Ile
        130                 135                 140

Ser Ser Val His Gly Ile Gly Thr Gly Asp Val Leu Asp Ala Ile Val
145                 150                 155                 160
```

-continued

Glu Asn Leu Pro Asn Glu Tyr Glu Glu Asn Pro Asp Val Ile Lys
                165                 170                 175

Phe Ser Leu Ile Gly Arg Pro Asn Val Gly Lys Ser Ser Leu Ile Asn
            180                 185                 190

Ala Ile Leu Gly Glu Asp Arg Val Ile Ala Ser Pro Val Ala Gly Thr
        195                 200                 205

Thr Arg Asp Ala Ile Asp Thr His Phe Thr Asp Thr Asp Gly Gln Glu
    210                 215                 220

Phe Thr Met Ile Asp Thr Ala Gly Met Arg Lys Ser Gly Lys Val Tyr
225                 230                 235                 240

Glu Asn Thr Glu Lys Tyr Ser Val Met Arg Ala Met Arg Ala Ile Asp
                245                 250                 255

Arg Ser Asp Val Val Leu Met Val Ile Asn Ala Glu Glu Gly Ile Arg
            260                 265                 270

Glu Tyr Asp Lys Arg Ile Ala Gly Phe Ala His Glu Ala Gly Lys Gly
        275                 280                 285

Met Ile Ile Val Val Asn Lys Trp Asp Thr Leu Glu Lys Asp Asn His
    290                 295                 300

Thr Met Lys Asn Trp Glu Glu Asp Ile Arg Glu Gln Phe Gln Tyr Leu
305                 310                 315                 320

Pro Tyr Ala Pro Ile Ile Phe Val Ser Ala Leu Thr Lys Gln Arg Leu
                325                 330                 335

His Lys Leu Pro Glu Met Ile Lys Gln Ile Ser Glu Ser Gln Asn Thr
            340                 345                 350

Arg Ile Pro Ser Ala Val Leu Asn Asp Val Ile Met Asp Ala Ile Ala
        355                 360                 365

Ile Asn Pro Thr Pro Thr Asp Lys Gly Lys Arg Leu Lys Ile Phe Tyr
    370                 375                 380

Ala Thr Gln Val Ala Thr Lys Pro Pro Thr Phe Val Ile Phe Val Asn
385                 390                 395                 400

Glu Glu Glu Leu Met His Phe Ser Tyr Leu Arg Phe Leu Glu Asn Gln
                405                 410                 415

Ile Arg Lys Ala Phe Val Phe Glu Gly Thr Pro Ile His Leu Ile Ala
            420                 425                 430

Arg Lys Arg Lys
        435

<210> SEQ ID NO 6
<211> LENGTH: 1403
<212> TYPE: DNA
<213> ORGANISM: Streptococcus pneumoniae

<400> SEQUENCE: 6
ccccccttct tttgatagcg ttttctatta ttttattata tcaaaaaaat ccggaactgt      60
cattccagat tctactttt tatttgcgtt ttcttgcgat gagatgaatc ggtgttccct     120
caaaaacaaa ggccttgcgg atttgatttt ccaagaaacg caggtaagaa aagtgcatga     180
gttcttcttc attgacaaag atgacaaagg ttggtggttt ggttgccact tgggtcgcat     240
agaaaatctt gagacgtttt cctttgtctg tcggtgttgg gttgatggca atggcatcca     300
tgatgacatc gttcaagaca gctgatggaa tacgtgtatt ttgactttcg ctgatttgct     360
taatcatctc aggaagtttg tggagacgtt gcttggttaa agctgataca agataatcg     420
gtgcgtaagg caggtattgg aactgctcac ggatatcttc ttcccagttt ttcatagtgt     480
ggttatcttt ttcaagcgta tcccacttgt tgaccacgat aatcatccct ttaccagctt     540

-continued

```
catgagcaaa tccagcgata cgcttgtcgt attcacgaat cccctcttcc gcattgatga    600
ccattaagac cacatctgaa cggtcaatag cacgcatggc acgcatgaca gagtacttct    660
cagtattttc ataaacctta ccagacttac gcataccagc cgtatcaatc atggtaaact    720
cttgaccatc tgtatctgta aagtgggtat caatagcgtc acgagttgtt ccagcaacag    780
gactggcaat gacacggtct ctcccaaga tagcattaat caagcttgat tttccaacgt     840
taggacgacc aatcaagcta aacttaatga catctggatt ttcttcttca tattcatttg    900
gaaggttttc cacaatcgca tctagtacat ccctgtacc gataccatgg acagatgaga     960
taggcagtgg ttcacccaaa ccgagggcat agaaatcata gatatcattt cgcatctcag   1020
ggttgtccac cttgttaact gcgaggataa ctggtttgtg ggtcttataa agcttacggg   1080
ctacgtattc gtctgcatcg gtaattcctt ccttaccgga cacgacaaag acgataacat   1140
ctgcttcttc catggcaatt tctgcctggt gcttgatttg ttccatgaaa ggagcatcga   1200
catcatcaat tcctcctgta tcaatcatgc taaaagaacg attgagccac tcaccgttg    1260 cataaatacg gtcacgtgtc actccttcga catcttctac aatggagatt cgctcaccag   1320
cgatccgatt aaatagggtt gatttcccaa cattgggacg tcctacaatg caatagttg    1380 gtagggccat aatttctcac ttt                                           1403
```

<210> SEQ ID NO 7
<211> LENGTH: 930
<212> TYPE: DNA
<213> ORGANISM: Streptococcus pneumoniae
<220> FEATURE:
<221> NAME/KEY: CDS
<222> LOCATION: (1)...(927)

<400> SEQUENCE: 7

```
atg gat att caa ttt tta gga acg ggg gct ggt cag ccc tct aaa gct     48
Met Asp Ile Gln Phe Leu Gly Thr Gly Ala Gly Gln Pro Ser Lys Ala
 1               5                  10                  15 cgc aac gtt tca agt ctc gcc ctg aaa ctt ttg gac gag att aac gaa    96
Arg Asn Val Ser Ser Leu Ala Leu Lys Leu Leu Asp Glu Ile Asn Glu
            20                  25                  30 gtt tgg ctc ttt gac tgt gga gaa ggt acg caa aat cgc att ctg gaa   144
Val Trp Leu Phe Asp Cys Gly Glu Gly Thr Gln Asn Arg Ile Leu Glu
        35                  40                  45 acc aca att cga cca cgt aag gtc agt aaa atc ttt att acc cat ctg   192
Thr Thr Ile Arg Pro Arg Lys Val Ser Lys Ile Phe Ile Thr His Leu
    50                  55                  60 cat gga gac cac att ttt ggt ttg cca ggt ttc ctt tct agc cgt gcc   240
His Gly Asp His Ile Phe Gly Leu Pro Gly Phe Leu Ser Ser Arg Ala
65                  70                  75                  80 ttt cag gcc aat gaa gag cag aca gat ttg gaa atc tac gga cct caa   288
Phe Gln Ala Asn Glu Glu Gln Thr Asp Leu Glu Ile Tyr Gly Pro Gln
                85                  90                  95 gga atc aag tca ttt gtc tta acc agc ctt cgt gtg tca ggt tct cgt   336
Gly Ile Lys Ser Phe Val Leu Thr Ser Leu Arg Val Ser Gly Ser Arg
            100                 105                 110 ctg ccc tac cgc att cat ttc cat gag ttt gac caa gat tct ctg ggt   384
Leu Pro Tyr Arg Ile His Phe His Glu Phe Asp Gln Asp Ser Leu Gly
        115                 120                 125 aaa att ctt gaa acc gat aaa ttc act gtg tat gca gag gag ctg gac   432
Lys Ile Leu Glu Thr Asp Lys Phe Thr Val Tyr Ala Glu Glu Leu Asp
    130                 135                 140 cac act att ttc tgt gtt ggc tat cgt gtc atg caa aag gat cta gaa   480
```

```
His Thr Ile Phe Cys Val Gly Tyr Arg Val Met Gln Lys Asp Leu Glu
145                 150                 155                 160 ggg acg ctg gat gct gaa aaa ctc aag gct gct ggt gtt ccg ttc ggc      528
Gly Thr Leu Asp Ala Glu Lys Leu Lys Ala Ala Gly Val Pro Phe Gly
                165                 170                 175 cca ctt ttt ggt aaa atc aaa aac ggc cag gat ctt gtt ttg gaa gac      576
Pro Leu Phe Gly Lys Ile Lys Asn Gly Gln Asp Leu Val Leu Glu Asp
            180                 185                 190 gga act gaa atc aag gca gca gac tat atc tca gcg cca cgt cca ggt      624
Gly Thr Glu Ile Lys Ala Ala Asp Tyr Ile Ser Ala Pro Arg Pro Gly
        195                 200                 205 aag att atc act att tta gga gac act cga aaa acg ggt gcc agt gtg      672
Lys Ile Ile Thr Ile Leu Gly Asp Thr Arg Lys Thr Gly Ala Ser Val
    210                 215                 220 cgt ctg gct gtt aat gca gat gtc cta gtt cat gag tcc act tat ggc      720
Arg Leu Ala Val Asn Ala Asp Val Leu Val His Glu Ser Thr Tyr Gly
225                 230                 235                 240 aag ggt gat gaa aaa att gct cgt aac cat ggt cac tca act aat atg      768
Lys Gly Asp Glu Lys Ile Ala Arg Asn His Gly His Ser Thr Asn Met
                245                 250                 255 caa gct gca caa gta gcg gta gaa gca ggt gcc aaa cgc ctc cta ctc      816
Gln Ala Ala Gln Val Ala Val Glu Ala Gly Ala Lys Arg Leu Leu Leu
            260                 265                 270 aac cat atc agt gcc cgt ttc ctc tca aaa gat att agc aaa ctc aag      864
Asn His Ile Ser Ala Arg Phe Leu Ser Lys Asp Ile Ser Lys Leu Lys
        275                 280                 285 aaa gac gct gcc aca att ttt gaa aat gtc cat gtg gtc aaa gac ttg      912
Lys Asp Ala Ala Thr Ile Phe Glu Asn Val His Val Val Lys Asp Leu
    290                 295                 300 gaa gaa gtg gaa atc tag                                              930
Glu Glu Val Glu Ile
305

<210> SEQ ID NO 8
<211> LENGTH: 309
<212> TYPE: PRT
<213> ORGANISM: Streptococcus pneumoniae

<400> SEQUENCE: 8

Met Asp Ile Gln Phe Leu Gly Thr Gly Ala Gly Gln Pro Ser Lys Ala
1               5                   10                  15

Arg Asn Val Ser Ser Leu Ala Leu Lys Leu Leu Asp Glu Ile Asn Glu
                20                  25                  30

Val Trp Leu Phe Asp Cys Gly Glu Gly Thr Gln Asn Arg Ile Leu Glu
            35                  40                  45

Thr Thr Ile Arg Pro Arg Lys Val Ser Lys Ile Phe Ile Thr His Leu
        50                  55                  60

His Gly Asp His Ile Phe Gly Leu Pro Gly Phe Leu Ser Ser Arg Ala
65                  70                  75                  80

Phe Gln Ala Asn Glu Glu Gln Thr Asp Leu Glu Ile Tyr Gly Pro Gln
                85                  90                  95

Gly Ile Lys Ser Phe Val Leu Thr Ser Leu Arg Val Ser Gly Ser Arg
            100                 105                 110

Leu Pro Tyr Arg Ile His Phe His Glu Phe Asp Gln Asp Ser Leu Gly
        115                 120                 125

Lys Ile Leu Glu Thr Asp Lys Phe Thr Val Tyr Ala Glu Glu Leu Asp
    130                 135                 140

His Thr Ile Phe Cys Val Gly Tyr Arg Val Met Gln Lys Asp Leu Glu
```

```
                145                 150                 155                 160
Gly Thr Leu Asp Ala Glu Lys Leu Lys Ala Ala Gly Val Pro Phe Gly
                    165                 170                 175
Pro Leu Phe Gly Lys Ile Lys Asn Gly Gln Asp Leu Val Leu Glu Asp
                180                 185                 190
Gly Thr Glu Ile Lys Ala Ala Asp Tyr Ile Ser Ala Pro Arg Pro Gly
            195                 200                 205
Lys Ile Ile Thr Ile Leu Gly Asp Thr Arg Lys Thr Gly Ala Ser Val
    210                 215                 220
Arg Leu Ala Val Asn Ala Asp Val Leu Val His Glu Ser Thr Tyr Gly
225                 230                 235                 240
Lys Gly Asp Glu Lys Ile Ala Arg Asn His Gly His Ser Thr Asn Met
                245                 250                 255
Gln Ala Ala Gln Val Ala Val Glu Ala Gly Ala Lys Arg Leu Leu Leu
                260                 265                 270
Asn His Ile Ser Ala Arg Phe Leu Ser Lys Asp Ile Ser Lys Leu Lys
            275                 280                 285
Lys Asp Ala Ala Thr Ile Phe Glu Asn Val His Val Lys Asp Leu
    290                 295                 300
Glu Glu Val Glu Ile
305

<210> SEQ ID NO 9
<211> LENGTH: 930
<212> TYPE: DNA
<213> ORGANISM: Streptococcus pneumoniae

<400> SEQUENCE: 9
ctagatttcc acttcttcca agtctttgac cacatggaca ttttcaaaaa ttgtggcagc      60
gtctttcttg agtttgctaa tatcttttga gaggaaacgg gcactgatat ggttgagtag     120
gaggcgtttg gcacctgctt ctaccgctac ttgtgcagct tgcatattag ttgagtgacc     180
atggttacga gcaattttt catcacccct gccataagtg gactcatgaa ctaggacatc      240
tgcattaaca gccagacgca cactggcacc cgttttcga gtgtctccta aaatagtgat      300
aatcttacct ggacgtggcg ctgagatata gtctgctgcc ttgatttcag ttccgtcttc     360
caaaacaaga tcctggccgt ttttgatttt accaaaaagt gggccgaacg gaacaccagc     420
agccttgagt ttttcagcat ccagcgtccc ttctagatcc ttttgcatga cacgatagcc     480
aacacagaaa atagtgtggt ccagctcctc tgcatacaca gtgaatttat cggtttcaag     540
aattttaccc agagaatctt ggtcaaactc atggaaatga atgcgtagg gcagacgaga      600
acctgacaca cgaaggctgg ttaagacaaa tgacttgatt ccttgaggtc cgtagatttc     660
caaatctgtc tgctcttcat tggcctgaaa ggcacggcta gaaaggaaac ctggcaaacc     720
aaaaatgtgg tctccatgca gatgggtaat aaagatttta ctgaccttac gtggtcgaat     780
tgtggtttcc agaatgcgat tttgcgtacc ttctccacag tcaaagagcc aaacttcgtt     840
aatctcgtcc aaaagtttca gggcgagact tgaaacgttg cgagctttag agggctgacc     900
agccccgtt cctaaaaatt gaatatccat                                        930

<210> SEQ ID NO 10
<211> LENGTH: 1311
<212> TYPE: DNA
<213> ORGANISM: Bacillus subtilis
<220> FEATURE:
<221> NAME/KEY: CDS
```

<222> LOCATION: (1)...(1308)

<400> SEQUENCE: 10

```
atg ggt aaa cct gtc gta gcc att gtc ggg aga cca aat gta gga aaa      48
Met Gly Lys Pro Val Val Ala Ile Val Gly Arg Pro Asn Val Gly Lys
 1               5                  10                  15 tcc aca atc ttt aac cgg att gcg gga gaa aga att tca ata gta gaa      96
Ser Thr Ile Phe Asn Arg Ile Ala Gly Glu Arg Ile Ser Ile Val Glu
             20                  25                  30 gat acc cct ggc gtg aca agg gat cgg ata tac agc tcg gct gaa tgg     144
Asp Thr Pro Gly Val Thr Arg Asp Arg Ile Tyr Ser Ser Ala Glu Trp
         35                  40                  45 ctg aat tat gat ttt aat ttg att gat acg ggc ggt att gat atc ggt     192
Leu Asn Tyr Asp Phe Asn Leu Ile Asp Thr Gly Gly Ile Asp Ile Gly
     50                  55                  60 gat gag ccg ttt tta gcg cag att cgc cag caa gct gaa atc gcc atg     240
Asp Glu Pro Phe Leu Ala Gln Ile Arg Gln Gln Ala Glu Ile Ala Met
 65                  70                  75                  80 gat gaa gcg gac gtg att att ttt atg gtg aac ggc cgt gaa ggc gtg     288
Asp Glu Ala Asp Val Ile Ile Phe Met Val Asn Gly Arg Glu Gly Val
                 85                  90                  95 aca gct gct gat gaa gaa gtg gcg aaa att ttg tac cgc aca aaa aag     336
Thr Ala Ala Asp Glu Glu Val Ala Lys Ile Leu Tyr Arg Thr Lys Lys
            100                 105                 110 cct gtt gtt tta gcg gtt aat aaa ctg gat aac aca gaa atg aga gcg     384
Pro Val Val Leu Ala Val Asn Lys Leu Asp Asn Thr Glu Met Arg Ala
        115                 120                 125 aat att tat gat ttt tat tcg cta ggc ttt ggc gag ccg tat cca att     432
Asn Ile Tyr Asp Phe Tyr Ser Leu Gly Phe Gly Glu Pro Tyr Pro Ile
    130                 135                 140 tcg gga aca cac gga ctc gga ctg ggt gat tta ctg gat gcc gtt gca     480
Ser Gly Thr His Gly Leu Gly Leu Gly Asp Leu Leu Asp Ala Val Ala
145                 150                 155                 160 gag cat ttt aaa aac att cct gaa acg aaa tac aat gaa gaa gtt att     528
Glu His Phe Lys Asn Ile Pro Glu Thr Lys Tyr Asn Glu Glu Val Ile
                165                 170                 175 caa ttc tgt ctg atc gga cgt cca aat gtc gga aag tct tca ctt gtg     576
Gln Phe Cys Leu Ile Gly Arg Pro Asn Val Gly Lys Ser Ser Leu Val
            180                 185                 190 aat gcg atg ctc ggc gaa gaa cgc gtt att gtc agc aac gtg gct gga     624
Asn Ala Met Leu Gly Glu Glu Arg Val Ile Val Ser Asn Val Ala Gly
        195                 200                 205 acg aca aga gat gct gtt gat acg tca ttt act tac aac cag cag gag     672
Thr Thr Arg Asp Ala Val Asp Thr Ser Phe Thr Tyr Asn Gln Gln Glu
    210                 215                 220 ttt gtc att gtc gat act gca ggt atg cga aaa aaa ggg aaa gtc tat     720
Phe Val Ile Val Asp Thr Ala Gly Met Arg Lys Lys Gly Lys Val Tyr
225                 230                 235                 240 gaa acg act gag aag tat agt gta ctg cgg gcg cta aaa gcg att gac     768
Glu Thr Thr Glu Lys Tyr Ser Val Leu Arg Ala Leu Lys Ala Ile Asp
                245                 250                 255 cgc tca gaa gtc gtg gcg gtt gtg ctg gat ggc gaa gaa ggc att att     816
Arg Ser Glu Val Val Ala Val Val Leu Asp Gly Glu Glu Gly Ile Ile
            260                 265                 270 gaa cag gac aag cgt atc gcc ggt tat gca cac gaa gcg ggc aag gcc     864
Glu Gln Asp Lys Arg Ile Ala Gly Tyr Ala His Glu Ala Gly Lys Ala
        275                 280                 285 gtc gtc atc gtc gta aac aaa tgg gat gct gtt gac aaa gat gag agc     912
Val Val Ile Val Val Asn Lys Trp Asp Ala Val Asp Lys Asp Glu Ser
    290                 295                 300
```

-continued

```
acg atg aaa gaa ttt gaa gaa aat att cgc gat cat ttt caa ttt ctg      960
Thr Met Lys Glu Phe Glu Glu Asn Ile Arg Asp His Phe Gln Phe Leu
305             310                 315                 320 gat tat gcg cca atc cta ttt atg tct gcc tta acg aaa aaa cgg atc     1008
Asp Tyr Ala Pro Ile Leu Phe Met Ser Ala Leu Thr Lys Lys Arg Ile
            325                 330                 335 cat act ctg atg cct gcg att atc aaa gct agt gaa aat cat tca ctt     1056
His Thr Leu Met Pro Ala Ile Ile Lys Ala Ser Glu Asn His Ser Leu
        340                 345                 350 cga gtt caa aca aac gtc tta aat gat gtc atc atg gac gct gtg gca     1104
Arg Val Gln Thr Asn Val Leu Asn Asp Val Ile Met Asp Ala Val Ala
    355                 360                 365 atg aat ccg aca ccg act cat aac ggt tct cgt ttg aaa att tac tat     1152
Met Asn Pro Thr Pro Thr His Asn Gly Ser Arg Leu Lys Ile Tyr Tyr
370                 375                 380 gcg act caa gtg tcg gta aag ccg cca agc ttc gtt gtg ttt gta aac     1200
Ala Thr Gln Val Ser Val Lys Pro Pro Ser Phe Val Val Phe Val Asn
385                 390                 395                 400 gat ccg gaa ctg atg cat ttt tca tac gaa cgg ttt tta gaa aac cga     1248
Asp Pro Glu Leu Met His Phe Ser Tyr Glu Arg Phe Leu Glu Asn Arg
            405                 410                 415 atc aga gac gcg ttc ggt ttt gag ggg aca cca atc aaa ata ttt gca     1296
Ile Arg Asp Ala Phe Gly Phe Glu Gly Thr Pro Ile Lys Ile Phe Ala
        420                 425                 430 aga gct aga aaa taa                                                 1311
Arg Ala Arg Lys
    435
```

<210> SEQ ID NO 11
<211> LENGTH: 436
<212> TYPE: PRT
<213> ORGANISM: Bacillus subtilis

<400> SEQUENCE: 11

```
Met Gly Lys Pro Val Val Ala Ile Val Gly Arg Pro Asn Val Gly Lys
1               5                   10                  15

Ser Thr Ile Phe Asn Arg Ile Ala Gly Glu Arg Ile Ser Ile Val Glu
            20                  25                  30

Asp Thr Pro Gly Val Thr Arg Asp Arg Ile Tyr Ser Ser Ala Glu Trp
        35                  40                  45

Leu Asn Tyr Asp Phe Asn Leu Ile Asp Thr Gly Gly Ile Asp Ile Gly
    50                  55                  60

Asp Glu Pro Phe Leu Ala Gln Ile Arg Gln Gln Ala Glu Ile Ala Met
65                  70                  75                  80

Asp Glu Ala Asp Val Ile Ile Phe Met Val Asn Gly Arg Glu Gly Val
                85                  90                  95

Thr Ala Ala Asp Glu Glu Val Ala Lys Ile Leu Tyr Arg Thr Lys Lys
            100                 105                 110

Pro Val Val Leu Ala Val Asn Lys Leu Asp Asn Thr Glu Met Arg Ala
        115                 120                 125

Asn Ile Tyr Asp Phe Tyr Ser Leu Gly Phe Gly Glu Pro Tyr Pro Ile
    130                 135                 140

Ser Gly Thr His Gly Leu Gly Leu Gly Asp Leu Leu Asp Ala Val Ala
145                 150                 155                 160

Glu His Phe Lys Asn Ile Pro Glu Thr Lys Tyr Asn Glu Glu Val Ile
                165                 170                 175

Gln Phe Cys Leu Ile Gly Arg Pro Asn Val Gly Lys Ser Ser Leu Val
```

```
                    180                 185                 190
Asn Ala Met Leu Gly Glu Glu Arg Val Ile Val Ser Asn Val Ala Gly
            195                 200                 205
Thr Thr Arg Asp Ala Val Asp Thr Ser Phe Thr Tyr Asn Gln Gln Glu
        210                 215                 220
Phe Val Ile Val Asp Thr Ala Gly Met Arg Lys Lys Gly Lys Val Tyr
225                 230                 235                 240
Glu Thr Thr Glu Lys Tyr Ser Val Leu Arg Ala Leu Lys Ala Ile Asp
                245                 250                 255
Arg Ser Glu Val Val Ala Val Val Leu Asp Gly Glu Gly Ile Ile
            260                 265                 270
Glu Gln Asp Lys Arg Ile Ala Gly Tyr Ala His Glu Ala Gly Lys Ala
        275                 280                 285
Val Val Ile Val Val Asn Lys Trp Asp Ala Val Asp Lys Asp Glu Ser
    290                 295                 300
Thr Met Lys Glu Phe Glu Glu Asn Ile Arg Asp His Phe Gln Phe Leu
305                 310                 315                 320
Asp Tyr Ala Pro Ile Leu Phe Met Ser Ala Leu Thr Lys Lys Arg Ile
                325                 330                 335
His Thr Leu Met Pro Ala Ile Ile Lys Ala Ser Glu Asn His Ser Leu
            340                 345                 350
Arg Val Gln Thr Asn Val Leu Asn Asp Val Ile Met Asp Ala Val Ala
        355                 360                 365
Met Asn Pro Thr Pro Thr His Asn Gly Ser Arg Leu Lys Ile Tyr Tyr
    370                 375                 380
Ala Thr Gln Val Ser Val Lys Pro Pro Ser Phe Val Val Phe Val Asn
385                 390                 395                 400
Asp Pro Glu Leu Met His Phe Ser Tyr Glu Arg Phe Leu Glu Asn Arg
                405                 410                 415
Ile Arg Asp Ala Phe Gly Phe Glu Gly Thr Pro Ile Lys Ile Phe Ala
            420                 425                 430
Arg Ala Arg Lys
        435

<210> SEQ ID NO 12
<211> LENGTH: 1311
<212> TYPE: DNA
<213> ORGANISM: Bacillus subtilis

<400> SEQUENCE: 12
ttattttcta gctcttgcaa atattttgat tggtgtcccc tcaaaaccga acgcgtctct      60
gattcggttt tctaaaaacc gttcgtatga aaatgcatc agttccggat cgtttacaaa     120
cacaacgaag cttggcggct ttaccgacac ttgagtcgca tagtaaattt tcaaacgaga     180
accgttatga gtcggtgtcg gattcattgc cacagcgtcc atgatgacat catttaagac     240
gtttgtttga actcgaagtg aatgattttc actagctttg ataatcgcag gcatcagagt     300
atggatccgt ttttttcgtta aggcagacat aaataggatt ggcgcataat ccagaaattg     360
aaaatgatcg cgaatatttt cttcaaattc tttcatcgtg ctctcatctt tgtcaacagc     420
atcccatttg tttacgacga tgacgacggc cttgcccgct tcgtgtgcat aaccggcgat     480
acgcttgtcc tgttcaataa tgccttcttc gccatccagc acaaccgcca cgacttctga     540
gcggtcaatc gctttagcg cccgcagtac actatacttc tcagtcgttt catagacttt     600
cccttttttt cgcataccctg cagtatcgac aatgacaaac tcctgctggt tgtaagtaaa     660
```

-continued

```
tgacgtatca acagcatctc ttgtcgttcc agccacgttg ctgacaataa cgcgttcttc    720
gccgagcatc gcattcacaa gtgaagactt tccgacattt ggacgtccga tcagacagaa    780
ttgaataact tcttcattgt atttcgtttc aggaatgttt taaaatgct ctgcaacggc     840 atccagtaaa tcacccagtc cgagtccgtg tgttcccgaa attggatacg gctcgccaaa    900
gcctagcgaa taaaaatcat aaatattcgc tctcatttct gtgttatcca gtttattaac    960
cgctaaaaca acaggctttt ttgtgcggta caaaattttc gccacttctt catcagcagc    1020
tgtcacgcct tcacggccgt tcaccataaa aataatcacg tccgcttcat ccatggcgat    1080
ttcagcttgc tggcgaatct gcgctaaaaa cggctcatca ccgatatcaa taccgcccgt    1140
atcaatcaaa ttaaaatcat aattcagcca ttcagccgag ctgtatatcc gatcccttgt    1200
cacgccaggg gtatcttcta ctattgaaat tctttctccc gcaatccggt taagattgt     1260 ggatttttcct acatttggtc tcccgacaat ggctacgaca ggtttacccca t           1311
```

<210> SEQ ID NO 13
<211> LENGTH: 1512
<212> TYPE: DNA
<213> ORGANISM: Escherichia coli
<220> FEATURE:
<221> NAME/KEY: CDS
<222> LOCATION: (1)...(1509)

<400> SEQUENCE: 13

```
gtg cgt tgt ctg atg att tat aaa aat gag gct tta aac atg gta cct     48
Val Arg Cys Leu Met Ile Tyr Lys Asn Glu Ala Leu Asn Met Val Pro
 1               5                  10                  15 gtg gtc gcg ctt gtc ggg cgc cct aac gta gga aaa tcc acg tta ttt     96
Val Val Ala Leu Val Gly Arg Pro Asn Val Gly Lys Ser Thr Leu Phe
             20                  25                  30 aac cgt cta act cgc acc cga gat gcg ctg gtt gcg gat ttc ccg ggt    144
Asn Arg Leu Thr Arg Thr Arg Asp Ala Leu Val Ala Asp Phe Pro Gly
         35                  40                  45 ctg act cgt gac cgt aag tac ggt cgt gcg gaa att gaa ggc cgt gag    192
Leu Thr Arg Asp Arg Lys Tyr Gly Arg Ala Glu Ile Glu Gly Arg Glu
     50                  55                  60 ttt atc tgt att gat acc ggc ggg att gat ggc aca gaa gac ggt gta    240
Phe Ile Cys Ile Asp Thr Gly Gly Ile Asp Gly Thr Glu Asp Gly Val
 65                  70                  75                  80 gaa acc cgc atg gcg gaa cag tcg ctg ctg gcg att gaa gaa gcg gac    288
Glu Thr Arg Met Ala Glu Gln Ser Leu Leu Ala Ile Glu Glu Ala Asp
             85                  90                  95 gtc gta ctg ttt atg gtg gat gcg cgc gcg ggc ctg atg ccg gca gat    336
Val Val Leu Phe Met Val Asp Ala Arg Ala Gly Leu Met Pro Ala Asp
            100                 105                 110 gaa gcg att gcc aaa cat ctg cgc tcc cgt gaa aaa ccg acc ttc ctg    384
Glu Ala Ile Ala Lys His Leu Arg Ser Arg Glu Lys Pro Thr Phe Leu
        115                 120                 125 gtg gca aac aaa act gac ggt ctg gat ccc gat cag gca gtg gtt gat    432
Val Ala Asn Lys Thr Asp Gly Leu Asp Pro Asp Gln Ala Val Val Asp
    130                 135                 140 ttc tac tcg ctt ggt tta ggt gaa atc tac ccg atc gcc gcg tct cac    480
Phe Tyr Ser Leu Gly Leu Gly Glu Ile Tyr Pro Ile Ala Ala Ser His
145                 150                 155                 160 ggt cgt ggc gta tta agt ctg ctg gag cat gtg ctg ctg ccg tgg atg    528
Gly Arg Gly Val Leu Ser Leu Leu Glu His Val Leu Leu Pro Trp Met
                165                 170                 175 gaa gat ctc gca ccg caa gag gaa gtc gac gaa gac gct gaa tac tgg    576
```

```
                Glu Asp Leu Ala Pro Gln Glu Glu Val Asp Glu Asp Ala Glu Tyr Trp
                            180                 185                 190 gcg caa ttt gaa gcg gaa gag aac ggc gaa gaa gaa gag gaa gac gac              624
Ala Gln Phe Glu Ala Glu Glu Asn Gly Glu Glu Glu Glu Glu Asp Asp
            195                 200                 205 ttc gac ccg caa agt ctg ccg atc aaa ctg gcg att gtg ggt cgt ccg              672
Phe Asp Pro Gln Ser Leu Pro Ile Lys Leu Ala Ile Val Gly Arg Pro
        210                 215                 220 aac gta ggt aag tct aca ctc act aac cgt att ctt ggt gaa gag cgc              720
Asn Val Gly Lys Ser Thr Leu Thr Asn Arg Ile Leu Gly Glu Glu Arg
225                 230                 235                 240 gtt gtt gtt tac gac atg cct ggc acg acg cgt gac agc atc tac atc              768
Val Val Val Tyr Asp Met Pro Gly Thr Thr Arg Asp Ser Ile Tyr Ile
                245                 250                 255 cca atg gaa cgc gat gga cgt gag tat gtg ctc att gac acc gct ggc              816
Pro Met Glu Arg Asp Gly Arg Glu Tyr Val Leu Ile Asp Thr Ala Gly
            260                 265                 270 gta cgt aaa cgc ggc aaa atc acc gat gct gta gag aaa ttc tcc gta              864
Val Arg Lys Arg Gly Lys Ile Thr Asp Ala Val Glu Lys Phe Ser Val
        275                 280                 285 atc aaa acg ttg cag gcc att gaa gac gcc aac gtg gtg atg tta gtg              912
Ile Lys Thr Leu Gln Ala Ile Glu Asp Ala Asn Val Val Met Leu Val
    290                 295                 300 att gat gcg cgc gaa ggt att tcc gat cag gat ctc tcg ctg ctg ggc              960
Ile Asp Ala Arg Glu Gly Ile Ser Asp Gln Asp Leu Ser Leu Leu Gly
305                 310                 315                 320 ttt att ctc aat agt ggg cgc tca ctt gtc att gtg gtg aat aag tgg             1008
Phe Ile Leu Asn Ser Gly Arg Ser Leu Val Ile Val Val Asn Lys Trp
                325                 330                 335 gat ggc ctg agt cag gaa gtg aaa gag cag gtg aaa gaa acg ctg gac             1056
Asp Gly Leu Ser Gln Glu Val Lys Glu Gln Val Lys Glu Thr Leu Asp
            340                 345                 350 ttc cgt ctg ggc ttt atc gat ttt gct cgt gtg cac ttt atc tct gcc             1104
Phe Arg Leu Gly Phe Ile Asp Phe Ala Arg Val His Phe Ile Ser Ala
        355                 360                 365 ttg cac ggc agt ggt gtt ggt aac ttg ttt gaa tca gta cgt gaa gcg             1152
Leu His Gly Ser Gly Val Gly Asn Leu Phe Glu Ser Val Arg Glu Ala
    370                 375                 380 tat gac agc tcc acc cgt cgt gtg ggg acc tct atg ctg acg cgc atc             1200
Tyr Asp Ser Ser Thr Arg Arg Val Gly Thr Ser Met Leu Thr Arg Ile
385                 390                 395                 400 atg acg atg gct gtt gaa gat cac caa ccg ccg ctg gta cgc ggt cgt             1248
Met Thr Met Ala Val Glu Asp His Gln Pro Pro Leu Val Arg Gly Arg
                405                 410                 415 cgt gtg aag ctg aaa tat gcc cac gcc ggt ggt tat aac ccg ccg att             1296
Arg Val Lys Leu Lys Tyr Ala His Ala Gly Gly Tyr Asn Pro Pro Ile
            420                 425                 430 gtg gtg att cac ggt aat cag gtg aaa gac ctg cct gat tcc tac aag             1344
Val Val Ile His Gly Asn Gln Val Lys Asp Leu Pro Asp Ser Tyr Lys
        435                 440                 445 cgc tac ttg atg aac tac ttc cgc aaa tcg ctg gac gta atg gga tcg             1392
Arg Tyr Leu Met Asn Tyr Phe Arg Lys Ser Leu Asp Val Met Gly Ser
    450                 455                 460 ccg att cgt att cag ttc aaa gaa ggg gaa aac ccg tat gcg aat aag             1440
Pro Ile Arg Ile Gln Phe Lys Glu Gly Glu Asn Pro Tyr Ala Asn Lys
465                 470                 475                 480 cgt aac acc ctg acg cca acc cag atg cgt aaa cgt aag cgt ctg atg             1488
Arg Asn Thr Leu Thr Pro Thr Gln Met Arg Lys Arg Lys Arg Leu Met
                485                 490                 495
```

```
aag cac atc aag aaa aat aaa taa                                    1512
Lys His Ile Lys Lys Asn Lys
            500
```

<210> SEQ ID NO 14
<211> LENGTH: 503
<212> TYPE: PRT
<213> ORGANISM: Escherichia coli

<400> SEQUENCE: 14

```
Val Arg Cys Leu Met Ile Tyr Lys Asn Glu Ala Leu Asn Met Val Pro
 1               5                  10                  15

Val Val Ala Leu Val Gly Arg Pro Asn Val Gly Lys Ser Thr Leu Phe
            20                  25                  30

Asn Arg Leu Thr Arg Thr Arg Asp Ala Leu Val Ala Asp Phe Pro Gly
        35                  40                  45

Leu Thr Arg Asp Arg Lys Tyr Gly Arg Ala Glu Ile Glu Gly Arg Glu
    50                  55                  60

Phe Ile Cys Ile Asp Thr Gly Gly Ile Asp Gly Thr Glu Asp Gly Val
65                  70                  75                  80

Glu Thr Arg Met Ala Glu Gln Ser Leu Leu Ala Ile Glu Glu Ala Asp
                85                  90                  95

Val Val Leu Phe Met Val Asp Ala Arg Ala Gly Leu Met Pro Ala Asp
            100                 105                 110

Glu Ala Ile Ala Lys His Leu Arg Ser Arg Glu Lys Pro Thr Phe Leu
        115                 120                 125

Val Ala Asn Lys Thr Asp Gly Leu Asp Pro Asp Gln Ala Val Val Asp
    130                 135                 140

Phe Tyr Ser Leu Gly Leu Gly Glu Ile Tyr Pro Ile Ala Ala Ser His
145                 150                 155                 160

Gly Arg Gly Val Leu Ser Leu Leu Glu His Val Leu Leu Pro Trp Met
                165                 170                 175

Glu Asp Leu Ala Pro Gln Glu Glu Val Asp Glu Asp Ala Glu Tyr Trp
            180                 185                 190

Ala Gln Phe Glu Ala Glu Glu Asn Gly Glu Glu Glu Glu Asp Asp
        195                 200                 205

Phe Asp Pro Gln Ser Leu Pro Ile Lys Leu Ala Ile Val Gly Arg Pro
    210                 215                 220

Asn Val Gly Lys Ser Thr Leu Thr Asn Arg Ile Leu Gly Glu Glu Arg
225                 230                 235                 240

Val Val Val Tyr Asp Met Pro Gly Thr Thr Arg Asp Ser Ile Tyr Ile
                245                 250                 255

Pro Met Glu Arg Asp Gly Arg Glu Tyr Val Leu Ile Asp Thr Ala Gly
            260                 265                 270

Val Arg Lys Arg Gly Lys Ile Thr Asp Ala Val Glu Lys Phe Ser Val
        275                 280                 285

Ile Lys Thr Leu Gln Ala Ile Glu Asp Ala Asn Val Val Met Leu Val
    290                 295                 300

Ile Asp Ala Arg Glu Gly Ile Ser Asp Gln Asp Leu Ser Leu Leu Gly
305                 310                 315                 320

Phe Ile Leu Asn Ser Gly Arg Ser Leu Val Ile Val Asn Lys Trp
                325                 330                 335

Asp Gly Leu Ser Gln Glu Val Lys Glu Gln Val Lys Glu Thr Leu Asp
            340                 345                 350

Phe Arg Leu Gly Phe Ile Asp Phe Ala Arg Val His Phe Ile Ser Ala
```

-continued

```
            355                 360                 365
Leu His Gly Ser Gly Val Gly Asn Leu Phe Glu Ser Val Arg Glu Ala
    370                 375                 380

Tyr Asp Ser Ser Thr Arg Arg Val Gly Thr Ser Met Leu Thr Arg Ile
385                 390                 395                 400

Met Thr Met Ala Val Glu Asp His Gln Pro Pro Leu Val Arg Gly Arg
                405                 410                 415

Arg Val Lys Leu Lys Tyr Ala His Ala Gly Gly Tyr Asn Pro Pro Ile
            420                 425                 430

Val Val Ile His Gly Asn Gln Val Lys Asp Leu Pro Asp Ser Tyr Lys
            435                 440                 445

Arg Tyr Leu Met Asn Tyr Phe Arg Lys Ser Leu Asp Val Met Gly Ser
450                 455                 460

Pro Ile Arg Ile Gln Phe Lys Glu Gly Glu Asn Pro Tyr Ala Asn Lys
465                 470                 475                 480

Arg Asn Thr Leu Thr Pro Thr Gln Met Arg Lys Arg Lys Arg Leu Met
                485                 490                 495

Lys His Ile Lys Lys Asn Lys
            500

<210> SEQ ID NO 15
<211> LENGTH: 1512
<212> TYPE: DNA
<213> ORGANISM: Escherichia coli

<400> SEQUENCE: 15
ttatttattt tcttgatgt gcttcatcag acgcttacgt ttacgcatct gggttggcgt      60
cagggtgtta cgcttattcg catacgggtt ttccccttct ttgaactgaa tacgaatcgg    120
cgatcccatt acgtccagcg atttgcggaa gtagttcatc aagtagcgct tgtaggaatc    180
aggcaggtct ttcacctgat taccgtgaat caccacaatc ggcgggttat aaccaccggc    240
gtgggcatat ttcagcttca cacgacgacc gcgtaccagc ggcggttggt gatcttcaac    300
agccatcgtc atgatgcgcg tcagcataga ggtccccaca cgacgggtgg agctgtcata    360
cgcttcacgt actgattcaa acaagttacc aacaccactg ccgtgcaagg cagagataaa    420
gtgcacacga gcaaaatcga taaagcccag acggaagtcc agcgtttctt tcacctgctc    480
tttcacttcc tgactcaggc catcccactt attcaccaca atgacaagtg agcgcccact    540
attgagaata aagcccagca gcgagagatc ctgatcggaa ataccttcgc gcgcatcaat    600
cactaacatc accacgttgg cgtcttcaat ggcctgcaac gttttgatta cggagaattt    660
ctctacagca tcggtgattt tgccgcgttt acgtacgcca gcggtgtcaa tgagcacata    720
ctcacgtcca tcgcgttcca ttgggatgta gatgctgtca cgcgtcgtgc caggcatgtc    780
gtaaacaaca acgcgctctt caccaagaat acggttagtg agtgtagact tacctacgtt    840
cggacgaccc acaatcgcca gtttgatcgg cagactttgc gggtcgaagt cgtcttcctc    900
ttcttcttcg ccgttctctt ccgcttcaaa ttgcgcccag tattcagcgt cttcgtcgac    960
ttcctcttgc ggtgcgagat cttccatcca cggcagcagc acatgctcca gcagacttaa   1020
tacgccacga ccgtgagacg cggcgatcgg gtagatttca cctaaaccaa gcgagtagaa   1080
atcaaccact gcctgatcgg gatccagacc gtcagttttg tttgccacca ggaaggtcgg   1140
tttttcacgg gagcgcagat gtttggcaat cgcttcatct gccggcatca ggcccgcgcg   1200
cgcatccacc ataaacagta cgacgtccgc ttcttcaatc gccagcagcg actgttccgc   1260
```

```
catgcgggtt tctacaccgt cttctgtgcc atcaatcccg ccggtatcaa tacagataaa    1320
ctcacggcct tcaatttccg cacgaccgta cttacggtca cgagtcagac ccgggaaatc    1380
cgcaaccagc gcatctcggg tgcgagttag acggttaaat aacgtggatt ttcctacgtt    1440
agggcgcccg acaagcgcga ccacaggtac catgtttaaa gcctcatttt tataaatcat    1500
cagacaacgc ac                                                        1512

<210> SEQ ID NO 16
<211> LENGTH: 924
<212> TYPE: DNA
<213> ORGANISM: Bacillus subtilis
<220> FEATURE:
<221> NAME/KEY: CDS
<222> LOCATION: (4)...(921)

<400> SEQUENCE: 16 gtg gaa tta ctt ttt tta ggg acg gga gcc ggc atc ccc gcc aag gcg      48
    Glu Leu Leu Phe Leu Gly Thr Gly Ala Gly Ile Pro Ala Lys Ala
    1               5                   10                  15 aga aat gta acg tcg gtg gca tta aaa ttg ctt gaa gaa agg cgt tcg      96
Arg Asn Val Thr Ser Val Ala Leu Lys Leu Leu Glu Glu Arg Arg Ser
                20                  25                  30 gta tgg ctt ttt gac tgc ggg gaa gcc aca cag cat caa att tta cat    144
Val Trp Leu Phe Asp Cys Gly Glu Ala Thr Gln His Gln Ile Leu His
            35                  40                  45 aca acg att aaa cct cgt aaa ata gag aaa atc ttt att aca cac atg    192
Thr Thr Ile Lys Pro Arg Lys Ile Glu Lys Ile Phe Ile Thr His Met
        50                  55                  60 cac ggc gat cat gta tac gga ctt ccg ggg ctt ctg ggg agc cgt tcc    240
His Gly Asp His Val Tyr Gly Leu Pro Gly Leu Leu Gly Ser Arg Ser
65                  70                  75 ttt caa ggc gga gag gac gag ctg aca gtg tac gga cct aaa ggg atc    288
Phe Gln Gly Gly Glu Asp Glu Leu Thr Val Tyr Gly Pro Lys Gly Ile
80                  85                  90                  95 aag gcg ttt att gaa aca agc ctt gcc gtc acg aaa acc cat ttg aca    336
Lys Ala Phe Ile Glu Thr Ser Leu Ala Val Thr Lys Thr His Leu Thr
                100                 105                 110 tat ccg ctt gcg atc cag gaa att gaa gaa gga atc gtg ttt gag gac    384
Tyr Pro Leu Ala Ile Gln Glu Ile Glu Glu Gly Ile Val Phe Glu Asp
            115                 120                 125 gat cag ttt att gtc aca gcg gta tct gtt att cat gga gtg gaa gcc    432
Asp Gln Phe Ile Val Thr Ala Val Ser Val Ile His Gly Val Glu Ala
        130                 135                 140 ttc ggg tac cgt gtg cag gaa aaa gac gta ccg ggt tcc ttg aag gct    480
Phe Gly Tyr Arg Val Gln Glu Lys Asp Val Pro Gly Ser Leu Lys Ala
145                 150                 155 gac gta tta aaa gaa atg aac atc ccg ccc gga cct gta tat cag aaa    528
Asp Val Leu Lys Glu Met Asn Ile Pro Pro Gly Pro Val Tyr Gln Lys
160                 165                 170                 175 atc aaa aaa ggc gaa acg gta acg ctt gaa gac gga cga atc atc aat    576
Ile Lys Lys Gly Glu Thr Val Thr Leu Glu Asp Gly Arg Ile Ile Asn
                180                 185                 190 ggg aat gat ttt ctg gag cct cct aaa aag gga aga tct gtt gtg ttc    624
Gly Asn Asp Phe Leu Glu Pro Pro Lys Lys Gly Arg Ser Val Val Phe
            195                 200                 205 tcc ggt gat acg aga gta agt gac aaa cta aaa gag ctt gcg agg gat    672
Ser Gly Asp Thr Arg Val Ser Asp Lys Leu Lys Glu Leu Ala Arg Asp
        210                 215                 220 tgt gat gtg ctt gtt cat gaa gca acc ttt gct aag gaa gac cgt aaa    720
Cys Asp Val Leu Val His Glu Ala Thr Phe Ala Lys Glu Asp Arg Lys
```

```
              225                 230                 235
ctt gct tat gat tat tat cac agt aca acg gaa caa gcg gct gta aca        768
Leu Ala Tyr Asp Tyr Tyr His Ser Thr Thr Glu Gln Ala Ala Val Thr
240                 245                 250                 255 gcg aaa gaa gca aga gcg aag cag ctc att tta acc cat atc agc gca        816
Ala Lys Glu Ala Arg Ala Lys Gln Leu Ile Leu Thr His Ile Ser Ala
                260                 265                 270 aga tat cag gga gat gct tct ttg gag ctt caa aaa gaa gcg gtt gac        864
Arg Tyr Gln Gly Asp Ala Ser Leu Glu Leu Gln Lys Glu Ala Val Asp
            275                 280                 285 gtt ttc ccc aat agc gtg gcg gca tat gat ttc tta gag gta aac gtc        912
Val Phe Pro Asn Ser Val Ala Ala Tyr Asp Phe Leu Glu Val Asn Val
        290                 295                 300 ccg cga ggc tga                                                        924
Pro Arg Gly
    305

<210> SEQ ID NO 17
<211> LENGTH: 307
<212> TYPE: PRT
<213> ORGANISM: Bacillus subtilis

<400> SEQUENCE: 17

Met Glu Leu Leu Phe Leu Gly Thr Gly Ala Gly Ile Pro Ala Lys Ala
  1               5                  10                  15

Arg Asn Val Thr Ser Val Ala Leu Lys Leu Leu Glu Glu Arg Arg Ser
                 20                  25                  30

Val Trp Leu Phe Asp Cys Gly Glu Ala Thr Gln His Gln Ile Leu His
             35                  40                  45

Thr Thr Ile Lys Pro Arg Lys Ile Glu Lys Ile Phe Ile Thr His Met
 50                  55                  60

His Gly Asp His Val Tyr Gly Leu Pro Gly Leu Leu Gly Ser Arg Ser
 65                  70                  75                  80

Phe Gln Gly Gly Glu Asp Glu Leu Thr Val Tyr Gly Pro Lys Gly Ile
                 85                  90                  95

Lys Ala Phe Ile Glu Thr Ser Leu Ala Val Thr Lys Thr His Leu Thr
            100                 105                 110

Tyr Pro Leu Ala Ile Gln Glu Ile Glu Glu Gly Ile Val Phe Glu Asp
        115                 120                 125

Asp Gln Phe Ile Val Thr Ala Val Ser Val Ile His Gly Val Glu Ala
130                 135                 140

Phe Gly Tyr Arg Val Gln Glu Lys Asp Val Pro Gly Ser Leu Lys Ala
145                 150                 155                 160

Asp Val Leu Lys Glu Met Asn Ile Pro Pro Gly Pro Val Tyr Gln Lys
                165                 170                 175

Ile Lys Lys Gly Glu Thr Val Thr Leu Glu Asp Gly Arg Ile Ile Asn
            180                 185                 190

Gly Asn Asp Phe Leu Glu Pro Pro Lys Lys Gly Arg Ser Val Val Phe
        195                 200                 205

Ser Gly Asp Thr Arg Val Ser Asp Lys Leu Lys Glu Leu Ala Arg Asp
210                 215                 220

Cys Asp Val Leu Val His Glu Ala Thr Phe Ala Lys Glu Asp Arg Lys
225                 230                 235                 240

Leu Ala Tyr Asp Tyr Tyr His Ser Thr Thr Glu Gln Ala Ala Val Thr
                245                 250                 255

Ala Lys Glu Ala Arg Ala Lys Gln Leu Ile Leu Thr His Ile Ser Ala
```

```
                 260                 265                 270
Arg Tyr Gln Gly Asp Ala Ser Leu Glu Leu Gln Lys Glu Ala Val Asp
            275                 280                 285
Val Phe Pro Asn Ser Val Ala Ala Tyr Asp Phe Leu Glu Val Asn Val
        290                 295                 300
Pro Arg Gly
305

<210> SEQ ID NO 18
<211> LENGTH: 924
<212> TYPE: DNA
<213> ORGANISM: Bacillus subtilis

<400> SEQUENCE: 18
tcagcctcgc gggacgttta cctctaagaa atcatatgcc gccacgctat tggggaaaac     60
gtcaaccgct tctttttgaa gctccaaaga agcatctccc tgatatcttg cgctgatatg    120
ggttaaaatg agctgcttcg ctcttgcttc tttcgctgtt acagccgctt gttccgttgt    180
actgtgataa taatcataag caagtttacg gtcttcctta gcaaaggttg cttcatgaac    240
aagcacatca caatccctcg caagctcttt tagtttgtca cttactctcg tatcaccgga    300
gaacacaaca gatcttccct ttttaggagg ctccagaaaa tcattcccat tgatgattcg    360
tccgtcttca agcgttaccg tttcgccttt tttgattttc tgatatacag gtccgggcgg    420
gatgttcatt tcttttaata cgtcagcctt caaggaaccc ggtacgtctt ttcctgcac     480
acggtacccg aaggcttcca ctccatgaat aacagatacc gctgtgacaa taaactgatc    540
gtcctcaaac acgattcctt cttcaatttc ctggatcgca agcggatatg tcaaatgggt    600
tttcgtgacg gcaaggcttg tttcaataaa cgccttgatc cctttaggtc cgtacactgt    660
cagctcgtcc tctccgcctt gaaggaacg gctccccaga agccccggaa gtccgtatac     720
atgatcgccg tgcatgtgtg taataaagat tttctctatt ttacgaggtt taatcgttgt    780
atgtaaaatt tgatgctgtg tggcttcccc gcagtcaaaa agccataccg aacgcctttc    840
ttcaagcaat tttaatgcca ccgacgttac atttctcgcc ttggcgggga tgccggctcc    900
cgtccctaaa aaagtaatt ccac                                            924

<210> SEQ ID NO 19
<211> LENGTH: 936
<212> TYPE: DNA
<213> ORGANISM: Escherichia coli
<220> FEATURE:
<221> NAME/KEY: CDS
<222> LOCATION: (4)...(933)

<400> SEQUENCE: 19 ttg aaa cgt gat gaa ctc atg gaa tta att ttt tta ggt act tca gcc      48
    Lys Arg Asp Glu Leu Met Glu Leu Ile Phe Leu Gly Thr Ser Ala
    1               5                  10                  15 ggt gtg cca acc cgc acg cgc aat gtc acg gca ata ttg ctt aac ctg      96
Gly Val Pro Thr Arg Thr Arg Asn Val Thr Ala Ile Leu Leu Asn Leu
                20                  25                  30 caa cat ccg acc cag agc gga ctt tgg ttg ttt gac tgc ggt gaa ggc     144
Gln His Pro Thr Gln Ser Gly Leu Trp Leu Phe Asp Cys Gly Glu Gly
            35                  40                  45 acc cag cat cag cta ctg cat acc gcc ttt aac cct gga aaa ctg gac     192
Thr Gln His Gln Leu Leu His Thr Ala Phe Asn Pro Gly Lys Leu Asp
        50                  55                  60 aag att ttt atc agt cac ctt cat ggc gat cat ctt ttt ggt tta ccc     240
```

```
                                                                            -continued Lys Ile Phe Ile Ser His Leu His Gly Asp His Leu Phe Gly Leu Pro
 65                  70                  75 ggc ttg ctg tgc agt cgt tct atg tca ggc att atc caa ccc tta acg        288
Gly Leu Leu Cys Ser Arg Ser Met Ser Gly Ile Ile Gln Pro Leu Thr
 80                  85                  90                  95 att tat ggt ccg caa ggt atc cgt gaa ttt gtg gaa acc gcg ctg cgg        336
Ile Tyr Gly Pro Gln Gly Ile Arg Glu Phe Val Glu Thr Ala Leu Arg
                100                 105                 110 att agc ggc tca tgg acc gat tat ccg ctg gaa att gtc gaa att ggc        384
Ile Ser Gly Ser Trp Thr Asp Tyr Pro Leu Glu Ile Val Glu Ile Gly
            115                 120                 125 gct ggc gaa att ctc gat gat ggc ctg cgc aaa gta acc gct tat ccg        432
Ala Gly Glu Ile Leu Asp Asp Gly Leu Arg Lys Val Thr Ala Tyr Pro
        130                 135                 140 ctg gaa cac cca ctg gaa tgt tat ggc tat cgt att gaa gaa cat gat        480
Leu Glu His Pro Leu Glu Cys Tyr Gly Tyr Arg Ile Glu Glu His Asp
    145                 150                 155 aaa ccg ggt gca tta aat gcc cag gca tta aaa gct gct ggc gtg ccg        528
Lys Pro Gly Ala Leu Asn Ala Gln Ala Leu Lys Ala Ala Gly Val Pro
160                 165                 170                 175 cct ggc cca ctg ttt cag gaa tta aaa gcg ggc aaa aca atc acg ctg        576
Pro Gly Pro Leu Phe Gln Glu Leu Lys Ala Gly Lys Thr Ile Thr Leu
                180                 185                 190 gaa gat gga agg cag att aac ggc gca gat tac tta gct gct cca gtg        624
Glu Asp Gly Arg Gln Ile Asn Gly Ala Asp Tyr Leu Ala Ala Pro Val
            195                 200                 205 cca ggt aaa gcg ctc gct att ttc ggc gat acc ggc ccc tgc gat gcc        672
Pro Gly Lys Ala Leu Ala Ile Phe Gly Asp Thr Gly Pro Cys Asp Ala
        210                 215                 220 gca ctt gac ctg gct aaa ggt gtc gat gtc atg gtg cac gaa gcg acg        720
Ala Leu Asp Leu Ala Lys Gly Val Asp Val Met Val His Glu Ala Thr
    225                 230                 235 ctg gat ata acc atg gaa gcc aaa gcc aat agt cgc ggc cat agc tct        768
Leu Asp Ile Thr Met Glu Ala Lys Ala Asn Ser Arg Gly His Ser Ser
240                 245                 250                 255 aca cgc cag gct gcg aca cta gcc cgt gag gct gga gtc ggc aag cta        816
Thr Arg Gln Ala Ala Thr Leu Ala Arg Glu Ala Gly Val Gly Lys Leu
                260                 265                 270 atc att acc cac gtc agc tcg cgc tat gat gac aaa ggt tgt cag cac        864
Ile Ile Thr His Val Ser Ser Arg Tyr Asp Asp Lys Gly Cys Gln His
            275                 280                 285 ctg tta cgt gaa tgc agg tca att ttc ccg gcg act gaa ctg gcg aat        912
Leu Leu Arg Glu Cys Arg Ser Ile Phe Pro Ala Thr Glu Leu Ala Asn
        290                 295                 300 gat ttc acc gtg ttt aac gtt taa                                         936
Asp Phe Thr Val Phe Asn Val
    305                 310

<210> SEQ ID NO 20
<211> LENGTH: 311
<212> TYPE: PRT
<213> ORGANISM: Escherichia coli

<400> SEQUENCE: 20

Met Lys Arg Asp Glu Leu Met Glu Leu Ile Phe Leu Gly Thr Ser Ala
 1               5                  10                  15

Gly Val Pro Thr Arg Thr Arg Asn Val Thr Ala Ile Leu Leu Asn Leu
                20                  25                  30

Gln His Pro Thr Gln Ser Gly Leu Trp Leu Phe Asp Cys Gly Glu Gly
            35                  40                  45
```

```
Thr Gln His Gln Leu Leu His Thr Ala Phe Asn Pro Gly Lys Leu Asp
 50                  55                  60
Lys Ile Phe Ile Ser His Leu His Gly Asp His Leu Phe Gly Leu Pro
 65                  70                  75                  80
Gly Leu Leu Cys Ser Arg Ser Met Ser Gly Ile Ile Gln Pro Leu Thr
                 85                  90                  95
Ile Tyr Gly Pro Gln Gly Ile Arg Glu Phe Val Glu Thr Ala Leu Arg
                100                 105                 110
Ile Ser Gly Ser Trp Thr Asp Tyr Pro Leu Glu Ile Val Glu Ile Gly
                115                 120                 125
Ala Gly Glu Ile Leu Asp Asp Gly Leu Arg Lys Val Thr Ala Tyr Pro
130                 135                 140
Leu Glu His Pro Leu Glu Cys Tyr Gly Tyr Arg Ile Glu Glu His Asp
145                 150                 155                 160
Lys Pro Gly Ala Leu Asn Ala Gln Ala Leu Lys Ala Ala Gly Val Pro
                165                 170                 175
Pro Gly Pro Leu Phe Gln Glu Leu Lys Ala Gly Lys Thr Ile Thr Leu
                180                 185                 190
Glu Asp Gly Arg Gln Ile Asn Gly Ala Asp Tyr Leu Ala Ala Pro Val
                195                 200                 205
Pro Gly Lys Ala Leu Ala Ile Phe Gly Asp Thr Gly Pro Cys Asp Ala
210                 215                 220
Ala Leu Asp Leu Ala Lys Gly Val Asp Val Met Val His Glu Ala Thr
225                 230                 235                 240
Leu Asp Ile Thr Met Glu Ala Lys Ala Asn Ser Arg Gly His Ser Ser
                245                 250                 255
Thr Arg Gln Ala Ala Thr Leu Ala Arg Glu Ala Gly Val Gly Lys Leu
                260                 265                 270
Ile Ile Thr His Val Ser Ser Arg Tyr Asp Asp Lys Gly Cys Gln His
                275                 280                 285
Leu Leu Arg Glu Cys Arg Ser Ile Phe Pro Ala Thr Glu Leu Ala Asn
                290                 295                 300
Asp Phe Thr Val Phe Asn Val
305                 310
```

<210> SEQ ID NO 21
<211> LENGTH: 936
<212> TYPE: DNA
<213> ORGANISM: Escherichia coli

<400> SEQUENCE: 21

```
ttaaacgtta aacacggtga aatcattcgc cagttcagtc gccgggaaaa ttgacctgca    60
ttcacgtaac aggtgctgac aacctttgtc atcatagcgc gagctgacgt gggtaatgat   120
tagcttgccg actccagcct cacgggctag tgtcgcagcc tggcgtgtag agctatggcc   180
gcgactattg gctttggctt ccatggttat atccagcgtc gcttcgtgca ccatgacatc   240
gacacctta gccaggtcaa gtgcggcatc gcagggccg gtatcgccga aaatagcgag   300
cgctttacct ggcactggag cagctaagta atctgcgccg ttaatctgcc ttccatcttc   360
cagcgtgatt gttttgcccg cttttaattc ctgaaacagt gggccaggcg gcacgccagc   420
agcttttaat gcctgggcat ttaatgcacc cggtttatca tgttcttcaa tacgatagcc   480
ataacattcc agtgggtgtt ccagcggata agcggttact ttgcgcaggc catcatcgag   540
aatttcgcca gcgccaattt cgacaatttc cagcggataa tcggtccatg agccgctaat   600
```

```
ccgcagcgcg gtttccacaa attcacggat accttgcgga ccataaatcg ttaagggttg    660
gataatgcct gacatagaac gactgcacag caagccggt aaaccaaaaa gatgatcgcc    720
atgaaggtga ctgataaaaa tcttgtccag ttttccaggg ttaaaggcgg tatgcagtag    780
ctgatgctgg gtgccttcac cgcagtcaaa caaccaaagt ccgctctggg tcggatgttg    840
caggttaagc aatattgccg tgacattgcg cgtgcgggtt ggcacaccgg ctgaagtacc    900
taaaaaaatt aattccatga gttcatcacg tttcaa                              936
```

```
<210> SEQ ID NO 22
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 22
gtgttcgtgc tgacttgcac c                                              21

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 23
gaattatttc ctcccgttaa a                                              21

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 24
tgaagcctgt caaggacgag g                                              21

<210> SEQ ID NO 25
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 25
ccttacgtgg tcgaattgtg g                                              21

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 26
tgtatgaatt ggtacctcaa g                                              21

<210> SEQ ID NO 27
<211> LENGTH: 21
<212> TYPE: DNA
<213> ORGANISM: Artificial Sequence
<220> FEATURE:
```

-continued

<223> OTHER INFORMATION: Oligonucleotide for PCR

<400> SEQUENCE: 27
acaatggcaa tagttggtag g  21

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 28
gtggaaatct agcagtcaca g  21

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 29
atctggttct agcaggaagc g  21

<210> SEQ ID NO 30
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 30
cattgccagt cctgttgctg g  21

<210> SEQ ID NO 31
<211> LENGTH: 18
<212> TYPE: DNA
<213> ORGANISM: Artificial Sequence
<220> FEATURE:
<223> OTHER INFORMATION: Oligonucleotide for PCR

<400> SEQUENCE: 31
atggcatcca tgacatcg  18

<210> SEQ ID NO 32
<211> LENGTH: 27
<212> TYPE: DNA
<213> ORGANISM: Artificial Sequence
<220> FEATURE:
<223> OTHER INFORMATION: Oligonucleotide for PCR

<400> SEQUENCE: 32
cacaggaaac agctatgacc atgatta  27

<210> SEQ ID NO 33
<211> LENGTH: 26
<212> TYPE: DNA
<213> ORGANISM: Artificial Sequence
<220> FEATURE:
<223> OTHER INFORMATION: Oligonucleotide for PCR

<400> SEQUENCE: 33
gaaataaatg catctgtatt tgaatg  26

-continued

```
<210> SEQ ID NO 34
<211> LENGTH: 49
<212> TYPE: DNA
<213> ORGANISM: Artificial Sequence
<220> FEATURE:
<223> OTHER INFORMATION: Oligonucleotide for PCR

<400> SEQUENCE: 34
cacaggaaac agctatgacc atgattaaac taaagcaccc attagttca          49

<210> SEQ ID NO 35
<211> LENGTH: 51
<212> TYPE: DNA
<213> ORGANISM: Artificial Sequence
<220> FEATURE:
<223> OTHER INFORMATION: Oligonucleotide for PCR

<400> SEQUENCE: 35
cattcaaata cagatgcatt ttatttcctc atattataaa agccagtcat t        51

<210> SEQ ID NO 36
<211> LENGTH: 17
<212> TYPE: DNA
<213> ORGANISM: Artificial Sequence
<220> FEATURE:
<223> OTHER INFORMATION: Oligonucleotide for PCR

<400> SEQUENCE: 36
gccattgcgt ttgaaag                                              17

<210> SEQ ID NO 37
<211> LENGTH: 17
<212> TYPE: DNA
<213> ORGANISM: Artificial Sequence
<220> FEATURE:
<223> OTHER INFORMATION: Oligonucleotide for PCR

<400> SEQUENCE: 37
tgcttcgccg atttctt                                              17

<210> SEQ ID NO 38
<211> LENGTH: 49
<212> TYPE: DNA
<213> ORGANISM: Artificial Sequence
<220> FEATURE:
<223> OTHER INFORMATION: Oligonucleotide for PCR

<400> SEQUENCE: 38
taatcatggt catagctgtt cctgtgtat gaaagaaac ccttcagag             49

<210> SEQ ID NO 39
<211> LENGTH: 46
<212> TYPE: DNA
<213> ORGANISM: Artificial Sequence
<220> FEATURE:
<223> OTHER INFORMATION: Oligonucleotide for PCR

<400> SEQUENCE: 39
taatcatggt catagctgtt cctgtgcat accgaacgcc tttctt               46

<210> SEQ ID NO 40
<211> LENGTH: 48
<212> TYPE: DNA
<213> ORGANISM: Artificial Sequence
<220> FEATURE:
<223> OTHER INFORMATION: Oligonucleotide for PCR
```

-continued

```
<400> SEQUENCE: 40
gaaataaatg catctgtatt tgaatgtttt agaaaaccga atcagaga                48

<210> SEQ ID NO 41
<211> LENGTH: 43
<212> TYPE: DNA
<213> ORGANISM: Artificial Sequence
<220> FEATURE:
<223> OTHER INFORMATION: Oligonucleotide for PCR

<400> SEQUENCE: 41
gaaataaatg catctgtatt tgaatgaata gcgtggcggc ata                    43

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 42
attcagatcg aatactcctg                                              20

<210> SEQ ID NO 43
<211> LENGTH: 17
<212> TYPE: DNA
<213> ORGANISM: Artificial Sequence
<220> FEATURE:
<223> OTHER INFORMATION: Oligonucleotide for PCR

<400> SEQUENCE: 43
aaagcgggca aagcaga                                                 17
```